(12) United States Patent
Yi et al.

(10) Patent No.: US 10,932,793 B2
(45) Date of Patent: Mar. 2, 2021

(54) ENDOSCOPIC REPOSABLE SURGICAL CLIP APPLIER

(71) Applicant: Covidien LP, Mansfield, MA (US)

(72) Inventors: Peng Yi, Shanghai (CN); Kun Zhao, Shanghai (CN); Shunhong Xu, Shanghai (CN); Lin Chen, Shanghai (CN)

(73) Assignee: COVIDIEN LP, Mansfield, MA (US)

( * ) Notice: Subject to any disclaimer, the term of this patent is extended or adjusted under 35 U.S.C. 154(b) by 295 days.

(21) Appl. No.: 16/063,711

(22) PCT Filed: Jan. 11, 2016

(86) PCT No.: PCT/CN2016/070571
§ 371 (c)(1),
(2) Date: Jun. 19, 2018

(87) PCT Pub. No.: WO2017/120734
PCT Pub. Date: Jul. 20, 2017

(65) Prior Publication Data
US 2020/0261095 A1    Aug. 20, 2020

(51) Int. Cl.
*A61B 17/128* (2006.01)
*A61B 34/35* (2016.01)
*A61B 17/00* (2006.01)

(52) U.S. Cl.
CPC .......... *A61B 17/1285* (2013.01); *A61B 34/35* (2016.02); *A61B 2017/0023* (2013.01); *A61B 2017/00367* (2013.01)

(58) Field of Classification Search
CPC ......... A61B 17/04; A61B 17/00; A61B 17/08; A61B 17/10; A61B 17/122; A61B 17/128;

(Continued)

(56) References Cited

U.S. PATENT DOCUMENTS

| 3,120,230 A | 2/1964 | Skold |
|---|---|---|
| 3,363,628 A | 1/1968 | Wood |

(Continued)

FOREIGN PATENT DOCUMENTS

| AU | 2013254887 A1 | 11/2013 |
|---|---|---|
| CA | 1163889 A | 3/1984 |

(Continued)

OTHER PUBLICATIONS

European Office Action corresponding to EP 12 152 989.5 dated May 4, 2015.

(Continued)

*Primary Examiner* — George J Ulsh

(57) ABSTRACT

A reposable surgical clip applier (100) includes a handle assembly (110) having a housing, a trigger (114) and a drive assembly (120), the drive assembly (120) including a drive rod (122). The reposable surgical clip applier (100) further includes an outer tube assembly (200) disposed on a distal end of the housing and extending distally therefrom, and a clip cartridge assembly (300) selectively connectable to the distal end of the outer tube assembly (200). The clip cartridge assembly (300) includes an outer tube (314) and a pair of jaws (320*a*) fixedly supported in a distal end thereof, a first jaw pusher (130) in selective engagement with the distal end (122*b*) of the drive rod (122), a second jaw pusher (132) in selective engagement with the first jaw pusher (130) on a proximal end and the pair of jaws (320*a*) on a second end, and a plurality of surgical clips (C) disposed within the outer tube (314). A method of assembling a reposable surgical clip applier (100) is also provided.

12 Claims, 24 Drawing Sheets

(58) Field of Classification Search
CPC . A61B 17/083; A61B 17/105; A61B 17/1285; A61B 17/0023; A61B 17/00389; A61B 17/00407; A61B 17/0046; A61B 17/00477; A61B 17/0053; A61B 17/00907; A61B 17/72; A61B 2017/12004; A61B 17/11
See application file for complete search history.

(56) References Cited

U.S. PATENT DOCUMENTS

| | | |
|---|---|---|
| 3,638,847 A | 2/1972 | Noiles et al. |
| 3,675,688 A | 7/1972 | Bryan et al. |
| 3,735,762 A | 5/1973 | Bryan et al. |
| 3,867,944 A | 2/1975 | Samuels |
| 4,226,242 A | 10/1980 | Jarvik |
| 4,242,902 A | 1/1981 | Green |
| 4,296,751 A | 10/1981 | Blake, III et al. |
| 4,372,316 A | 2/1983 | Blake, III et al. |
| 4,408,603 A | 10/1983 | Blake, III et al. |
| 4,412,539 A | 11/1983 | Jarvik |
| 4,418,694 A | 12/1983 | Beroff et al. |
| 4,471,780 A | 9/1984 | Menges et al. |
| 4,480,640 A | 11/1984 | Becht |
| 4,480,641 A | 11/1984 | Failla et al. |
| 4,487,204 A | 12/1984 | Hrouda |
| 4,487,205 A | 12/1984 | Di Giovanni et al. |
| 4,491,133 A | 1/1985 | Menges et al. |
| 4,492,232 A | 1/1985 | Green |
| 4,498,476 A | 2/1985 | Cerwin et al. |
| 4,500,024 A | 2/1985 | Digiovanni et al. |
| 4,509,518 A | 4/1985 | McGarry et al. |
| 4,512,345 A | 4/1985 | Green |
| 4,522,207 A | 6/1985 | Klieman et al. |
| 4,532,925 A | 8/1985 | Blake, III |
| 4,534,351 A | 8/1985 | Rothfuss et al. |
| 4,545,377 A | 10/1985 | Cerwin et al. |
| 4,549,544 A | 10/1985 | Favaron |
| 4,556,058 A | 12/1985 | Green |
| 4,557,263 A | 12/1985 | Green |
| 4,562,839 A | 1/1986 | Blake, III et al. |
| 4,572,183 A | 2/1986 | Juska |
| 4,576,165 A | 3/1986 | Green et al. |
| 4,576,166 A | 3/1986 | Montgomery et al. |
| 4,590,937 A | 5/1986 | Deniega |
| 4,598,711 A | 7/1986 | Deniega |
| 4,602,631 A | 7/1986 | Funatsu |
| 4,611,595 A | 9/1986 | Klieman et al. |
| 4,612,932 A | 9/1986 | Caspar et al. |
| 4,616,650 A | 10/1986 | Green et al. |
| 4,616,651 A | 10/1986 | Golden |
| 4,624,254 A | 11/1986 | McGarry et al. |
| 4,637,395 A | 1/1987 | Caspar et al. |
| 4,646,740 A | 3/1987 | Peters et al. |
| 4,647,504 A | 3/1987 | Kimimura et al. |
| 4,658,822 A | 4/1987 | Kees, Jr. |
| 4,660,558 A | 4/1987 | Kees, Jr. |
| 4,662,373 A | 5/1987 | Montgomery et al. |
| 4,662,374 A | 5/1987 | Blake, III |
| 4,671,278 A | 6/1987 | Chin |
| 4,671,282 A | 6/1987 | Tretbar |
| 4,674,504 A | 6/1987 | Klieman et al. |
| 4,681,107 A | 7/1987 | Kees, Jr. |
| 4,696,396 A | 9/1987 | Samuels |
| 4,702,247 A | 10/1987 | Blake, III et al. |
| 4,706,668 A | 11/1987 | Backer |
| 4,712,549 A | 12/1987 | Peters et al. |
| 4,726,372 A | 2/1988 | Perlin |
| 4,733,666 A | 3/1988 | Mercer, Jr. |
| 4,759,364 A | 7/1988 | Boebel |
| 4,765,335 A | 8/1988 | Schmidt et al. |
| 4,777,949 A | 10/1988 | Perlin |
| 4,796,625 A | 1/1989 | Kees, Jr. |
| 4,799,481 A | 1/1989 | Transue et al. |
| 4,815,466 A | 3/1989 | Perlin |
| 4,821,721 A | 4/1989 | Chin et al. |
| 4,822,348 A | 4/1989 | Casey |
| 4,834,096 A | 5/1989 | Oh et al. |
| 4,850,355 A | 7/1989 | Brooks et al. |
| 4,854,317 A | 8/1989 | Braun |
| 4,856,517 A | 8/1989 | Collins et al. |
| 4,929,239 A | 5/1990 | Braun |
| 4,931,058 A | 6/1990 | Cooper |
| 4,934,364 A | 6/1990 | Green |
| 4,957,500 A | 9/1990 | Liang et al. |
| 4,966,603 A | 10/1990 | Focelle et al. |
| 4,967,949 A | 11/1990 | Sandhaus |
| 4,983,176 A | 1/1991 | Cushman et al. |
| 4,988,355 A | 1/1991 | Leveen et al. |
| 5,002,552 A | 3/1991 | Casey |
| 5,026,379 A | 6/1991 | Yoon |
| 5,030,224 A | 7/1991 | Wright et al. |
| 5,030,226 A | 7/1991 | Green et al. |
| 5,032,127 A | 7/1991 | Frazee et al. |
| 5,035,692 A | 7/1991 | Lyon et al. |
| 5,047,038 A | 9/1991 | Peters et al. |
| 5,049,152 A | 9/1991 | Simon et al. |
| 5,049,153 A | 9/1991 | Nakao et al. |
| 5,053,045 A | 10/1991 | Schmidt et al. |
| 5,059,202 A | 10/1991 | Liang et al. |
| 5,062,563 A | 11/1991 | Green et al. |
| 5,062,846 A | 11/1991 | Oh et al. |
| 5,078,731 A | 1/1992 | Hayhurst |
| 5,084,057 A | 1/1992 | Green et al. |
| 5,100,416 A | 3/1992 | Oh et al. |
| 5,100,420 A | 3/1992 | Green et al. |
| 5,104,394 A | 4/1992 | Knoepfler |
| 5,104,395 A | 4/1992 | Thornton et al. |
| 5,112,343 A | 5/1992 | Thornton |
| 5,122,150 A | 6/1992 | Puig |
| 5,127,915 A | 7/1992 | Mattson |
| 5,129,885 A | 7/1992 | Green et al. |
| 5,156,608 A | 10/1992 | Troidl et al. |
| 5,160,339 A | 11/1992 | Chen et al. |
| 5,163,945 A | 11/1992 | Ortiz et al. |
| 5,171,247 A | 12/1992 | Hughett et al. |
| 5,171,249 A | 12/1992 | Stefanchik et al. |
| 5,171,250 A | 12/1992 | Yoon |
| 5,171,251 A | 12/1992 | Bregen et al. |
| 5,171,252 A | 12/1992 | Friedland |
| 5,171,253 A | 12/1992 | Klieman |
| 5,192,288 A | 3/1993 | Thompson et al. |
| 5,197,970 A | 3/1993 | Green et al. |
| 5,199,566 A | 4/1993 | Ortiz et al. |
| 5,201,746 A | 4/1993 | Shichman |
| 5,201,900 A | 4/1993 | Nardella |
| 5,207,691 A | 5/1993 | Nardella |
| 5,207,692 A | 5/1993 | Kraus et al. |
| 5,217,473 A | 6/1993 | Yoon |
| 5,219,353 A | 6/1993 | Garvey, III et al. |
| 5,246,450 A | 9/1993 | Thornton et al. |
| 5,269,792 A | 12/1993 | Kovac et al. |
| 5,281,228 A | 1/1994 | Wolfson |
| 5,282,807 A | 2/1994 | Knoepfler |
| 5,282,808 A | 2/1994 | Kovac et al. |
| 5,282,832 A | 2/1994 | Toso et al. |
| 5,289,963 A | 3/1994 | McGarry et al. |
| 5,290,299 A | 3/1994 | Fain et al. |
| 5,300,081 A | 4/1994 | Young et al. |
| 5,304,183 A | 4/1994 | Gourlay et al. |
| 5,306,280 A | 4/1994 | Bregen et al. |
| 5,306,283 A | 4/1994 | Conners |
| 5,312,426 A | 5/1994 | Segawa et al. |
| 5,330,442 A | 7/1994 | Green et al. |
| 5,330,487 A | 7/1994 | Thornton et al. |
| 5,340,360 A | 8/1994 | Stefanchik |
| 5,342,373 A | 8/1994 | Stefanchik et al. |
| 5,354,304 A | 10/1994 | Allen et al. |
| 5,354,306 A | 10/1994 | Garvey, III et al. |
| 5,356,064 A | 10/1994 | Green et al. |
| 5,359,993 A | 11/1994 | Slater et al. |
| 5,366,458 A | 11/1994 | Korthoff et al. |
| 5,366,459 A | 11/1994 | Yoon |
| 5,368,600 A | 11/1994 | Failla et al. |
| 5,381,943 A | 1/1995 | Allen et al. |

(56) References Cited

U.S. PATENT DOCUMENTS

| | | |
|---|---|---|
| 5,382,253 A | 1/1995 | Hogendijk |
| 5,382,254 A | 1/1995 | McGarry et al. |
| 5,382,255 A | 1/1995 | Castro et al. |
| 5,383,880 A | 1/1995 | Hooven |
| 5,383,881 A | 1/1995 | Green et al. |
| 5,395,375 A | 3/1995 | Turkel et al. |
| 5,395,381 A | 3/1995 | Green et al. |
| 5,403,327 A | 4/1995 | Thornton et al. |
| 5,409,498 A | 4/1995 | Braddock et al. |
| 5,413,584 A | 5/1995 | Schulze |
| 5,423,835 A | 6/1995 | Green et al. |
| 5,425,740 A | 6/1995 | Hutchinson, Jr. |
| 5,431,667 A | 7/1995 | Thompson et al. |
| 5,431,668 A | 7/1995 | Burbank, III et al. |
| 5,431,669 A | 7/1995 | Thompson et al. |
| 5,439,468 A | 8/1995 | Schulze et al. |
| 5,441,509 A | 8/1995 | Vidal et al. |
| 5,447,513 A | 9/1995 | Davison et al. |
| 5,448,042 A | 9/1995 | Robinson et al. |
| 5,449,365 A | 9/1995 | Green et al. |
| 5,462,555 A | 10/1995 | Bolanos et al. |
| 5,462,558 A | 10/1995 | Kolesa et al. |
| 5,464,416 A | 11/1995 | Steckel |
| 5,474,566 A | 12/1995 | Alesi |
| 5,474,567 A | 12/1995 | Stefanchik et al. |
| 5,474,572 A | 12/1995 | Hayhurst |
| 5,487,499 A | 1/1996 | Sorrentino et al. |
| 5,487,746 A | 1/1996 | Yu et al. |
| 5,501,693 A | 3/1996 | Gravener |
| 5,509,920 A | 4/1996 | Phillips et al. |
| 5,514,149 A | 5/1996 | Green et al. |
| 5,520,701 A | 5/1996 | Lerch |
| 5,527,318 A | 6/1996 | McGarry |
| 5,527,319 A | 6/1996 | Green et al. |
| 5,527,320 A | 6/1996 | Carruthers et al. |
| 5,542,949 A | 8/1996 | Yoon |
| 5,547,474 A | 8/1996 | Kloeckl et al. |
| 5,562,655 A | 10/1996 | Mittelstadt et al. |
| 5,569,274 A | 10/1996 | Rapacki et al. |
| 5,571,121 A | 11/1996 | Heifetz |
| 5,575,802 A | 11/1996 | McQuilkin et al. |
| 5,582,615 A | 12/1996 | Foshee et al. |
| 5,584,840 A | 12/1996 | Ramsey et al. |
| 5,591,178 A | 1/1997 | Green et al. |
| 5,593,414 A | 1/1997 | Shipp et al. |
| 5,593,421 A | 1/1997 | Bauer |
| 5,601,573 A | 2/1997 | Fogelberg et al. |
| 5,601,574 A | 2/1997 | Stefanchik et al. |
| 5,607,436 A | 3/1997 | Pratt et al. |
| 5,618,291 A | 4/1997 | Thompson et al. |
| 5,618,306 A | 4/1997 | Roth et al. |
| 5,620,452 A | 4/1997 | Yoon |
| 5,626,585 A | 5/1997 | Mittelstadt et al. |
| 5,626,586 A | 5/1997 | Pistl et al. |
| 5,626,587 A | 5/1997 | Bishop et al. |
| 5,626,592 A | 5/1997 | Phillips et al. |
| RE35,525 E | 6/1997 | Stefanchik et al. |
| 5,634,930 A | 6/1997 | Thornton et al. |
| 5,643,291 A | 7/1997 | Pier et al. |
| 5,645,551 A | 7/1997 | Green et al. |
| 5,645,553 A | 7/1997 | Kolesa et al. |
| 5,649,937 A | 7/1997 | Bito et al. |
| 5,653,720 A | 8/1997 | Johnson et al. |
| 5,662,662 A | 9/1997 | Bishop et al. |
| 5,662,676 A | 9/1997 | Koninckx |
| 5,662,679 A | 9/1997 | Voss et al. |
| 5,665,097 A | 9/1997 | Baker et al. |
| 5,676,676 A | 10/1997 | Porter |
| 5,681,330 A | 10/1997 | Hughett et al. |
| 5,683,405 A | 11/1997 | Yacoubian et al. |
| 5,695,502 A | 12/1997 | Pier et al. |
| 5,695,505 A | 12/1997 | Yoon |
| 5,697,938 A | 12/1997 | Jensen et al. |
| 5,697,942 A | 12/1997 | Palti |
| 5,700,270 A | 12/1997 | Peyser et al. |
| 5,700,271 A | 12/1997 | Whitfield et al. |
| 5,702,048 A | 12/1997 | Eberlin |
| 5,709,706 A | 1/1998 | Kienzle et al. |
| 5,713,911 A | 2/1998 | Racenet et al. |
| 5,713,912 A | 2/1998 | Porter |
| 5,720,756 A | 2/1998 | Green et al. |
| 5,722,982 A | 3/1998 | Ferreira et al. |
| 5,725,537 A | 3/1998 | Green et al. |
| 5,725,538 A | 3/1998 | Green et al. |
| 5,725,542 A | 3/1998 | Yoon |
| 5,733,295 A | 3/1998 | Back et al. |
| 5,743,310 A | 4/1998 | Moran |
| 5,749,881 A | 5/1998 | Sackier et al. |
| 5,755,726 A | 5/1998 | Pratt et al. |
| 5,766,189 A | 6/1998 | Matsuno |
| 5,769,857 A | 6/1998 | Reztzov et al. |
| 5,772,673 A | 6/1998 | Cuny et al. |
| 5,776,146 A | 7/1998 | Sackier et al. |
| 5,776,147 A | 7/1998 | Dolendo |
| 5,779,718 A | 7/1998 | Green et al. |
| 5,779,720 A | 7/1998 | Walder-Utz et al. |
| 5,782,844 A | 7/1998 | Yoon et al. |
| 5,788,698 A | 8/1998 | Savornin |
| 5,792,149 A | 8/1998 | Sherts et al. |
| 5,792,150 A | 8/1998 | Pratt et al. |
| 5,797,922 A | 8/1998 | Hessel et al. |
| 5,809,075 A | 9/1998 | Townshend |
| 5,810,853 A | 9/1998 | Yoon |
| 5,817,116 A | 10/1998 | Takahashi et al. |
| 5,827,306 A | 10/1998 | Yoon |
| 5,827,323 A | 10/1998 | Klieman et al. |
| 5,833,695 A | 11/1998 | Yoon |
| 5,833,696 A | 11/1998 | Whitfield et al. |
| 5,833,700 A | 11/1998 | Fogelberg et al. |
| 5,835,199 A | 11/1998 | Phillips et al. |
| 5,843,097 A | 12/1998 | Mayenberger et al. |
| 5,843,101 A | 12/1998 | Fry |
| 5,846,255 A | 12/1998 | Casey |
| 5,849,019 A | 12/1998 | Yoon |
| 5,858,018 A | 1/1999 | Shipp et al. |
| 5,861,005 A | 1/1999 | Kontos |
| 5,868,759 A | 2/1999 | Peyser et al. |
| 5,868,761 A | 2/1999 | Nicholas et al. |
| 5,876,410 A | 3/1999 | Petillo |
| 5,895,394 A | 4/1999 | Kienzle et al. |
| 5,897,565 A | 4/1999 | Foster |
| 5,904,693 A | 5/1999 | Dicesare et al. |
| 5,906,625 A | 5/1999 | Bito et al. |
| 5,913,862 A | 6/1999 | Ramsey et al. |
| 5,913,876 A | 6/1999 | Taylor et al. |
| 5,918,791 A | 7/1999 | Sorrentino et al. |
| 5,921,991 A | 7/1999 | Whitehead et al. |
| 5,921,996 A | 7/1999 | Sherman |
| 5,921,997 A | 7/1999 | Fogelberg et al. |
| 5,928,251 A | 7/1999 | Aranyi et al. |
| 5,938,667 A | 8/1999 | Peyser et al. |
| 5,951,574 A | 9/1999 | Stefanchik et al. |
| 5,972,003 A | 10/1999 | Rousseau et al. |
| 5,976,159 A | 11/1999 | Bolduc et al. |
| 5,993,465 A | 11/1999 | Shipp et al. |
| 6,004,335 A | 12/1999 | Vaitekunas et al. |
| 6,009,551 A | 12/1999 | Sheynblat |
| 6,017,358 A | 1/2000 | Yoon et al. |
| 6,044,971 A | 4/2000 | Esposito et al. |
| 6,045,560 A | 4/2000 | McKean et al. |
| 6,053,908 A | 4/2000 | Crainich et al. |
| RE36,720 E | 5/2000 | Green et al. |
| 6,059,799 A | 5/2000 | Aranyi et al. |
| 6,099,536 A | 8/2000 | Petillo |
| 6,099,537 A | 8/2000 | Sugai et al. |
| 6,139,555 A | 10/2000 | Hart et al. |
| 6,210,418 B1 | 4/2001 | Storz et al. |
| 6,217,590 B1 | 4/2001 | Levinson |
| 6,228,097 B1 | 5/2001 | Levinson et al. |
| 6,241,740 B1 | 6/2001 | Davis et al. |
| 6,258,105 B1 | 7/2001 | Hart et al. |
| 6,261,302 B1 | 7/2001 | Voegele et al. |
| 6,273,898 B1 | 8/2001 | Kienzle et al. |
| 6,277,131 B1 | 8/2001 | Kalikow |

(56) References Cited

U.S. PATENT DOCUMENTS

| | | |
|---|---|---|
| 6,306,149 B1 | 10/2001 | Meade |
| 6,318,619 B1 | 11/2001 | Lee |
| 6,322,571 B1 | 11/2001 | Adams |
| 6,350,269 B1 | 2/2002 | Shipp et al. |
| 6,352,541 B1 | 3/2002 | Kienzle et al. |
| 6,391,035 B1 | 5/2002 | Appleby et al. |
| 6,423,079 B1 | 7/2002 | Blake, III |
| 6,428,548 B1 | 8/2002 | Durgin |
| 6,440,144 B1 | 8/2002 | Bacher |
| 6,461,363 B1 | 10/2002 | Gadberry et al. |
| 6,464,710 B1 | 10/2002 | Foster |
| 6,494,886 B1 | 12/2002 | Wilk et al. |
| 6,517,536 B2 | 2/2003 | Hooven et al. |
| 6,520,972 B2 | 2/2003 | Peters |
| 6,527,786 B1 | 3/2003 | Davis et al. |
| 6,537,289 B1 | 3/2003 | Kayan |
| 6,546,935 B2 | 4/2003 | Hooven |
| 6,551,333 B2 | 4/2003 | Kuhns et al. |
| 6,562,051 B1 | 5/2003 | Bolduc et al. |
| 6,569,171 B2 | 5/2003 | DeGuillebon et al. |
| 6,579,304 B1 | 6/2003 | Hart et al. |
| 6,599,298 B1 | 7/2003 | Forster et al. |
| 6,602,252 B2 | 8/2003 | Mollenauer |
| 6,607,540 B1 | 8/2003 | Shipp |
| 6,613,060 B2 | 9/2003 | Adams et al. |
| 6,626,916 B1 | 9/2003 | Yeung et al. |
| 6,626,922 B1 | 9/2003 | Hart et al. |
| 6,648,898 B1 | 11/2003 | Baxter |
| 6,652,538 B2 | 11/2003 | Kayan et al. |
| 6,652,539 B2 | 11/2003 | Shipp et al. |
| 6,656,193 B2 | 12/2003 | Grant et al. |
| 6,673,083 B1 | 1/2004 | Kayan et al. |
| 6,676,659 B2 | 1/2004 | Hutchins et al. |
| 6,679,894 B2 | 1/2004 | Damarati |
| RE38,445 E | 2/2004 | Pistl et al. |
| 6,695,854 B1 | 2/2004 | Kayan et al. |
| 6,706,057 B1 | 3/2004 | Bidoia et al. |
| 6,716,226 B2 | 4/2004 | Sixto, Jr. et al. |
| 6,723,109 B2 | 4/2004 | Solingen |
| 6,733,514 B2 | 5/2004 | Miser |
| 6,743,240 B2 | 6/2004 | Smith et al. |
| 6,743,241 B2 | 6/2004 | Kerr |
| 6,773,438 B1 | 8/2004 | Knodel et al. |
| 6,773,440 B2 | 8/2004 | Gannoe et al. |
| 6,776,783 B1 | 8/2004 | Frantzen et al. |
| 6,776,784 B2 | 8/2004 | Ginn |
| 6,780,195 B2 | 8/2004 | Porat |
| 6,793,663 B2 | 9/2004 | Kneifel et al. |
| 6,793,664 B2 | 9/2004 | Mazzocchi et al. |
| 6,802,848 B2 | 10/2004 | Anderson et al. |
| 6,814,742 B2 | 11/2004 | Kimura et al. |
| 6,818,009 B2 | 11/2004 | Hart et al. |
| 6,821,273 B2 | 11/2004 | Mollenauer |
| 6,821,284 B2 | 11/2004 | Sturtz et al. |
| 6,821,285 B2 | 11/2004 | Laufer et al. |
| 6,824,547 B2 | 11/2004 | Wilson, Jr. et al. |
| 6,824,548 B2 | 11/2004 | Smith et al. |
| 6,835,199 B2 | 12/2004 | McGuckin, Jr. et al. |
| 6,835,200 B2 | 12/2004 | Laufer et al. |
| 6,837,893 B2 | 1/2005 | Miller |
| 6,837,894 B2 | 1/2005 | Pugsley, Jr. et al. |
| 6,837,895 B2 | 1/2005 | Mayenberger |
| 6,840,945 B2 | 1/2005 | Manetakis et al. |
| 6,843,794 B2 | 1/2005 | Sixto, Jr. et al. |
| 6,849,078 B2 | 2/2005 | Durgin et al. |
| 6,849,079 B1 | 2/2005 | Blake, III et al. |
| 6,853,879 B2 | 2/2005 | Sunaoshi |
| 6,869,435 B2 | 3/2005 | Blake, III |
| 6,869,436 B2 | 3/2005 | Wendlandt |
| 6,889,116 B2 | 5/2005 | Jinno |
| 6,896,676 B2 | 5/2005 | Zubok et al. |
| 6,896,682 B1 | 5/2005 | McClellan et al. |
| 6,896,684 B2 | 5/2005 | Monassevitch et al. |
| 6,905,503 B2 | 6/2005 | Gifford, III et al. |
| 6,911,032 B2 | 6/2005 | Jugenheimer et al. |
| 6,911,033 B2 | 6/2005 | de Guillebon et al. |
| 6,913,607 B2 | 7/2005 | Ainsworth et al. |
| 6,916,327 B2 | 7/2005 | Northrup, III et al. |
| 6,916,332 B2 | 7/2005 | Adams |
| 6,923,818 B2 | 8/2005 | Muramatsu et al. |
| 6,939,356 B2 | 9/2005 | Debbas |
| 6,942,674 B2 | 9/2005 | Belef et al. |
| 6,942,676 B2 | 9/2005 | Buelna |
| 6,945,978 B1 | 9/2005 | Hyde |
| 6,945,979 B2 | 9/2005 | Kortenbach et al. |
| 6,949,107 B2 | 9/2005 | McGuckin, Jr. et al. |
| 6,953,465 B2 | 10/2005 | Dieck et al. |
| 6,955,643 B2 | 10/2005 | Gellman et al. |
| 6,959,852 B2 | 11/2005 | Shelton, IV et al. |
| 6,960,218 B2 | 11/2005 | Rennich |
| 6,960,221 B2 | 11/2005 | Ho et al. |
| 6,962,594 B1 | 11/2005 | Thevenet |
| 6,963,792 B1 | 11/2005 | Green |
| 6,964,363 B2 | 11/2005 | Wales et al. |
| 6,964,668 B2 | 11/2005 | Modesitt et al. |
| 6,966,875 B2 | 11/2005 | Longobardi |
| 6,966,917 B1 | 11/2005 | Suyker et al. |
| 6,966,919 B2 | 11/2005 | Sixto, Jr. et al. |
| 6,969,391 B1 | 11/2005 | Gazzani |
| 6,972,023 B2 | 12/2005 | Whayne et al. |
| 6,972,027 B2 | 12/2005 | Fallin et al. |
| 6,973,770 B2 | 12/2005 | Schnipke et al. |
| 6,974,462 B2 | 12/2005 | Sater |
| 6,974,466 B2 | 12/2005 | Ahmed et al. |
| 6,974,475 B1 | 12/2005 | Wall |
| 6,981,505 B2 | 1/2006 | Krause et al. |
| 6,981,628 B2 | 1/2006 | Wales |
| 6,991,635 B2 | 1/2006 | Takamoto et al. |
| 6,997,929 B2 | 2/2006 | Manzi et al. |
| 7,001,399 B2 | 2/2006 | Damarati |
| 7,037,315 B2 | 5/2006 | Sancoff et al. |
| 7,041,119 B2 | 5/2006 | Green |
| 7,052,504 B2 | 5/2006 | Hughett |
| 7,056,330 B2 | 6/2006 | Gayton |
| 7,070,602 B2 | 7/2006 | Smith et al. |
| 7,108,700 B2 | 9/2006 | Chan |
| 7,108,703 B2 | 9/2006 | Danitz et al. |
| 7,141,056 B2 | 11/2006 | Manetakis |
| 7,144,402 B2 | 12/2006 | Kuester, III |
| 7,175,648 B2 | 2/2007 | Nakao |
| 7,179,265 B2 | 2/2007 | Manetakis et al. |
| 7,207,997 B2 | 4/2007 | Shipp et al. |
| 7,211,091 B2 | 5/2007 | Fowler et al. |
| 7,211,092 B2 | 5/2007 | Hughett |
| 7,213,736 B2 | 5/2007 | Wales et al. |
| 7,214,230 B2 | 5/2007 | Brock et al. |
| 7,214,232 B2 | 5/2007 | Bowman et al. |
| 7,223,271 B2 | 5/2007 | Muramatsu et al. |
| 7,223,272 B2 | 5/2007 | Francese et al. |
| 7,232,445 B2 | 6/2007 | Kortenbach et al. |
| 7,238,191 B2 | 7/2007 | Bachmann |
| 7,261,724 B2 | 8/2007 | Molitor et al. |
| 7,261,725 B2 | 8/2007 | Binmoeller |
| 7,264,625 B1 | 9/2007 | Buncke |
| 7,288,098 B2 | 10/2007 | Huitema et al. |
| 7,297,149 B2 | 11/2007 | Vitali et al. |
| 7,312,188 B2 | 12/2007 | Kiso |
| 7,316,693 B2 | 1/2008 | Viola |
| 7,316,696 B2 | 1/2008 | Wilson, Jr. et al. |
| 7,322,995 B2 | 1/2008 | Buckman et al. |
| 7,326,223 B2 | 2/2008 | Wilson, Jr. |
| 7,329,266 B2 | 2/2008 | Royse et al. |
| 7,331,968 B2 | 2/2008 | Arp et al. |
| 7,338,503 B2 | 3/2008 | Rosenberg et al. |
| 7,357,805 B2 | 4/2008 | Masuda et al. |
| 7,367,939 B2 | 5/2008 | Smith et al. |
| 7,407,074 B2 | 8/2008 | Ortiz et al. |
| 7,419,495 B2 | 9/2008 | Menn et al. |
| 7,422,137 B2 | 9/2008 | Manzo |
| 7,431,724 B2 | 10/2008 | Manetakis et al. |
| 7,452,327 B2 | 11/2008 | Durgin et al. |
| 7,485,124 B2 | 2/2009 | Kuhns et al. |
| 7,488,335 B2 | 2/2009 | Sgro |
| 7,510,562 B2 | 3/2009 | Lindsay |

(56) References Cited

U.S. PATENT DOCUMENTS

| | | |
|---|---|---|
| 7,552,853 B2 | 6/2009 | Mas et al. |
| 7,559,937 B2 | 7/2009 | de la Torre et al. |
| 7,572,266 B2 | 8/2009 | Young et al. |
| 7,578,827 B2 | 8/2009 | Gadberry et al. |
| 7,582,095 B2 | 9/2009 | Shipp et al. |
| 7,585,304 B2 | 9/2009 | Hughett |
| 7,615,058 B2 | 11/2009 | Sixto, Jr. et al. |
| 7,615,060 B2 | 11/2009 | Stokes et al. |
| 7,621,926 B2 | 11/2009 | Wixey et al. |
| 7,637,917 B2 | 12/2009 | Whitfield et al. |
| 7,644,848 B2 | 1/2010 | Swayze et al. |
| 7,686,820 B2 | 3/2010 | Huitema et al. |
| 7,695,482 B2 | 4/2010 | Viola |
| 7,717,926 B2 | 5/2010 | Whitfield et al. |
| 7,727,247 B2 | 6/2010 | Kimura et al. |
| 7,727,248 B2 | 6/2010 | Smith et al. |
| 7,731,724 B2 | 6/2010 | Huitema et al. |
| 7,731,725 B2 | 6/2010 | Gadberry et al. |
| 7,736,388 B2 | 6/2010 | Goldfarb et al. |
| 7,740,639 B2 | 6/2010 | Hummel et al. |
| 7,740,641 B2 | 6/2010 | Huitema |
| 7,744,623 B2 | 6/2010 | Anderson |
| 7,752,853 B2 | 7/2010 | Singh et al. |
| 7,753,250 B2 | 7/2010 | Clauson et al. |
| 7,766,207 B2 | 8/2010 | Mather et al. |
| 7,766,925 B2 | 8/2010 | Stokes et al. |
| 7,770,773 B2 | 8/2010 | Whitman et al. |
| 7,776,058 B2 | 8/2010 | Rosenberg et al. |
| 7,780,688 B2 | 8/2010 | Sakakine et al. |
| 7,793,813 B2 | 9/2010 | Bettuchi |
| 7,806,903 B2 | 10/2010 | Shibata et al. |
| 7,819,886 B2 | 10/2010 | Whitfield et al. |
| 7,823,592 B2 | 11/2010 | Bettuchi et al. |
| 7,857,828 B2 | 12/2010 | Jabba et al. |
| 7,871,416 B2 | 1/2011 | Phillips |
| 7,875,029 B1 | 1/2011 | Hausen |
| 7,887,553 B2 | 2/2011 | Lehman et al. |
| 7,887,554 B2 | 2/2011 | Stokes et al. |
| 7,892,244 B2 | 2/2011 | Monassevitch et al. |
| 7,896,895 B2 | 3/2011 | Boudreaux et al. |
| 7,901,420 B2 | 3/2011 | Dunn |
| 7,905,890 B2 | 3/2011 | Whitfield et al. |
| 7,914,544 B2 | 3/2011 | Nguyen et al. |
| 7,914,551 B2 | 3/2011 | Ortiz et al. |
| 7,942,890 B2 | 5/2011 | D'Agostino et al. |
| 7,947,052 B2 | 5/2011 | Baxter, III et al. |
| 7,954,682 B2 | 6/2011 | Giordano et al. |
| 7,963,433 B2 | 6/2011 | Whitman et al. |
| 7,967,831 B2 | 6/2011 | Rosenberg et al. |
| 7,988,027 B2 | 8/2011 | Olson et al. |
| 7,998,155 B2 | 8/2011 | Manzo |
| 8,011,550 B2 | 9/2011 | Aranyi et al. |
| 8,011,555 B2 | 9/2011 | Tarinelli et al. |
| 8,016,178 B2 | 9/2011 | Olson et al. |
| 8,021,375 B2 | 9/2011 | Aldrich et al. |
| 8,021,378 B2 | 9/2011 | Sixto, Jr. et al. |
| 8,038,686 B2 | 10/2011 | Huiterna et al. |
| 8,048,088 B2 | 11/2011 | Green et al. |
| 8,056,565 B2 | 11/2011 | Zergiebel |
| 8,062,310 B2 | 11/2011 | Shibata et al. |
| 8,062,311 B2 | 11/2011 | Litscher et al. |
| 8,062,314 B2 | 11/2011 | Sixto, Jr. et al. |
| 8,066,720 B2 | 11/2011 | Knodel et al. |
| 8,066,721 B2 | 11/2011 | Kortenbach et al. |
| 8,066,722 B2 | 11/2011 | Miyagi et al. |
| 8,070,760 B2 | 12/2011 | Fujita |
| 8,074,857 B2 | 12/2011 | Peterson et al. |
| 8,075,571 B2 | 12/2011 | Vitali et al. |
| 8,080,021 B2 | 12/2011 | Griego |
| 8,083,668 B2 | 12/2011 | Durgin et al. |
| 8,088,061 B2 | 1/2012 | Wells et al. |
| 8,091,755 B2 | 1/2012 | Kayan et al. |
| 8,100,926 B1 | 1/2012 | Filshie et al. |
| 8,128,643 B2 | 3/2012 | Aranyi et al. |
| 8,133,240 B2 | 3/2012 | Damarati |
| 8,137,368 B2 | 3/2012 | Kayan et al. |
| 8,142,451 B2 | 3/2012 | Boulnois et al. |
| 8,157,145 B2 | 4/2012 | Shelton, IV et al. |
| 8,157,149 B2 | 4/2012 | Olson et al. |
| 8,157,151 B2 | 4/2012 | Ingmanson et al. |
| 8,172,859 B2 | 5/2012 | Matsuno et al. |
| 8,172,870 B2 | 5/2012 | Shipp |
| 8,177,797 B2 | 5/2012 | Shimoji et al. |
| 8,182,529 B2 | 5/2012 | Gordon et al. |
| 8,187,290 B2 | 5/2012 | Buckman et al. |
| 8,192,449 B2 | 6/2012 | Maier et al. |
| 8,211,119 B2 | 7/2012 | Palmer et al. |
| 8,211,120 B2 | 7/2012 | Itoh |
| 8,211,124 B2 | 7/2012 | Ainsworth et al. |
| 8,216,255 B2 | 7/2012 | Smith et al. |
| 8,216,257 B2 | 7/2012 | Huitema et al. |
| 8,236,012 B2 | 8/2012 | Molitor et al. |
| 8,241,322 B2 | 8/2012 | Whitman et al. |
| 8,246,634 B2 | 8/2012 | Huitema et al. |
| 8,246,635 B2 | 8/2012 | Huitema |
| 8,262,678 B2 | 9/2012 | Matsuoka et al. |
| 8,262,679 B2 | 9/2012 | Nguyen |
| 8,267,944 B2 | 9/2012 | Sorrentino et al. |
| 8,267,945 B2 | 9/2012 | Nguyen et al. |
| 8,267,946 B2 | 9/2012 | Whitfield et al. |
| 8,272,554 B2 | 9/2012 | Whitman et al. |
| 8,282,655 B2 | 10/2012 | Whitfield et al. |
| 8,287,559 B2 | 10/2012 | Barker et al. |
| 8,308,743 B2 | 11/2012 | Matsuno et al. |
| 8,313,497 B2 | 11/2012 | Walberg et al. |
| 8,328,822 B2 | 12/2012 | Huitema et al. |
| 8,336,556 B2 | 12/2012 | Zergiebel |
| 8,348,130 B2 | 1/2013 | Shah et al. |
| 8,357,171 B2 | 1/2013 | Whitfield et al. |
| 8,366,709 B2 | 2/2013 | Schechter et al. |
| 8,366,726 B2 | 2/2013 | Dennis |
| 8,371,491 B2 | 2/2013 | Huitema et al. |
| 8,372,095 B2 | 2/2013 | Viola |
| 8,382,773 B2 | 2/2013 | Whitfield et al. |
| 8,398,655 B2 | 3/2013 | Cheng et al. |
| 8,403,138 B2 | 3/2013 | Weisshaupt et al. |
| 8,403,945 B2 | 3/2013 | Whitfield et al. |
| 8,403,946 B2 | 3/2013 | Whitfield et al. |
| 8,408,442 B2 | 4/2013 | Racenet et al. |
| 8,409,222 B2 | 4/2013 | Whitfield et al. |
| 8,409,223 B2 | 4/2013 | Sorrentino et al. |
| 8,419,752 B2 | 4/2013 | Sorrentino et al. |
| 8,430,892 B2 | 4/2013 | Bindra et al. |
| 8,444,660 B2 | 5/2013 | Adams et al. |
| 8,465,460 B2 | 6/2013 | Yodfat et al. |
| 8,465,502 B2 | 6/2013 | Zergiebel |
| 8,475,473 B2 | 7/2013 | Vandenbroek et al. |
| 8,480,688 B2 | 7/2013 | Boulnois et al. |
| 8,486,091 B2 | 7/2013 | Sorrentino et al. |
| 8,491,608 B2 | 7/2013 | Sorrentino et al. |
| 8,496,673 B2 | 7/2013 | Nguyen et al. |
| 8,506,580 B2 | 8/2013 | Zergiebel et al. |
| 8,512,357 B2 | 8/2013 | Viola |
| 8,518,055 B1 | 8/2013 | Cardinale et al. |
| 8,523,882 B2 | 9/2013 | Huitema et al. |
| 8,529,585 B2 | 9/2013 | Jacobs et al. |
| 8,529,586 B2 | 9/2013 | Rosenberg et al. |
| 8,529,588 B2 | 9/2013 | Ahlberg et al. |
| 8,545,486 B2 | 10/2013 | Malkowski |
| 8,545,519 B2 | 10/2013 | Aguirre et al. |
| 8,556,920 B2 | 10/2013 | Huitema et al. |
| 8,568,430 B2 | 10/2013 | Shipp |
| 8,579,918 B2 | 11/2013 | Whitfield et al. |
| 8,585,716 B2 | 11/2013 | Roskopf et al. |
| 8,585,717 B2 | 11/2013 | Sorrentino et al. |
| 8,603,109 B2 | 12/2013 | Aranyi et al. |
| 8,623,044 B2 | 1/2014 | Timm et al. |
| 8,628,547 B2 | 1/2014 | Weller et al. |
| 8,632,520 B2 | 1/2014 | Otley |
| 8,636,191 B2 | 1/2014 | Meagher |
| 8,652,151 B2 | 2/2014 | Lehman et al. |
| 8,652,152 B2 | 2/2014 | Aranyi et al. |
| 8,663,247 B2 | 3/2014 | Menn et al. |
| 8,685,048 B2 | 4/2014 | Adams et al. |

(56) References Cited

U.S. PATENT DOCUMENTS

| | | |
|---|---|---|
| 8,690,899 B2 | 4/2014 | Kogiso et al. |
| 8,708,210 B2 | 4/2014 | Zemlok et al. |
| 8,708,213 B2 | 4/2014 | Shelton, IV et al. |
| 8,709,027 B2 | 4/2014 | Adams et al. |
| 8,715,299 B2 | 5/2014 | Menn et al. |
| 8,720,766 B2 | 5/2014 | Hess et al. |
| 8,734,469 B2 | 5/2014 | Pribanic et al. |
| 8,747,423 B2 | 6/2014 | Whitfield et al. |
| 8,753,356 B2 | 6/2014 | Vitali et al. |
| 8,758,392 B2 | 6/2014 | Crainich |
| 8,771,169 B2 | 7/2014 | Whitman et al. |
| 8,795,302 B2 | 8/2014 | Wild |
| 8,808,310 B2 | 8/2014 | Jones et al. |
| 8,814,884 B2 | 8/2014 | Whitfield et al. |
| 8,821,516 B2 | 9/2014 | Huitema |
| 8,839,954 B2 | 9/2014 | Disch |
| 8,845,659 B2 | 9/2014 | Whitfield et al. |
| 8,894,665 B2 | 11/2014 | Sorrentino et al. |
| 8,894,666 B2 | 11/2014 | Schulz et al. |
| 8,900,253 B2 | 12/2014 | Aranyi et al. |
| 8,915,930 B2 | 12/2014 | Huitema et al. |
| 8,915,931 B2 | 12/2014 | Boudreaux et al. |
| 8,939,974 B2 | 1/2015 | Boudreaux et al. |
| 8,945,151 B2 | 2/2015 | Salas |
| 8,950,646 B2 | 2/2015 | Viola |
| 8,968,337 B2 | 3/2015 | Whitfield et al. |
| 8,968,342 B2 | 3/2015 | Wingardner, III et al. |
| 8,973,804 B2 | 3/2015 | Hess et al. |
| 8,986,343 B2 | 3/2015 | Bourque et al. |
| 8,998,935 B2 | 4/2015 | Hart |
| 9,011,464 B2 | 4/2015 | Zammataro |
| 9,011,465 B2 | 4/2015 | Whitfield et al. |
| 9,028,511 B2 | 5/2015 | Weller et al. |
| 9,060,779 B2 | 6/2015 | Martinez |
| 9,084,604 B2 | 7/2015 | Litscher et al. |
| 9,089,334 B2 | 7/2015 | Sorrentino et al. |
| 9,113,892 B2 | 8/2015 | Malkowski et al. |
| 9,113,893 B2 | 8/2015 | Sorrentino et al. |
| 9,119,629 B2 | 9/2015 | Cardinale et al. |
| 9,186,136 B2 | 11/2015 | Malkowski et al. |
| 9,186,153 B2 | 11/2015 | Zammataro |
| 9,208,429 B2 | 12/2015 | Thornton et al. |
| 9,220,507 B1 | 12/2015 | Patel |
| 9,226,825 B2 | 1/2016 | Starksen et al. |
| 9,232,947 B2 | 1/2016 | Brenner et al. |
| 9,265,486 B2 | 2/2016 | Hughett, Sr. et al. |
| 9,271,737 B2 | 3/2016 | Castro et al. |
| 9,282,972 B1 | 3/2016 | Patel |
| 9,282,973 B2 | 3/2016 | Hughett, Sr. et al. |
| 9,358,011 B2 | 6/2016 | Sorrentino et al. |
| 9,364,216 B2 | 6/2016 | Rockrohr et al. |
| 9,364,240 B2 | 6/2016 | Whitfield et al. |
| 9,370,400 B2 | 6/2016 | Parihar |
| 9,393,024 B2 | 7/2016 | Whitfield et al. |
| 9,408,610 B2 | 8/2016 | Hartournbekis |
| 9,414,844 B2 | 8/2016 | Zergiebel et al. |
| 9,433,411 B2 | 9/2016 | Racenet et al. |
| 9,433,422 B2 | 9/2016 | Crainich et al. |
| 9,439,654 B2 | 9/2016 | Sorrentino et al. |
| 9,445,810 B2 | 9/2016 | Cappola |
| 9,445,820 B2 | 9/2016 | Whiting |
| 9,456,824 B2 | 10/2016 | Willett et al. |
| 9,468,444 B2 | 10/2016 | Menn et al. |
| 9,480,477 B2 | 11/2016 | Aranyi et al. |
| 9,480,480 B2 | 11/2016 | Santilli et al. |
| 9,486,225 B2 | 11/2016 | Michler et al. |
| 9,498,227 B2 | 11/2016 | Zergiebel et al. |
| 9,504,472 B2 | 11/2016 | Kamler |
| 9,517,064 B2 | 12/2016 | Sarradon |
| 9,526,501 B2 | 12/2016 | Malkowski |
| 9,526,565 B2 | 12/2016 | Strobl |
| 9,532,787 B2 | 1/2017 | Zammataro |
| 9,545,254 B2 | 1/2017 | Sorrentino et al. |
| 9,549,741 B2 | 1/2017 | Zergiebel |
| 9,561,038 B2 | 2/2017 | Shelton, IV et al. |
| 9,566,066 B2 | 2/2017 | Kasvikis |
| 9,597,089 B2 | 3/2017 | Menn |
| 9,642,627 B2 | 5/2017 | Zammataro |
| 9,681,877 B2 | 6/2017 | Blake, III et al. |
| 9,687,247 B2 | 6/2017 | Aranyi et al. |
| 9,700,324 B2 | 7/2017 | Mazzucco et al. |
| 9,717,504 B2 | 8/2017 | Huitema |
| 9,717,505 B2 | 8/2017 | Whitfield et al. |
| 9,724,163 B2 | 8/2017 | Orban |
| 9,737,310 B2 | 8/2017 | Whitfield et al. |
| 9,750,500 B2 | 9/2017 | Malkowski |
| 9,763,668 B2 | 9/2017 | Whitfield et al. |
| 9,763,669 B2 | 9/2017 | Griego |
| 9,775,623 B2 | 10/2017 | Zammataro et al. |
| 9,775,624 B2 | 10/2017 | Rockrohr et al. |
| 9,782,164 B2 | 10/2017 | Mumaw et al. |
| 9,782,181 B2 | 10/2017 | Vitali et al. |
| 9,808,257 B2 | 11/2017 | Armenteros et al. |
| 9,848,886 B2 | 12/2017 | Malkowski et al. |
| 9,855,043 B2 | 1/2018 | Malkowski |
| 9,883,866 B2 | 2/2018 | Roundy et al. |
| 9,931,124 B2 | 4/2018 | Gokharu |
| 9,968,361 B2 | 5/2018 | Aranyi et al. |
| 9,968,362 B2 | 5/2018 | Malkowski et al. |
| 10,004,502 B2 | 6/2018 | Malkowski et al. |
| 10,136,939 B2 | 11/2018 | Minnelli et al. |
| 10,159,484 B2 | 12/2018 | Sorrentino et al. |
| 10,159,491 B2 | 12/2018 | Gokharu |
| 10,159,492 B2 | 12/2018 | Zammataro |
| 10,166,027 B2 | 1/2019 | Aranyi et al. |
| 10,231,732 B1 | 3/2019 | Racenet et al. |
| 10,231,735 B2 | 3/2019 | Sorrentino et al. |
| 10,231,738 B2 | 3/2019 | Sorrentino et al. |
| 10,258,346 B2 | 4/2019 | Zergiebel et al. |
| 10,271,854 B2 | 4/2019 | Whitfield et al. |
| 10,292,712 B2 | 5/2019 | Shankarsetty |
| 10,349,936 B2 | 7/2019 | Rockrohr et al. |
| 10,349,950 B2 | 7/2019 | Aranyi |
| 10,357,250 B2 | 7/2019 | Zammataro |
| 10,363,045 B2 | 7/2019 | Whitfield et al. |
| 10,368,876 B2 | 8/2019 | Bhatnagar et al. |
| 10,390,831 B2 | 8/2019 | Holsten et al. |
| 10,426,489 B2 | 10/2019 | Baril |
| 2002/0123742 A1 | 9/2002 | Baxter et al. |
| 2003/0014060 A1 | 1/2003 | Wilson et al. |
| 2003/0114867 A1 | 6/2003 | Bolduc et al. |
| 2003/0208231 A1 | 11/2003 | Williamson et al. |
| 2003/0229360 A1 | 12/2003 | Gayton |
| 2004/0097970 A1 | 5/2004 | Hughett |
| 2004/0097971 A1 | 5/2004 | Hughett |
| 2004/0133215 A1 | 7/2004 | Baxter |
| 2004/0138681 A1 | 7/2004 | Pier |
| 2004/0167545 A1 | 8/2004 | Sadler et al. |
| 2004/0176783 A1 | 9/2004 | Edoga et al. |
| 2004/0176784 A1 | 9/2004 | Okada |
| 2004/0193213 A1 | 9/2004 | Aranyi et al. |
| 2004/0230198 A1 | 11/2004 | Manzi et al. |
| 2004/0232197 A1 | 11/2004 | Shelton et al. |
| 2005/0010242 A1 | 1/2005 | Lindsay |
| 2005/0090837 A1 | 4/2005 | Sixto et al. |
| 2005/0096670 A1 | 5/2005 | Wellman et al. |
| 2005/0096671 A1 | 5/2005 | Wellman et al. |
| 2005/0107810 A1 | 5/2005 | Morales et al. |
| 2005/0107811 A1 | 5/2005 | Starksen et al. |
| 2005/0107871 A1 | 5/2005 | Realyvasquez et al. |
| 2005/0125010 A1 | 6/2005 | Smith et al. |
| 2005/0149068 A1 | 7/2005 | Williams et al. |
| 2005/0149069 A1 | 7/2005 | Bertolero et al. |
| 2005/0171560 A1 | 8/2005 | Hughett |
| 2005/0175703 A1 | 8/2005 | Hunter et al. |
| 2005/0177176 A1 | 8/2005 | Gerbi et al. |
| 2005/0216036 A1 | 9/2005 | Nakao |
| 2005/0216056 A1 | 9/2005 | Valdevit et al. |
| 2005/0222665 A1 | 10/2005 | Aranyi |
| 2005/0228416 A1 | 10/2005 | Burbank et al. |
| 2005/0234478 A1 | 10/2005 | Wixey et al. |
| 2005/0256529 A1 | 11/2005 | Yawata et al. |
| 2005/0267495 A1 | 12/2005 | Ginn et al. |
| 2005/0273122 A1 | 12/2005 | Theroux et al. |

(56) References Cited

U.S. PATENT DOCUMENTS

| | | |
|---|---|---|
| 2005/0277956 A1 | 12/2005 | Francese et al. |
| 2005/0277958 A1 | 12/2005 | Levinson |
| 2005/0288689 A1 | 12/2005 | Kammerer et al. |
| 2006/0000867 A1 | 1/2006 | Shelton et al. |
| 2006/0004388 A1 | 1/2006 | Whayne et al. |
| 2006/0009789 A1 | 1/2006 | Gambale et al. |
| 2006/0009790 A1 | 1/2006 | Blake et al. |
| 2006/0009792 A1 | 1/2006 | Baker et al. |
| 2006/0020271 A1 | 1/2006 | Stewart et al. |
| 2006/0079115 A1 | 4/2006 | Aranyi |
| 2006/0085015 A1 | 4/2006 | Whitfield et al. |
| 2006/0085021 A1 | 4/2006 | Wenzler |
| 2006/0100649 A1 | 5/2006 | Hart |
| 2006/0124485 A1 | 6/2006 | Kennedy |
| 2006/0163312 A1 | 7/2006 | Viola et al. |
| 2006/0173470 A1 | 8/2006 | Oray et al. |
| 2006/0190013 A1 | 8/2006 | Menn |
| 2006/0217749 A1 | 9/2006 | Wilson et al. |
| 2006/0224165 A1 | 10/2006 | Surti et al. |
| 2006/0224170 A1 | 10/2006 | Duff |
| 2006/0235439 A1 | 10/2006 | Molitor et al. |
| 2006/0241655 A1 | 10/2006 | Viola |
| 2006/0259045 A1 | 11/2006 | Damarati |
| 2006/0259049 A1 | 11/2006 | Harada et al. |
| 2007/0021766 A1 | 1/2007 | Belagali et al. |
| 2007/0038233 A1 | 2/2007 | Martinez et al. |
| 2007/0049947 A1 | 3/2007 | Menn et al. |
| 2007/0049949 A1 | 3/2007 | Manetakis |
| 2007/0049950 A1 | 3/2007 | Theroux et al. |
| 2007/0049951 A1 | 3/2007 | Menn |
| 2007/0083218 A1 | 4/2007 | Morris |
| 2007/0093790 A1 | 4/2007 | Downey et al. |
| 2007/0112365 A1 | 5/2007 | Hilal et al. |
| 2007/0118161 A1 | 5/2007 | Kennedy et al. |
| 2007/0118174 A1 | 5/2007 | Chu |
| 2007/0173866 A1 | 7/2007 | Sorrentino et al. |
| 2007/0185504 A1 | 8/2007 | Manetakis et al. |
| 2007/0191868 A1 | 8/2007 | Theroux et al. |
| 2007/0203510 A1 | 8/2007 | Bettuchi |
| 2007/0276417 A1 | 11/2007 | Mendes, Jr. et al. |
| 2007/0282355 A1 | 12/2007 | Brown et al. |
| 2007/0288039 A1 | 12/2007 | Aranyi et al. |
| 2007/0293875 A1 | 12/2007 | Soetikno et al. |
| 2008/0004636 A1 | 1/2008 | Walberg et al. |
| 2008/0045981 A1 | 2/2008 | Margolin et al. |
| 2008/0051808 A1 | 2/2008 | Rivera et al. |
| 2008/0103510 A1 | 5/2008 | Taylor et al. |
| 2008/0147092 A1 | 6/2008 | Rogge et al. |
| 2008/0167665 A1 | 7/2008 | Arp et al. |
| 2008/0228199 A1 | 9/2008 | Cropper et al. |
| 2008/0255413 A1 | 10/2008 | Zemlok et al. |
| 2008/0255589 A1 | 10/2008 | Blakeney et al. |
| 2008/0306492 A1 | 12/2008 | Shibata et al. |
| 2008/0306493 A1 | 12/2008 | Shibata et al. |
| 2008/0312670 A1 | 12/2008 | Lutze et al. |
| 2009/0088783 A1 | 4/2009 | Kennedy et al. |
| 2009/0182193 A1 | 7/2009 | Whitman et al. |
| 2009/0204115 A1 | 8/2009 | Dees, Jr. et al. |
| 2009/0209946 A1 | 8/2009 | Swayze et al. |
| 2009/0228023 A1 | 9/2009 | Cui |
| 2009/0261142 A1 | 10/2009 | Milliman et al. |
| 2009/0264904 A1 | 10/2009 | Aldrich et al. |
| 2009/0312775 A1 | 12/2009 | Gilkey et al. |
| 2009/0326558 A1 | 12/2009 | Cui et al. |
| 2010/0057102 A1 | 3/2010 | Sorrentino et al. |
| 2010/0089970 A1 | 4/2010 | Smith et al. |
| 2010/0274264 A1 | 10/2010 | Schulz et al. |
| 2010/0318103 A1 | 12/2010 | Cheng et al. |
| 2010/0331862 A1 | 12/2010 | Monassevitch et al. |
| 2011/0054498 A1 | 3/2011 | Monassevitch et al. |
| 2011/0087220 A1 | 4/2011 | Felder et al. |
| 2011/0087268 A1 | 4/2011 | Livneh |
| 2011/0144662 A1 | 6/2011 | McLawhorn et al. |
| 2011/0208211 A1 | 8/2011 | Whitfield et al. |
| 2011/0208212 A1 | 8/2011 | Lergiebel et al. |
| 2011/0218554 A1 | 9/2011 | Cheng et al. |
| 2011/0224700 A1 | 9/2011 | Schmidt et al. |
| 2011/0295290 A1 | 12/2011 | Whitfield |
| 2011/0313437 A1 | 12/2011 | Yeh |
| 2012/0022526 A1 | 1/2012 | Aldridge et al. |
| 2012/0029533 A1 | 2/2012 | Whitfield et al. |
| 2012/0046671 A1 | 2/2012 | Matsuoka et al. |
| 2012/0048759 A1 | 3/2012 | Disch et al. |
| 2012/0053402 A1 | 3/2012 | Conlon et al. |
| 2012/0226291 A1 | 9/2012 | Malizia et al. |
| 2012/0253298 A1 | 10/2012 | Henderson et al. |
| 2012/0265220 A1 | 10/2012 | Menn |
| 2012/0330326 A1 | 12/2012 | Creston et al. |
| 2013/0041379 A1 | 2/2013 | Bodor et al. |
| 2013/0131697 A1 | 5/2013 | Hartournbekis |
| 2013/0165951 A1 | 6/2013 | Blake, III |
| 2013/0172909 A1 | 7/2013 | Harris |
| 2013/0172910 A1 | 7/2013 | Malkowski |
| 2013/0175320 A1 | 7/2013 | Mandakolathur Vasudevan et al. |
| 2013/0226200 A1 | 8/2013 | Kappel et al. |
| 2013/0253540 A1 | 9/2013 | Castro et al. |
| 2013/0325040 A1 | 12/2013 | Lammataro |
| 2013/0325057 A1 | 12/2013 | Larson et al. |
| 2014/0074143 A1 | 3/2014 | Fitzgerald et al. |
| 2014/0188159 A1 | 7/2014 | Steege |
| 2014/0263565 A1 | 9/2014 | Lytle, IV et al. |
| 2014/0276970 A1 | 9/2014 | Messerly et al. |
| 2014/0324074 A1 | 10/2014 | Crainich et al. |
| 2014/0371728 A1 | 12/2014 | Vaughn |
| 2015/0032131 A1 | 1/2015 | Sorrentino et al. |
| 2015/0196298 A1 | 7/2015 | Menn et al. |
| 2015/0201953 A1 | 7/2015 | Strobl et al. |
| 2015/0265282 A1 | 9/2015 | Miles et al. |
| 2015/0313452 A1 | 11/2015 | Hasser et al. |
| 2015/0314451 A1 | 11/2015 | Nixon |
| 2016/0004956 A1 | 1/2016 | Reynolds et al. |
| 2016/0030044 A1 | 2/2016 | Zammataro |
| 2016/0113655 A1 | 4/2016 | Holsten |
| 2016/0151071 A1 | 6/2016 | Tokarz et al. |
| 2016/0213377 A1 | 7/2016 | Shankarsetty |
| 2016/0242767 A1 | 8/2016 | Kasvikis |
| 2016/0242789 A1 | 8/2016 | Sorrentino et al. |
| 2016/0256157 A1 | 9/2016 | Rockrohr et al. |
| 2016/0256158 A1 | 9/2016 | Whitfield et al. |
| 2016/0262764 A1 | 9/2016 | Gokharu |
| 2016/0296236 A1 | 10/2016 | Whitfield et al. |
| 2016/0338695 A1 | 11/2016 | Hartournbekis |
| 2016/0338699 A1 | 11/2016 | Sorrentino et al. |
| 2017/0027581 A1 | 2/2017 | Zergiebel et al. |
| 2017/0049449 A1 | 2/2017 | Aranyi et al. |
| 2017/0065277 A1 | 3/2017 | Malkowski |
| 2017/0065281 A1 | 3/2017 | Zammataro |
| 2017/0086846 A1 | 3/2017 | Sorrentino et al. |
| 2017/0086850 A1 | 3/2017 | Zergiebel |
| 2017/0128071 A1 | 5/2017 | Holsten et al. |
| 2017/0172780 A1 | 6/2017 | Murthy Aravalli |
| 2017/0202567 A1 | 7/2017 | Griffiths et al. |
| 2017/0238936 A1 | 8/2017 | Mujawar |
| 2017/0245921 A1 | 8/2017 | Joseph et al. |
| 2017/0252042 A1 | 9/2017 | Kethman et al. |
| 2017/0258472 A1 | 9/2017 | Aranyi et al. |
| 2017/0290587 A1 | 10/2017 | Schober et al. |
| 2017/0325814 A1 | 11/2017 | Malkowski |
| 2017/0340325 A1 | 11/2017 | Baril et al. |
| 2017/0340331 A1 | 11/2017 | Hu et al. |
| 2017/0340332 A1 | 11/2017 | Whitfield et al. |
| 2017/0360449 A1 | 12/2017 | Rockrohr et al. |
| 2018/0008276 A1 | 1/2018 | Bhatnagar et al. |
| 2018/0008277 A1 | 1/2018 | Baril |
| 2018/0021041 A1 | 1/2018 | Zhang et al. |
| 2018/0070952 A1 | 3/2018 | Malkowski et al. |
| 2018/0116671 A1 | 5/2018 | Prior |
| 2018/0116673 A1 | 5/2018 | Baril et al. |
| 2018/0116674 A1 | 5/2018 | Baril |
| 2018/0116675 A1 | 5/2018 | Baril |
| 2018/0116676 A1 | 5/2018 | Williams |
| 2018/0168660 A1 | 6/2018 | Gokharu |
| 2018/0214156 A1 | 8/2018 | Baril et al. |
| 2018/0221028 A1 | 8/2018 | Williams |

(56) References Cited

U.S. PATENT DOCUMENTS

| | | |
|---|---|---|
| 2018/0228492 A1 | 8/2018 | Aranyi et al. |
| 2018/0228567 A1 | 8/2018 | Baril et al. |
| 2018/0235632 A1 | 8/2018 | Mujawar et al. |
| 2018/0235633 A1 | 8/2018 | Baril et al. |
| 2018/0235637 A1 | 8/2018 | Xu et al. |
| 2018/0242977 A1 | 8/2018 | Tan et al. |
| 2018/0263624 A1 | 9/2018 | Malkowski et al. |
| 2018/0271526 A1 | 9/2018 | Zammataro |
| 2018/0317927 A1 | 11/2018 | Cai et al. |
| 2018/0317928 A1 | 11/2018 | P V R |
| 2018/0325519 A1 | 11/2018 | Baril et al. |
| 2019/0000449 A1 | 1/2019 | Baril et al. |
| 2019/0000482 A1 | 1/2019 | Hu et al. |
| 2019/0000584 A1 | 1/2019 | Baril |
| 2019/0021738 A1 | 1/2019 | Hartoumbekis |
| 2019/0038375 A1 | 2/2019 | Baril et al. |
| 2019/0046202 A1 | 2/2019 | Baril et al. |
| 2019/0046203 A1 | 2/2019 | Baril et al. |
| 2019/0046207 A1 | 2/2019 | Czemik et al. |
| 2019/0046208 A1 | 2/2019 | Baril et al. |
| 2019/0053806 A1 | 2/2019 | Zhang et al. |
| 2019/0053808 A1 | 2/2019 | Baril et al. |
| 2019/0059904 A1 | 2/2019 | Zammataro |
| 2019/0076147 A1 | 3/2019 | Baril et al. |
| 2019/0076148 A1 | 3/2019 | Baril et al. |
| 2019/0076149 A1 | 3/2019 | Baril et al. |
| 2019/0076150 A1 | 3/2019 | Gokharu |
| 2019/0076210 A1 | 3/2019 | Baril et al. |
| 2019/0133583 A1 | 5/2019 | Baril et al. |
| 2019/0133584 A1 | 5/2019 | Baril et al. |
| 2019/0133593 A1 | 5/2019 | P V R |
| 2019/0133594 A1 | 5/2019 | Dinino et al. |
| 2019/0133595 A1 | 5/2019 | Baril et al. |
| 2019/0150935 A1 | 5/2019 | Raikar et al. |
| 2019/0175176 A1 | 6/2019 | Zammataro |
| 2019/0175187 A1 | 6/2019 | P V R |
| 2019/0175188 A1 | 6/2019 | P V R |
| 2019/0175189 A1 | 6/2019 | P V R |
| 2019/0192139 A1 | 6/2019 | Rockrohr et al. |
| 2019/0209177 A1 | 7/2019 | Whitfield et al. |
| 2019/0216464 A1 | 7/2019 | Baril et al. |
| 2019/0239893 A1 | 8/2019 | Shankarsetty |

FOREIGN PATENT DOCUMENTS

| | | |
|---|---|---|
| CN | 202699217 U | 1/2013 |
| CN | 103251441 A | 8/2013 |
| CN | 104605911 B | 2/2017 |
| DE | 29520789 U1 | 6/1996 |
| DE | 202005001664 U1 | 5/2005 |
| DE | 202007003398 U1 | 6/2007 |
| DE | 202009006113 U1 | 7/2009 |
| EP | 0000756 A1 | 2/1979 |
| EP | 0406724 A1 | 1/1991 |
| EP | 0514139 A2 | 11/1992 |
| EP | 0576835 A2 | 1/1994 |
| EP | 0732078 A2 | 9/1996 |
| EP | 0769274 A1 | 4/1997 |
| EP | 1769757 A1 | 4/2007 |
| EP | 2158851 | 3/2010 |
| EP | 2361562 A1 | 8/2011 |
| EP | 2412318 A2 | 2/2012 |
| EP | 3132756 A1 | 2/2017 |
| GB | 2073022 A | 10/1981 |
| JP | 2003033361 A | 2/2003 |
| JP | 2006054858 A | 2/2006 |
| JP | 2006154230 A | 6/2006 |
| JP | 2006277221 A | 10/2006 |
| JP | 2008017876 A | 1/2008 |
| JP | 2009215693 A | 9/2009 |
| JP | 2011186812 A | 9/2011 |
| JP | 2013166982 A | 8/2013 |
| WO | 903763 A1 | 4/1990 |
| WO | 0042922 A1 | 7/2000 |
| WO | 0166001 A2 | 9/2001 |
| WO | 0167965 A1 | 9/2001 |
| WO | 2016192096 A1 | 12/2016 |
| WO | 2016192718 A2 | 12/2016 |
| WO | 2016197350 A1 | 12/2016 |
| WO | 2016206015 A1 | 12/2016 |
| WO | 2017084000 A1 | 5/2017 |
| WO | 2017146138 A1 | 8/2017 |

OTHER PUBLICATIONS

Australian Office Action corresponding to AU 2009212759 dated May 7, 2015.
Chinese Office Action corresponding to Int'l Appln No. CN 201210212642.9 dated Jun. 3, 2015.
European Office Action corresponding to Int'l Appln No. EP 04 719 757.9 dated Jun. 12, 2015.
European Office Action corresponding to Int'l Appln No. EP 13 166 382.5 dated Jun. 19, 2015.
Japanese Office Action corresponding to Int'l Application No. JP 2010-226908 dated Jun. 26, 2015.
Extended European Search Report corresponding to Int'l Application. No. EP 15 15 5024.1 dated Jul. 17, 2015.
Extended European Search Report corresponding to Int'l Application. No. EP 14 19 2026.4 dated Jul. 17, 2015.
Japanese Office Action corresponding to Int'l Application No. JP 2011-160126 dated Aug. 10, 2015.
Extended European Search Report corresponding to Int'l Application. No. EP 14 15 0321.9 dated Sep. 23, 2015.
Extended European Search Report corresponding to Int'l Application. No. EP 11 25 0675.3 dated Oct. 7, 2015.
Extended European Search Report corresponding to Int'l Application. No. EP 11 25 0674.6 dated Oct. 7, 2015.
Extended European Search Report corresponding to Int'l Application. No. EP 12 19 3447.5 dated Oct. 19, 2015.
Canadian Office Action corresponding to Int'l Application No. CA 2,675,875 dated Oct. 26, 2015.
Japanese Office Action corresponding to Int'l Application No. JP 2015-005629 dated Oct. 28, 2015.
Japanese Office Action corresponding to Int'l Application No. JP 2014-245081 dated Oct. 28, 2015.
Canadian Office Action corresponding to Int'l Application No. CA 2,675,921 dated Oct. 30, 2015.
Chinese Office Action corresponding to Int'l Application No. CN 201210555570.8 dated Nov. 2, 2015.
Canadian Office Action corresponding to In'tl Application No. CA 2,676,309 dated Nov. 3, 2015.
Canadian Office Action corresponding to Int'l Application No. CA 2,676,211 dated Nov. 24, 2015.
Canadian Office Action corresponding to Int'l Application No. CA 2,676,547 dated Nov. 25, 2015.
Extended European Search Report corresponding to Int'l Application. No. EP 15 17 3809.3 dated Nov. 25, 2015.
Chinese Office Action corresponding to Int'l Application No. CN 201210586814.9 dated Dec. 2, 2015.
Extended European Search Report corresponding to Int'l Application. No. EP 12 17 2940.4 dated Dec. 14, 2015.
Chinese First Office Action corresponding to Int'l Appln. No. CN 201210586826.1 dated Dec. 30, 2015.
Extended European Search Report corresponding to Int'l Appln. No. EP 15 18 5362.9 dated Feb. 12, 2016.
Extended European Search Report corresponding to Int'l Appln. No. EP 12 19 7813.4 dated Mar. 7, 2016.
Canadian Office Action corresponding to Int'l Appln. No. CA 2,676,465 dated Mar. 8, 2016.
Japanese Office Action corresponding to Int'l Appln. No. JP 2014-245081 dated Mar. 18, 2016.
Japanese Office Action corresponding to Int'l Appln. No. JP 2015-005629 dated Mar. 18, 2016.
Extended European Search Report corresponding to Int'l Appln. No. EP 15 19 3549.1 dated Mar. 22, 2016.
International Search Report and Written Opinion corresponding to Int'l Appln. No. PCT/CN2015/082199 dated Mar. 31, 2016.

(56) References Cited

OTHER PUBLICATIONS

Extended European Search Report corresponding to Int'l Appln. No. EP 15 19 7251.0 dated Apr. 8, 2016.
Extended European Search Report corresponding to Int'l Appln. No. EP 16 15 0739.7 dated May 17, 2016.
Canadian Office Action corresponding to Int'l Appln. No. CA 2,716,672 dated May 31, 2016.
Canadian Office Action corresponding to Int'l Appln. No. CA 2,717,448 dated May 31, 2016.
Canadian Office Action corresponding to Int'l Appln. No. CA 2,721,951 dated Jun. 1, 2016.
Partial European Search Report corresponding to Int'l Appln. No. EP 16 15 0287.7 dated Jun. 16, 2016.
Chinese Second Office Action corresponding to Int'l Appln. No. CN 201210555570.8 dated Jun. 20, 2016.
Chinese First Office Action corresponding to Chinese Appln. No. CN 201410076318.8 dated Jan. 23, 2017.
Extended European Search Report corresponding to European Appln. No. EP 16 18 3184.7 dated Jan. 24, 2017.
Japanese Office Action corresponding to Japanese Appln. No. JP 2016-097807 dated Feb. 14, 2017.
European Office Action corresponding to European Appln. No. EP 12 19 3447.5 dated Apr. 4, 2017.
Chinese First Office Action corresponding to Chinese Appln. No. CN 201410008877.5 dated Apr. 6, 2017.
Extended European Search Report corresponding to European Appln. No. EP 17 15 3714.5 dated May 11, 2017.
Extended European Search Report corresponding to European Appln. No. EP 17 15 8519.3 dated May 19, 2017.
Extended European Search Report corresponding to European Appln. No. EP 17 15 7606.9 dated May 22, 2017.
European Office Action corresponding to European Appln. No. EP 11 25 0674.6 dated May 23, 2017.
Canadian Office Action corresponding to Canadian Appln. No. CA 2,743,402 dated May 30, 2017.
European Office Action corresponding to European Appln. No. EP 16 15 9324.9 dated Aug. 7, 2017.
Extended European Search Report corresponding to Patent Application EP 18154617.7 dated Jun. 25, 2018.
Extended European Search Report corresponding to Patent Application EP 18155158.1 dated Jun. 28, 2018.
Extended European Search Report corresponding to Patent Application EP 15877428.1 dated Jul. 2, 2018.
Extended European Search Report corresponding to Patent Application EP 18157789.1 dated Jul. 5, 2018.
Canadian Office Action corresponding to Patent Application CA 2,972,444 dated Aug. 9, 2018.
Extended European Search Report corresponding to Patent Application EP 18156458.4 dated Sep. 3, 2018.
Extended European Search Report corresponding to Patent Application EP 18171682.0 dated Sep. 18, 2018.
Extended European Search Report corresponding to Patent Application EP 15878354.8 dated Sep. 19, 2018.
Extended European Search Report corresponding to Patent Application EP 18183394.8 dated Sep. 28, 2018.
Extended European Search Report corresponding to Patent Application EP 18163041.9 dated Sep. 28, 2018.
Extended European Search Report corresponding to Patent Application EP 18170524.5 dated Oct. 1, 2018.
Japanese Office Action corresponding to Patent Application JP 2017-536546 dated Oct. 15, 2018.
Extended European Search Report corresponding to Patent Application EP 18187640.0 dated Nov. 30, 2018.
Extended European Search Report corresponding to Patent Application EP 18187690.5 dated Nov. 30, 2018.
Chinese First Office Action corresponding to Patent Application CN 201510696298.9 dated Dec. 3, 2018.
Extended European Search Report corresponding to Patent Application EP 18158143.0 dated Dec. 5, 2018.
International Search Report corresponding to Int'l Patent Appln. PCT/US2018/050316 dated Dec. 31, 2018.
International Search Report corresponding to Int'l Patent Appln. PCT/US2018/050336 dated Jan. 7, 2019.
International Search Report corresponding to Int'l Patent Appln. PCT/US2018/050325 dated Jan. 7, 2019.
International Search Report corresponding to Int'l Patent Appln. PCT/US2018/045306 dated Jan. 16, 2019.
International Search Report corresponding to Int'l Patent Appln. PCT/US2018/050349 dated Jan. 21, 2019.
International Search Report corresponding to Int'l Patent Appln. PCT/US2018/045725 dated Jan. 28, 2019.
Extended European Search Report corresponding to European Patent Application EP 18208630.6 dated Feb. 12, 2019.
International Search Report corresponding to Int'l Patent Appln. PCT/US2018/057910 dated Feb. 22, 2019.
International Search Report corresponding to Int'l Patent Appln. PCT/US2018/057922 dated Feb. 22, 2019.
International Search Report corresponding to Int'l Patent Appln. PCT/US2018/058078 dated Feb. 22, 2019.
International Search Report corresponding to Int'l Patent Appln. PCT/US2018/058603 dated Feb. 22, 2019.
International Search Report corresponding to Int'l Patent Appln. PCT/US2018/057221 dated Mar. 11, 2019.
Extended European Search Report corresponding to European Patent Application EP 18212043.6 dated Apr. 24, 2019.
Extended European Search Report corresponding to European Patent Application EP 18211565.9 dated Apr. 26, 2019.
Extended European Search Report corresponding to European Patent Application EP 18211921.4 dated Apr. 30, 2019.
Chinese First Office Action corresponding to Chinese Patent Application CN 201510868226.8 dated May 29, 2019.
Extended European Search Report corresponding to European Patent Application EP 15905685.2 dated May 29, 2019.
European Office Action corresponding to European Patent Application EP 17157606.9 dated Jul. 2, 2019.
Extended European Search Report corresponding to European Patent Application EP 15908025.8 dated Jul. 2, 2019.
Extended European Search Report corresponding to European Patent Application EP 18212054.3 dated Jul. 3, 2019.
Japanese Office Action dated Oct. 17, 2019 corresponding to counterpart Patent Application JP 2018-534822.
Extended European Search Report dated Oct. 31, 2019 corresponding to counterpart Patent Application EP 16884297.9.
Chinese First Office Action dated Jul. 28, 2020 corresponding to counterpart Patent Application CN 201680078525.4.
International Search Report for PCT/CN2016/070571 date of completion is Sep. 6, 2016 (2 pages).
Chinese First Office Action corresponding to Chinese Appln. No. CN 2014104295806 dated Aug. 31, 2017.
Extended European Search Report corresponding to European Appln. No. EP 17 17 3508.7 dated Sep. 29, 2017.
Chinese Second Office Action corresponding to Chinese Appln. No. CN 201410076318.8 dated Oct. 10, 2017.
Extended European Search Report corresponding to European Appln. No. Ep 17 18 0570.8 dated Dec. 6, 2017.
Partial Supplementary European Search Report dated Jul. 30, 2019 issued in corresponding EP Appln. No. 16884297.9.
The extended European Search Report corresponding to European Application No. EP 07 25 3905.9, completed Jan. 29, 2008; dated Feb. 7, 2008; (7 Pages).
International Search Report corresponding to International Application No. PCT-US08-58185, completed Sep. 4, 2008; dated Sep. 9, 2008; (2 Pages).
The International Search Report corresponding to International Application No. PCT-US08-59859, completed Sep. 14, 2008; dated Sep. 18, 2008; (2 Pages).
The extended European Search Report corresponding to European Application No. EP 07 25 3807.7, completed Nov. 7, 2008; dated Nov. 26, 2008; (11 Pages).
The extended European Search Report corresponding to European Application No. EP 09 25 2049.3, completed Dec. 11, 2009; dated Jan. 12, 2010; (3 Pages).

(56) References Cited

OTHER PUBLICATIONS

The extended European Search Report corresponding to European Application No. EP 09 25 2050.1, completed Dec. 23, 2009; dated Jan. 21, 2010; (3 Pages).
The extended European Search Report corresponding to European Application No. EP 09 25 2051.9, completed Dec. 21, 2009; dated Jan. 28, 2010; (3 Pages).
The extended European Search Report corresponding to European Application No. EP 09 25 2052.7, ,completed Nov. 16, 2009; dated Nov. 24, 2009; (3 Pages).
The extended European Search Report corresponding to European Application No. EP 09 25 2053.5, completed Nov. 24, 2009; dated Dec. 1, 2009; (3 Pages).
The extended European Search Report corresponding to European Application No. EP 09 25 2054.3, completed Jan. 7, 2010; dated Jan. 22, 2010; (3 Pages).
The extended European Search Report corresponding to European Application No. EP 09 25 2056.8, completed Jan. 8, 2010; dated Feb. 5, 2010; (3 Pages).
The extended European Search Report corresponding to European Application No. EP 10 25 0497.4, completed May 4, 2010; dated May 12, 2010; (6 Pages).
The extended European Search Report corresponding to European Application No. EP 10 25 2079.8, completed Mar. 8, 2011; dated Mar. 17, 2011; (3 Pages).
The European Search Report corresponding to European Application No. EP 05 81 0218.7, completed Apr. 18, 2011; dated May 20, 2011; (3 pages).
The European Search Report corresponding to European Application No. EP 05 80 7612.6, completed May 2, 2011; dated May 20, 2011; (3 pages).
The extended European Search Report corresponding to European Application No. EP 10 25 1737.2, completed May 9, 2011; dated May 20, 2011; (4 pages).
The extended European Search Report corresponding to European Application No. EP 11 25 0214.1, completed May 25, 2011; dated Jun. 1, 2011; (3 Pages).
The extended European Search Report corresponding to European Application No. EP 11 00 2681.2, completed May 31, 2011; dated Jun. 10, 2011; (3 Pages).
The European Search Report corresponding to European Application No. EP 05 80 26865, completed Jan. 9, 2012; dated Jan. 18, 2012; (3 Pages).
The extended European Search Report corresponding to European Application No. EP 12 15 1313.9, completed Mar. 20, 2012 and dated Apr. 12, 2012; (5 Pages).
The extended European Search Report corresponding to European Application No. EP 12 16 1291.5, completed Apr. 24, 2012 and dated May 4, 2012; (5 Pages).
The extended European Search Report corresponding to European Application No. EP 12 16 5891.8, completed Jun. 12, 2012 and dated Jun. 20, 2012; (6 Pages).
The extended European Search Report corresponding to European Application No. EP 12 16 2288.0, completed Jun. 4, 2012 and dated Jul. 7, 2012; (6 Pages).
The extended European Search Report corresponding to European Application No. EP 12 16 4955.2, completed Aug. 23, 2012 and dated Sep. 4, 2012; (5 Pages).
The extended European Search Report corresponding to European Application No. EP 11 25 0754.6, completed Oct. 22, 2012 and dated Oct. 31, 2012; (6 Pages).
The extended European Search Report corresponding to European Application No. EP 12 18 6401.1, completed Nov. 22, 2012 and dated Nov. 30, 2012; (7 Pages).
The extended European Search Report corresponding to European Application No. EP 12 18 6448.2, completed Nov. 28, 2012 and dated Dec. 10, 2012; (6 Pages).
The extended European Search Report corresponding to European Application No. EP 12 19 1706.6, completed Dec. 19, 2012 and dated Jan. 8, 2013; (6 Pages).
The Extended European Search Report corresponding to EP 12 19 8745.7, completed Mar. 19, 2013 and dated Apr. 11, 2013; (8 Pages).
The Extended European Search Report corresponding to EP 12 15 2989.5, completed Apr. 9, 2013 and dated Apr. 18, 2013; (9 Pages).
The Extended European Search Report corresponding to EP 08 73 2820.9, completed Jul. 2, 2013 and dated Jul. 9, 2013; (10 Pages).
The Extended European Search Report corresponding to EP 13 17 2008.8, completed Aug. 14, 2013 and dated Aug. 28, 2013; (8 Pages).
The Extended European Search Report corresponding to EP 13 16 6382.5, completed Nov. 19, 2013 and dated Nov. 28, 2013; (8 Pages).
The Extended European Search Report corresponding to EP 11 25 0194.5, completed Nov. 25, 2013 and dated Dec. 3, 2013; (8 Pages).
The Extended European Search Report corresponding to EP 10 25 1798.4, completed Dec. 12, 2013 and dated Jan. 2, 2014; (9 Pages).
"Salute II Disposable Fixation Device", Technique Guide—Laparoscopic and Open Inguinal and Ventral Hernia Repair; Davol, A Bard Company, 2006; (7 Pages).
The Extended European Search Report corresponding to EP 10 25 2112.7, completed Jul. 29, 2014 and dated Aug. 5, 2014; (8 pp).
The Extended European Search Report corresponding to EP 14 15 1673.2, completed Apr. 25, 2014 and dated May 8, 2014; (8 pp).
Japanese Office Action corresponding to JP 2011-160130 dated Dec. 1, 2014.
Chinese Office Action corresponding to CN 201210015011.8 dated Jan. 4, 2015.
Japanese Office Action corresponding to JP 2011-160126 dated Jan. 9, 2015.
Japanese Office Action corresponding to JP 2011-184521 dated Jan. 15, 2015.
Extended European Search Report corresponding to 14 18 2236.1 dated Jan. 20, 2015.
Chinese Office Action corresponding to CN 201110201736.1 dated Feb. 9, 2015.
Extended European Search Report corresponding to EP 14 16 1540.1 dated Feb. 27, 2015.
Australian Office Action corresponding to AU 2010226985 dated Mar. 31, 2015.
Australian Office Action corresponding to AU 2013211526 dated Apr. 6, 2015.
Australian Office Action corresponding to AU 2011211463 dated Apr. 13, 2015.
Australian Office Action corresponding to AU 2013254887 dated Apr. 14, 2015.
Japanese Office Action corresponding to JP 2013-225272 dated May 1, 2015.

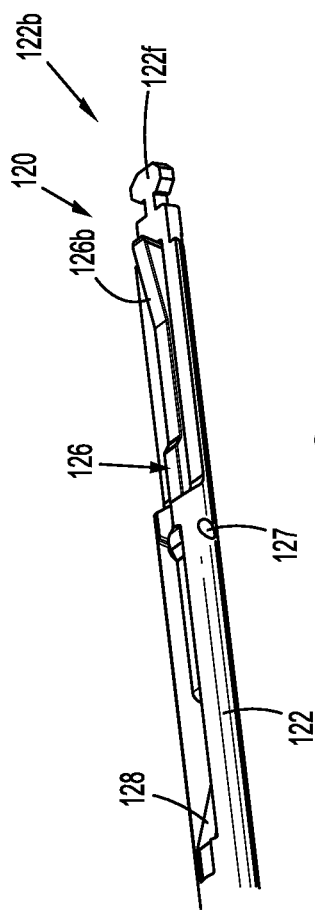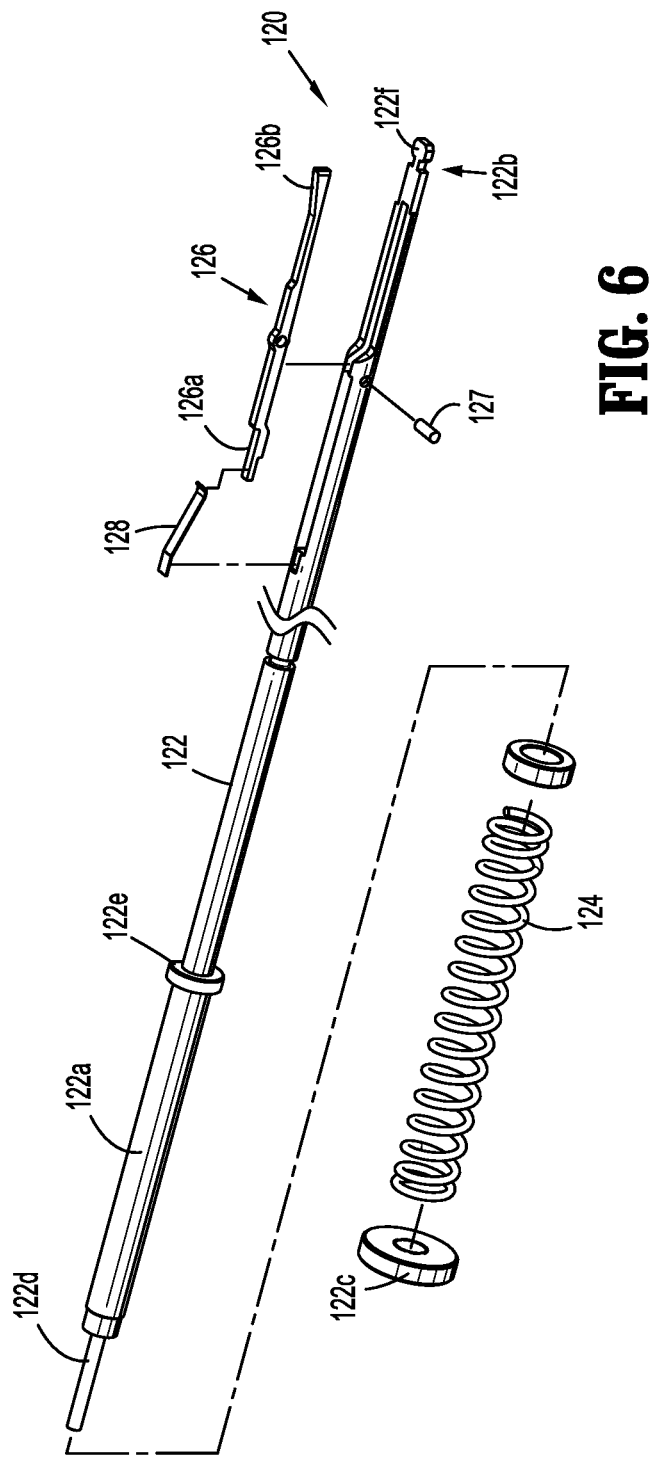

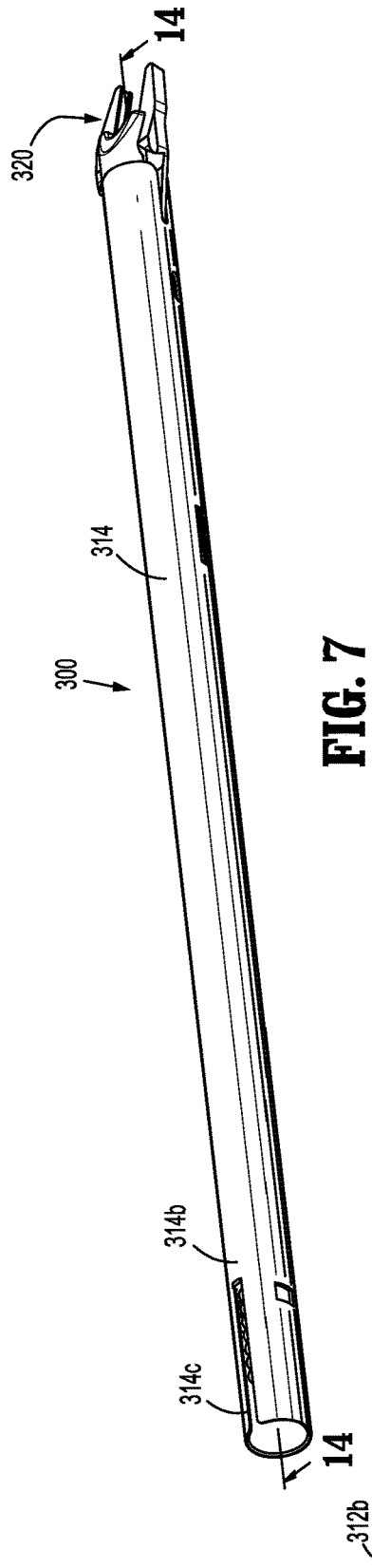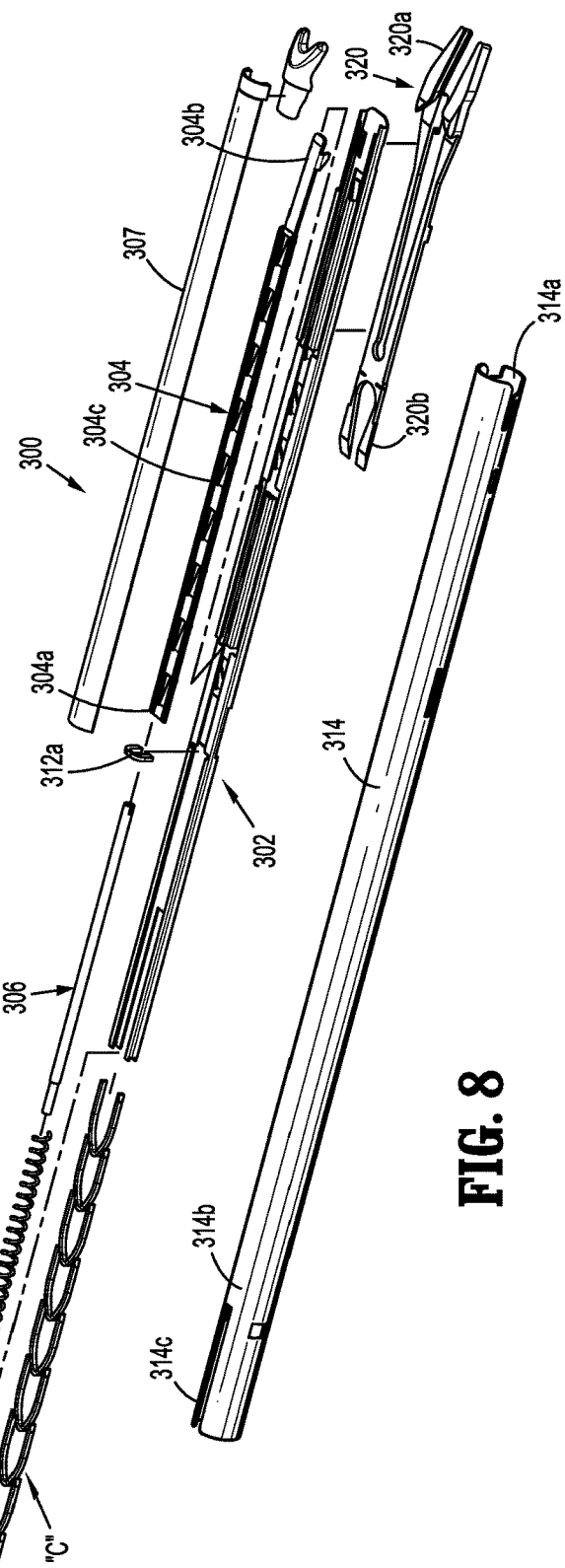
FIG. 7
FIG. 8

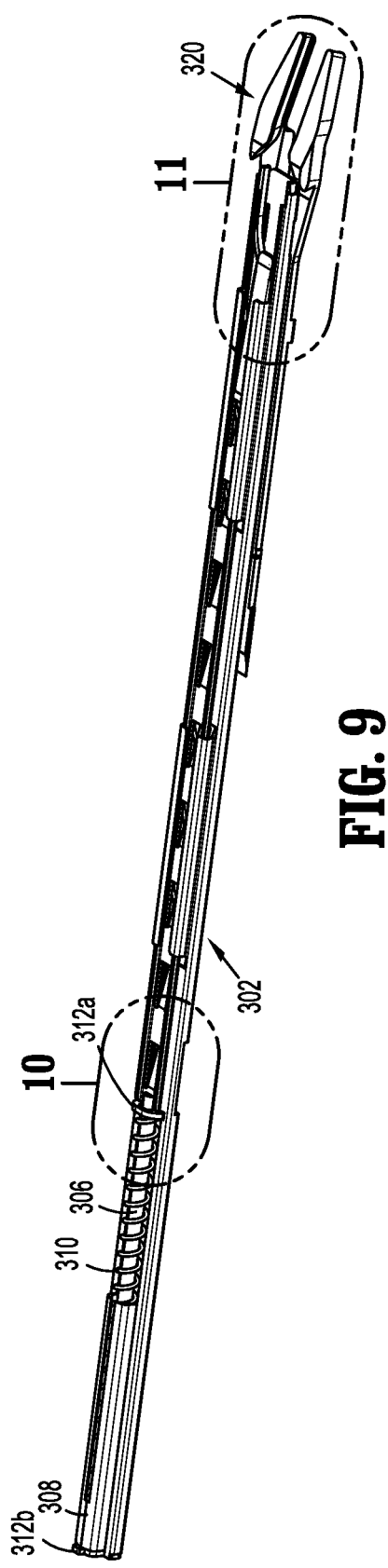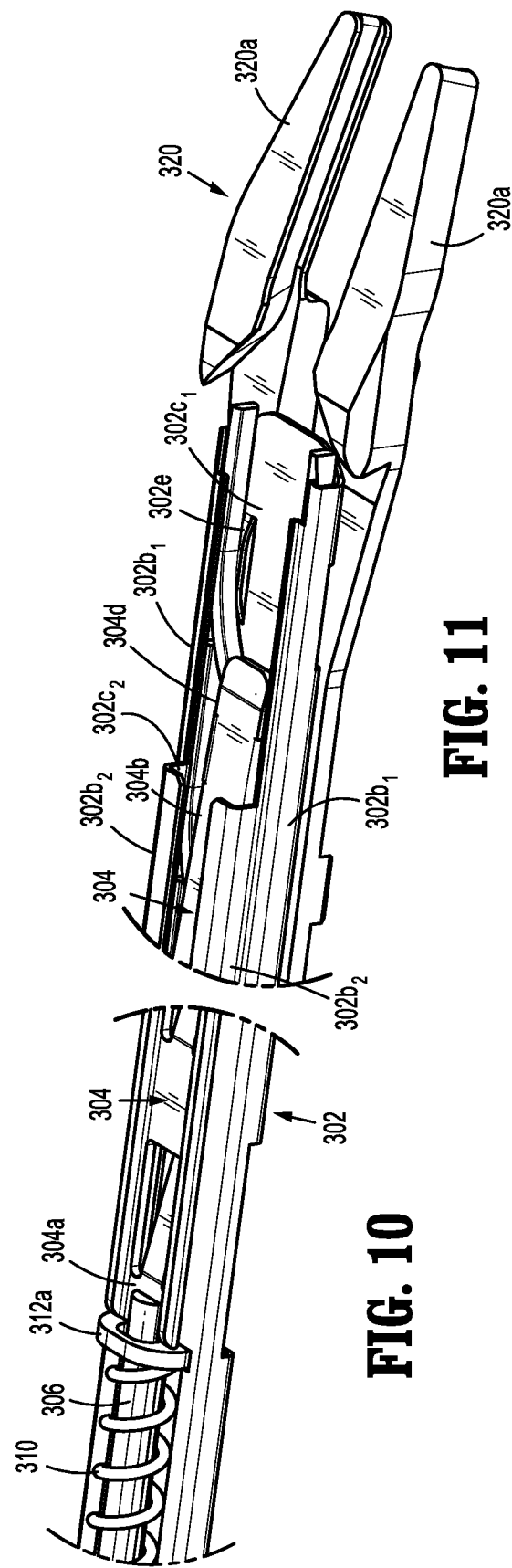
FIG. 9
FIG. 10
FIG. 11

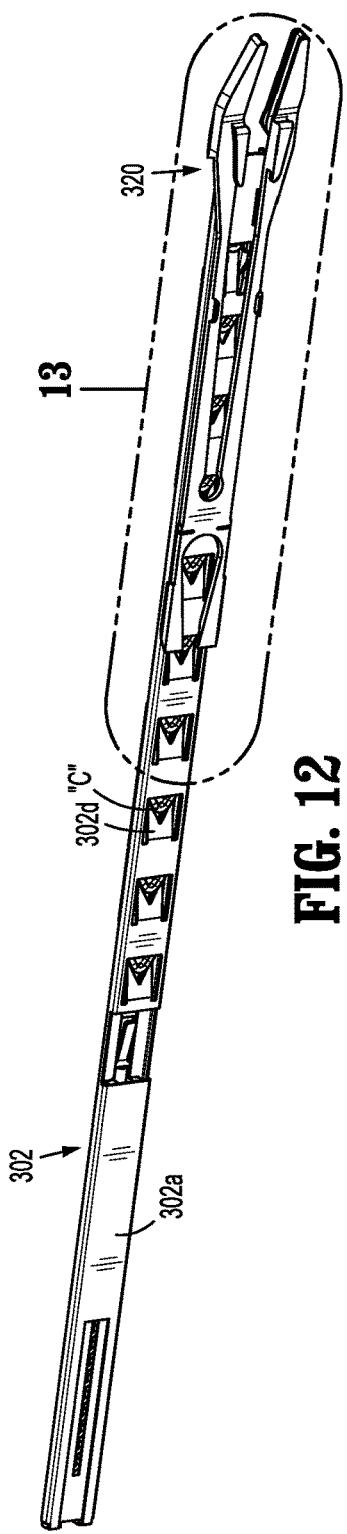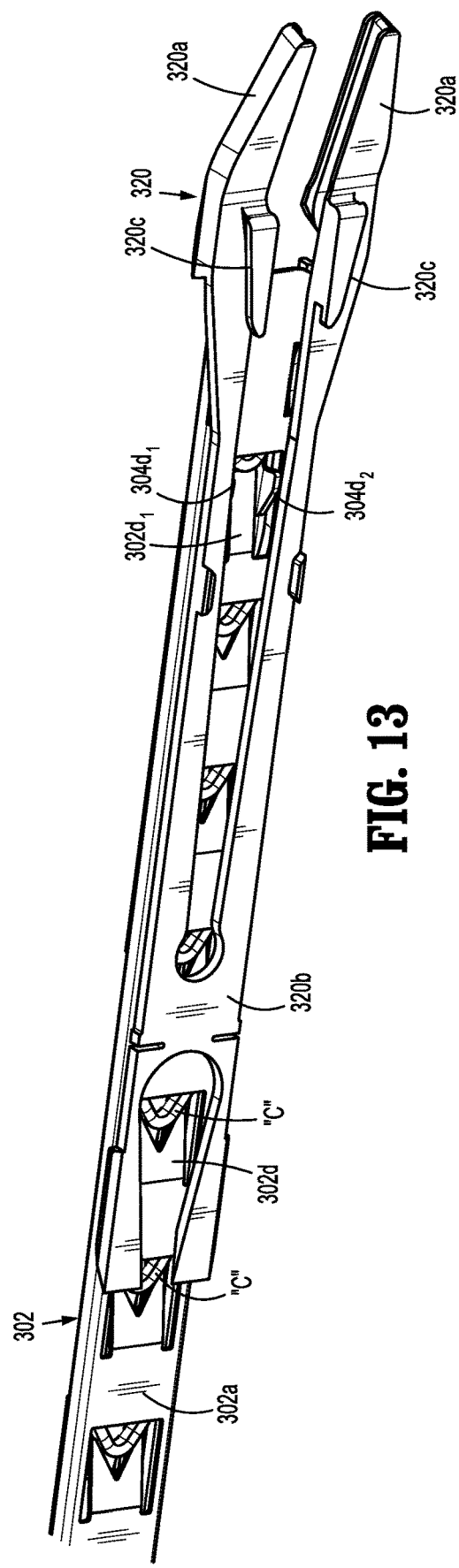
FIG. 12
FIG. 13

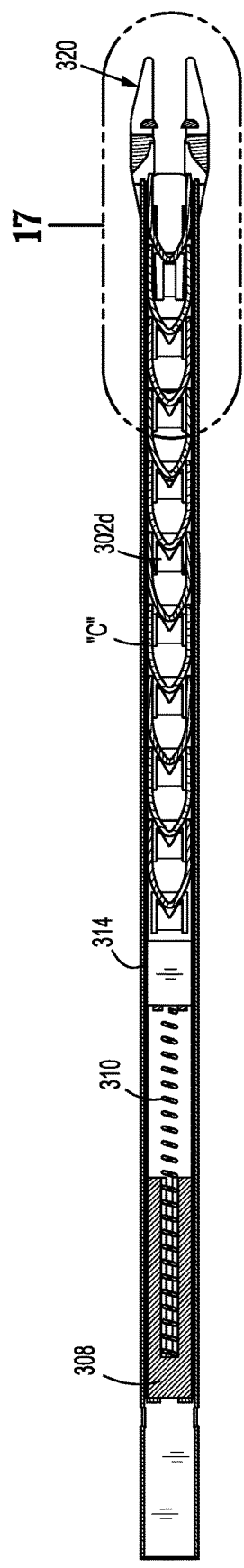
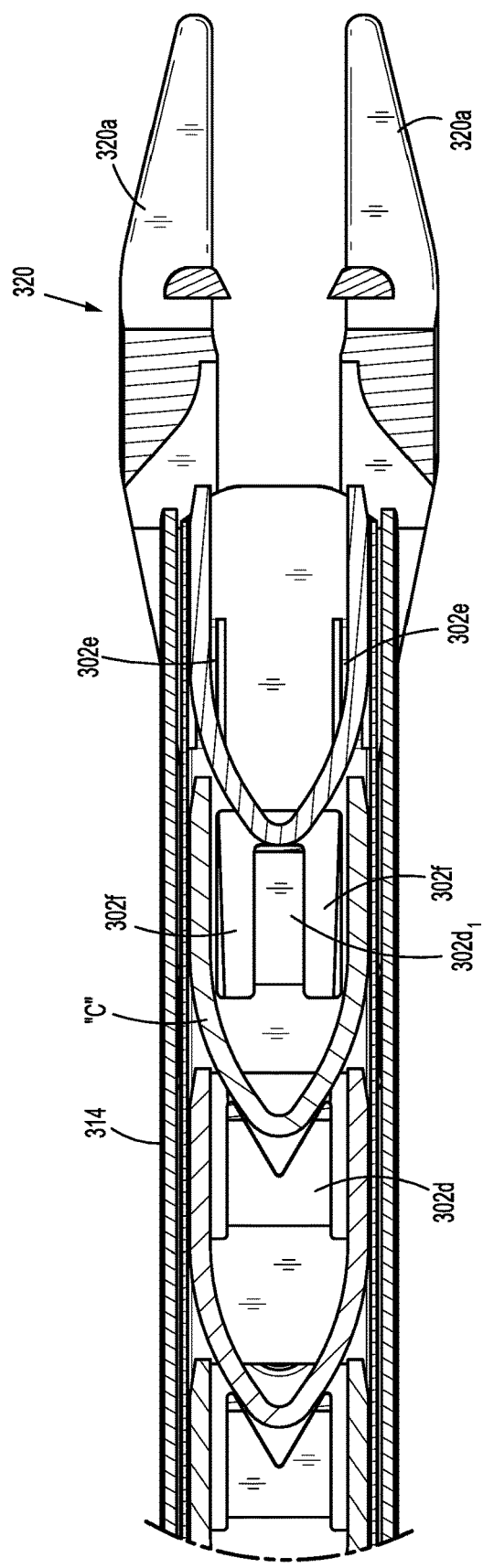
FIG. 16
FIG. 17

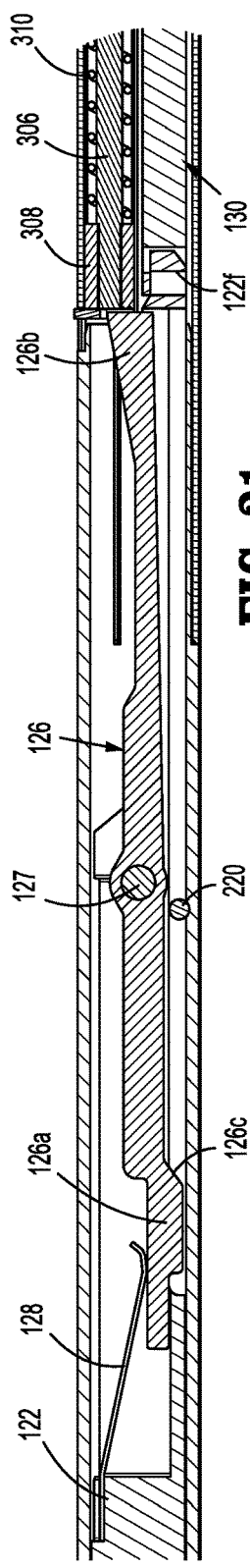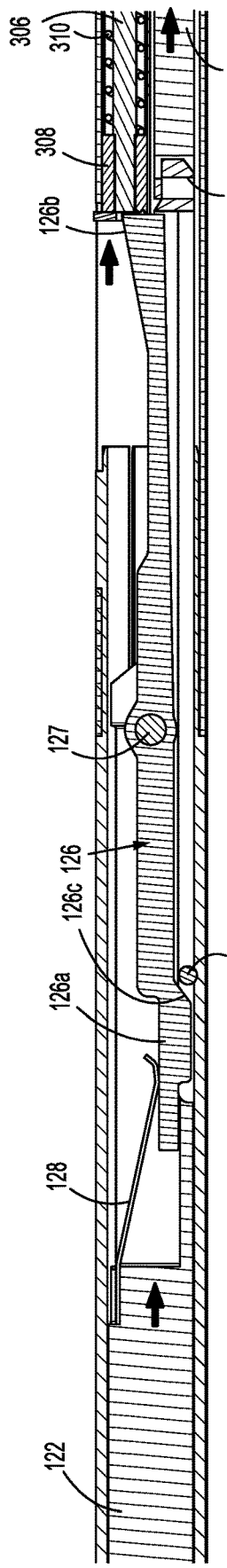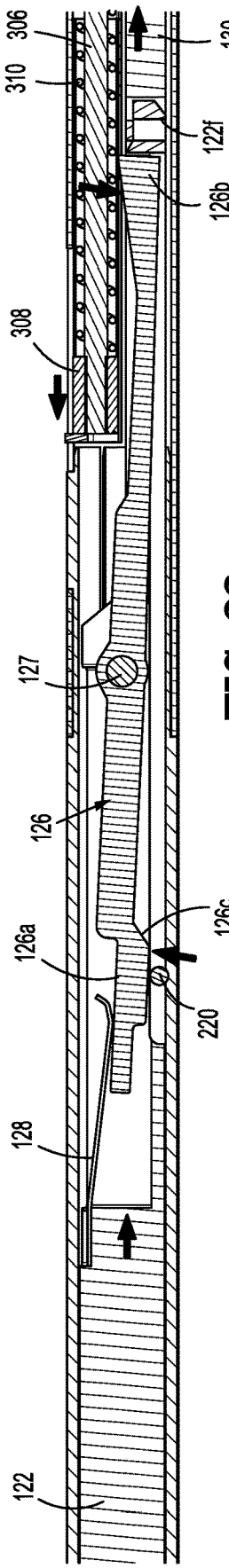

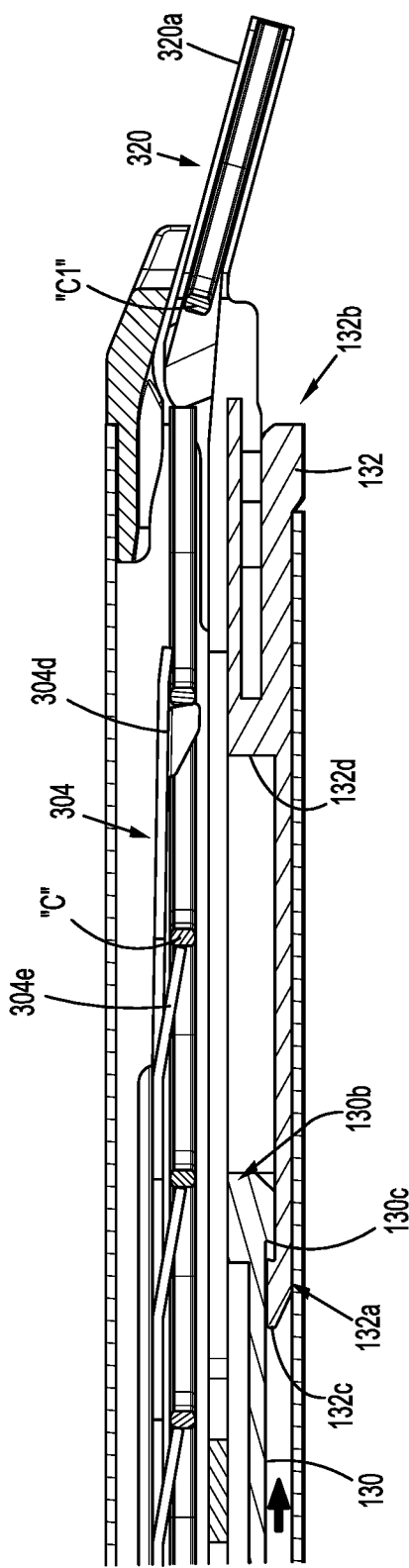
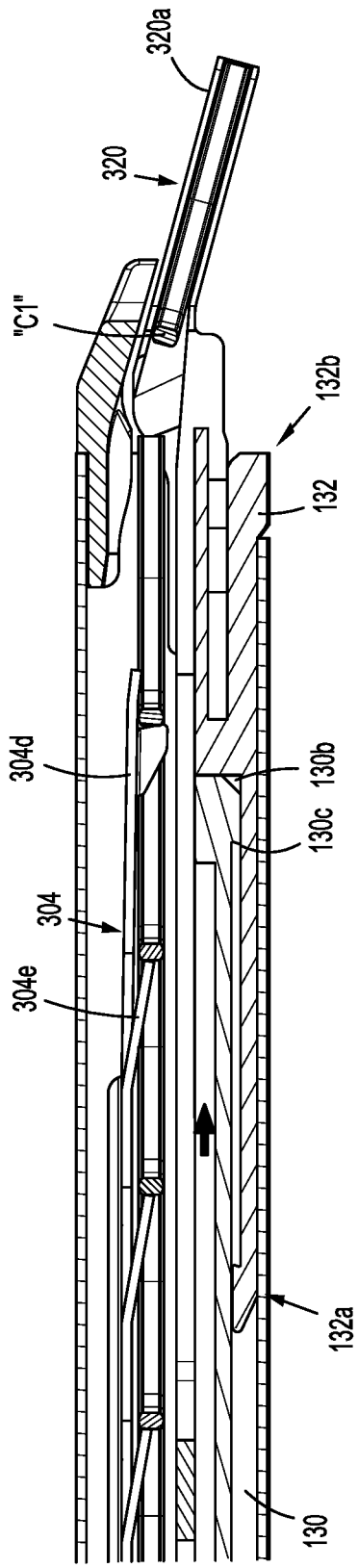
FIG. 34
FIG. 35

ENDOSCOPIC REPOSABLE SURGICAL CLIP APPLIER

CROSS-REFERENCE TO RELATED APPLICATIONS

This application is a National Stage Application of PCT/CN2016/070571 under 35 USC § 371 (a), the disclosure of the above-identified application is hereby incorporated by reference in its entirety.

BACKGROUND

Technical Field

This disclosure relates to surgical clip appliers. More particularly, the present disclosure relates to endoscopic reposable surgical clip appliers having a reusable handle assembly, a reusable shaft assembly, and a disposable clip cartridge assembly.

Description of Related Art

Endoscopic staplers and clip appliers are known in the art and are used for a number of distinct and useful surgical procedures. In the case of a laparoscopic surgical procedure, access to the interior of an abdomen is achieved through narrow tubes or cannulas inserted through a small entrance incision in the skin. Minimally invasive procedures performed elsewhere in the body are often generally referred to as endoscopic procedures. Typically, a tube or cannula device is extended into the patient's body through the entrance incision to provide an access port. The port allows the surgeon to insert a number of different surgical instruments therethrough using a trocar and for performing surgical procedures far removed from the incision.

During a majority of these procedures, the surgeon must often terminate the flow of blood or another fluid through one or more vessels. The surgeon will often apply a surgical clip to a blood vessel or another duct to prevent the flow of body fluids therethrough during the procedure. An endoscopic clip applier is known in the art for applying a single clip during an entry to the body cavity. Such clips are typically fabricated from a biocompatible material and are usually compressed over a vessel. Once applied to the vessel, the compressed clip terminates the flow of fluid therethrough.

Endoscopic clip appliers that are able to apply multiple clips in endoscopic or laparoscopic procedures during a single entry into the body cavity are described in commonly-assigned U.S. Pat. Nos. 5,084,057 and 5,100,420 to Green et al., which are both incorporated by reference in their entirety. Another multiple endoscopic clip applier is disclosed in commonly-assigned U.S. Pat. No. 5,607,436 by Pratt et al., the contents of which are also hereby incorporated by reference herein in its entirety. These devices are typically, though not necessarily, used during a single surgical procedure. U.S. Pat. No. 5,695,502 to Pier et al., the disclosure of which is hereby incorporated by reference herein, discloses a resterilizable surgical clip applier. The clip applier advances and forms multiple clips during a single insertion into the body cavity. This resterilizable clip applier is configured to receive and cooperate with an interchangeable clip magazine so as to advance and form multiple clips during a single entry into a body cavity.

During endoscopic or laparoscopic procedures it may be desirable and/or necessary to use different size surgical clips depending on the underlying tissue or vessels to be ligated. In order to reduce overall costs of a surgical clip applier, it is desirable for a single surgical clip applier to be loadable with and capable of firing different size surgical clips as needed.

Accordingly, a need exists for endoscopic surgical clip appliers that include reusable handle assemblies, reusable shaft assemblies, and disposable clip cartridge assemblies, with each clip cartridge assembly being loaded with a particularly sized clip (e.g., relatively small, relatively medium, or relatively large).

SUMMARY

The present disclosure relates to reposable endoscopic surgical clip appliers.

According to an aspect of the present disclosure, a reposable surgical clip applier is provided and includes a handle assembly, an outer tube assembly, and a clip cartridge assembly. The handle assembly includes a fixed handle, a trigger, and a drive assembly removably supported within the housing and operatively actuatable by the trigger. The drive assembly includes a drive rod having a proximal end and a distal end.

The outer tube assembly is disposed on a distal end of the housing and extends distally therefrom.

The clip cartridge assembly is selectively connectable to the distal end of the outer tube assembly and includes an outer tube, a pair of jaws fixedly supported in a distal end of the outer tube, a first jaw pusher in selective engagement with the distal end of the drive rod, a second jaw pusher, and a plurality of surgical clips disposed within the outer tube. A proximal end of the second jaw pusher is in selective engagement with the first jaw pusher and a distal end of the second jaw pusher is in selective engagement with the pair of jaws.

The distal end of the drive rod may define a tab extending therefrom.

The proximal end of the first jaw pusher may include a pocket defined therein configured to selectively engage the tab of the drive rod.

The outer tube of the clip cartridge assembly may further include a pair of windows defined therein configured to receive a corresponding pair of tabs extending from each side of the first jaw pusher. The pair of tabs of the first jaw pusher may be received within the corresponding pair of windows of the outer tube. The pocket of the first jaw pusher may be permitted to receive the tab of the drive rod.

Actuation of the trigger may cause distal movement of the drive rod and the first jaw pusher. Continued actuation of the trigger may cause a distal end of the first jaw pusher to abut a proximal surface of the second jaw pusher, thereby urging the second jaw pusher in a distal direction.

The second jaw pusher may include a barb defined on a proximal end thereof.

The first jaw pusher may include a barb defined on a distal end thereof. The barb of the first jaw pusher may be configured to engage the barb of the second jaw pusher as the first jaw pusher travels in a proximal direction.

The housing of the handle assembly may be a hollow barrel housing having the fixed handle extending therefrom. The barrel housing may define a bore therethrough, an open proximal end, and an open distal end. The trigger may be pivotally supported on and extend from the barrel housing. The trigger may include an actuating end extending into the bore of the barrel housing.

The reposable surgical clip applier may further include an end cap including a bore defined therein. The end cap may be configured to be received within the open proximal end of the bore of the housing.

The drive rod may include an elongate extension extending from a proximal end thereof and extending in a proximal direction therefrom. The elongate extension may be configured to be slidably received within the bore of the threaded cap.

The trigger of the handle assembly may include an actuating end disposed proximal of the drive rod and in operative contact with the drive rod.

The trigger of the handle assembly may be pivotable to a position wherein the actuating end of the trigger is not within the bore of the barrel housing.

In use, when the actuating end of the trigger is not within the bore of the barrel housing, the distal end of the drive assembly may be insertable into the proximal end of the barrel housing and advanceable through the barrel housing and through the outer tube assembly.

The outer tube assembly may include a knob supporting the outer tube thereof. The barrel housing of the handle assembly and the knob of the outer tube assembly may be selectively connectable to one another via a bayonet-type connection.

A proximal end of the clip cartridge assembly may be selectively connectable to the outer tube assembly via a snap-fit connection.

According to another aspect of the present disclosure, a method of assembling a reposable surgical clip applier is provided and includes advancing a drive assembly within a handle assembly that includes a housing, a fixed handle, and a trigger. The method further includes advancing a distal end of an outer tube disposed on a distal end of the handle assembly within an outer tube of a cartridge assembly. The method also includes advancing a tab disposed on a distal end of a drive rod of the drive assembly within a pocket defined within a proximal end of the first jaw pusher disposed within the outer tube of the cartridge assembly. The method further includes advancing an end cap over an elongate extension disposed on a proximal end of the drive rod and advancing the end cap within a bore defined within a proximal end of the housing of the handle assembly. In use, advancing the end cap within the bore urges the drive rod in a distal direction such that distal movement of the drive rod in turn urges the first jaw pusher in a distal direction, thereby capturing the tab of the drive rod within the pocket of the first jaw pusher such that the drive rod and the jaw member may be advanced or retreated in unison.

In use, advancing the distal end of an outer tube of a handle assembly within an outer tube of the cartridge assembly may include advancing the distal end of the outer tube of the handle assembly within the outer tube of the cartridge assembly until the cartridge assembly is frictionally retained within the outer tube of the handle assembly.

In use, continuing to advance the distal end of the outer tube of the handle assembly may include advancing the outer tube of the handle assembly within the outer tube of the cartridge assembly until the cartridge assembly is retained within the outer tube of the handle assembly by means of a snap-fit connection.

In use, advancing the end cap within a bore defined within a proximal end of the housing of the handle assembly may cause pair of tabs disposed on each side of the first jaw pusher to become dislodged from a corresponding pair of windows disposed in the outer tube of the cartridge assembly, thereby causing the pocket of the first jaw member to retain the tab of the drive rod therein.

The method may further include rotating the trigger such that an actuating end of the trigger is not within the bore of the housing assembly before advancing the drive assembly therein.

BRIEF DESCRIPTION OF THE DRAWINGS

A particular embodiment of a surgical clip applier is disclosed herein with reference to the drawings wherein:

FIG. 5 is a perspective view of a main shaft assembly of the handle assembly of FIGS. 1 and 2;

FIG. 6 is a perspective view, with parts separated, of the main shaft assembly of FIG. 5;

FIG. 7 is a rear, perspective view of a disposable clip cartridge assembly according to an embodiment of the present disclosure;

FIG. 8 is a perspective view, with parts separated, of the disposable clip cartridge assembly of FIG. 7;

FIG. 9 is a perspective view of the disposable clip cartridge assembly of FIGS. 7 and 8, with an outer tube thereof removed;

FIG. 10 is an enlarged view of the indicated area of detail of FIG. 9;

FIG. 11 is a perspective view of the indicated area of detail of FIG. 9;

FIG. 12 is a bottom, perspective view of the disposable clip cartridge assembly of FIGS. 7-11, with an outer tube and cartridge clip tray thereof removed;

FIG. 13 is an enlarged view of the indicated area of detail of FIG. 12;

FIG. 16 is a cross-sectional view of the disposable clip cartridge assembly of FIGS. 7-15, as taken along section line 16-16 of FIG. 14, with a clip pusher bar thereof removed;

FIG. 17 is an enlarged view of the indicated area of detail of FIG. 16;

FIGS. 31-33 are side, cross-sectional, elevational views of the disposable clip cartridge assembly and the outer tube assembly of the reposable endoscopic surgical clip applier, illustrating an actuation of the main shaft during the squeezing of the trigger;

FIGS. 34 and 35 are side, cross-sectional, elevational views the disposable clip cartridge assembly, illustrating an actuation of the cartridge clip pusher bar;

DETAILED DESCRIPTION OF EMBODIMENTS

Figure 1:
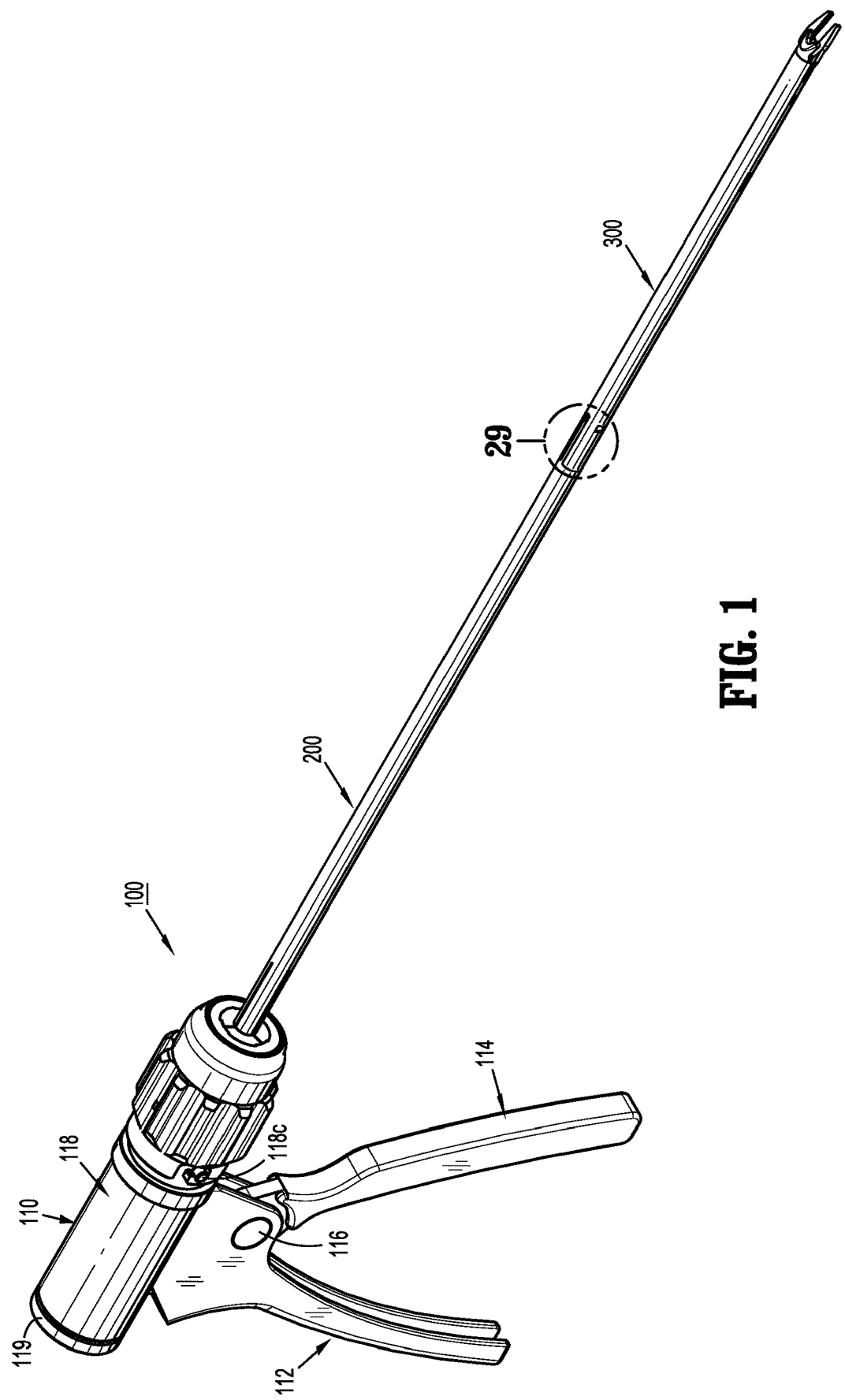
FIG. 1 is a top, front, perspective view, of a reposable endoscopic surgical clip applier, according to the present disclosure.

Embodiments of reposable surgical clip appliers, in accordance with the present disclosure, will now be described in detail with reference to the drawing figures wherein like reference numerals identify similar or identical structural elements. As shown in the drawings and described throughout the following description, as is traditional when referring to relative positioning on a surgical instrument, the term "proximal" refers to the end of the apparatus which is closer to the user and the term "distal" refers to the end of the apparatus which is further away from the user.

Figure 2:
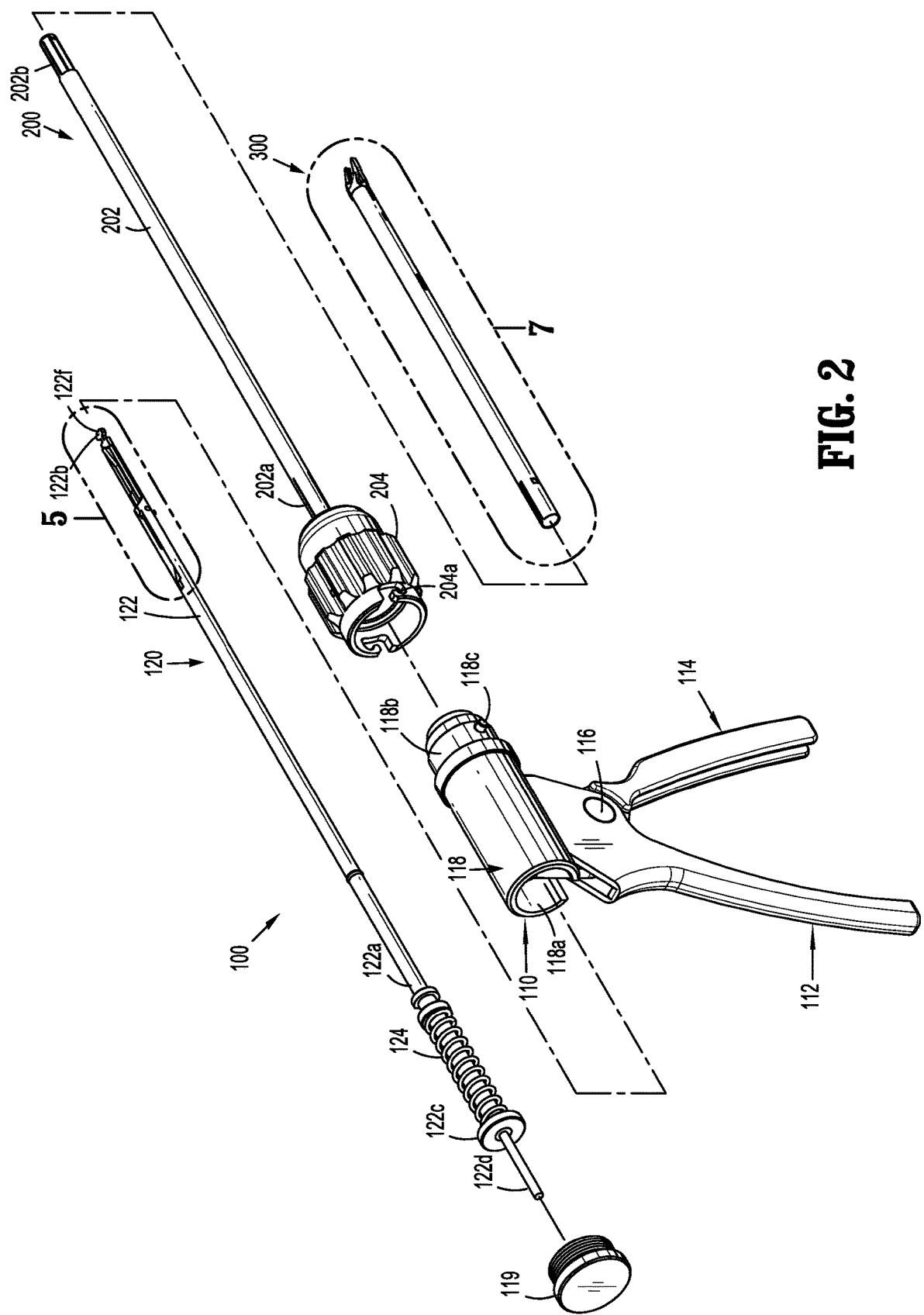
FIG. 2 is a rear, perspective view, with parts separated, of the reposable endoscopic surgical clip applier of FIG. 1.
Figure 3:
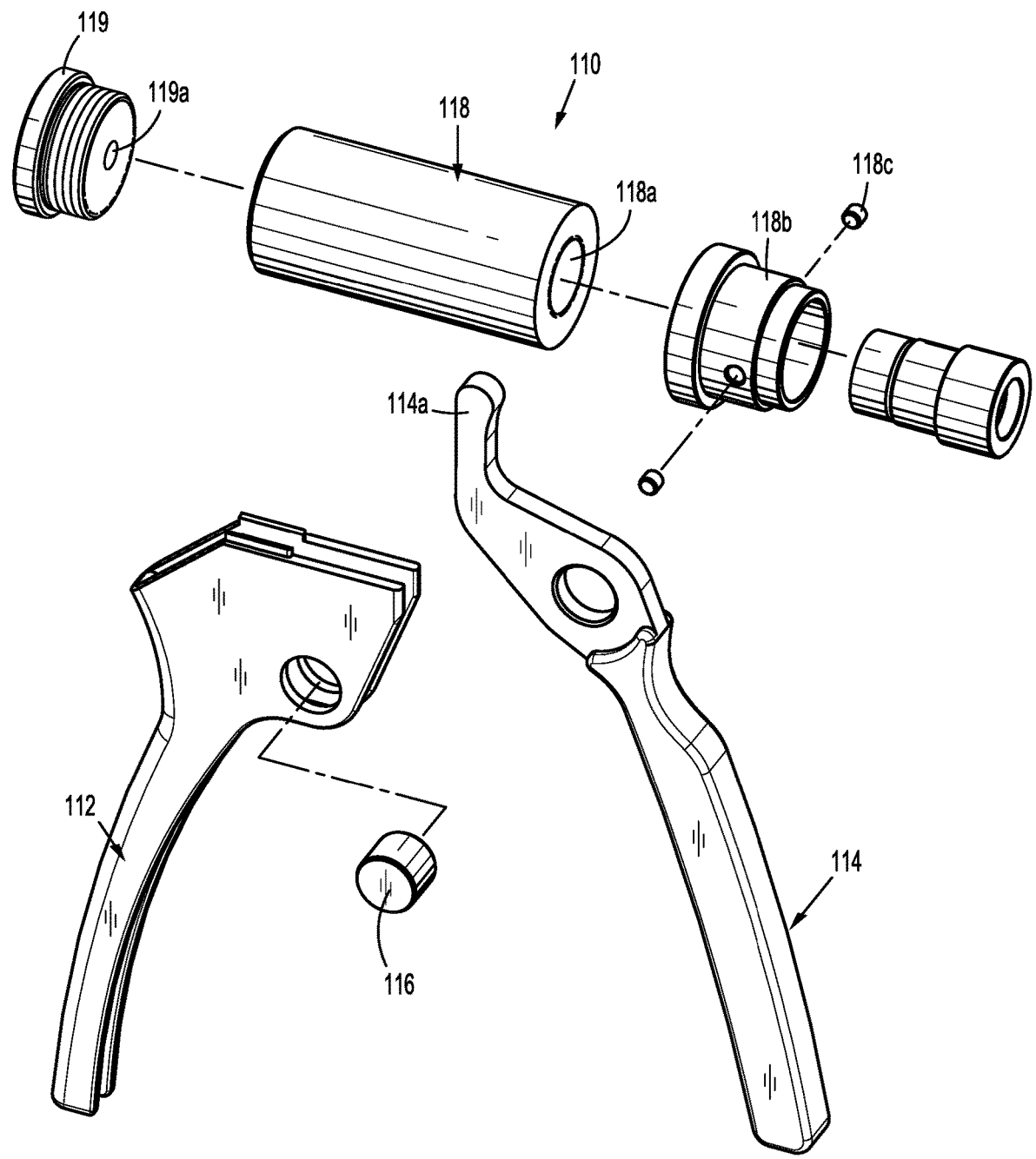
FIG. 3 is a perspective view, with parts separated, of a handle assembly of the reposable endoscopic surgical clip applier of FIGS. 1 and 2.
Figure 4:
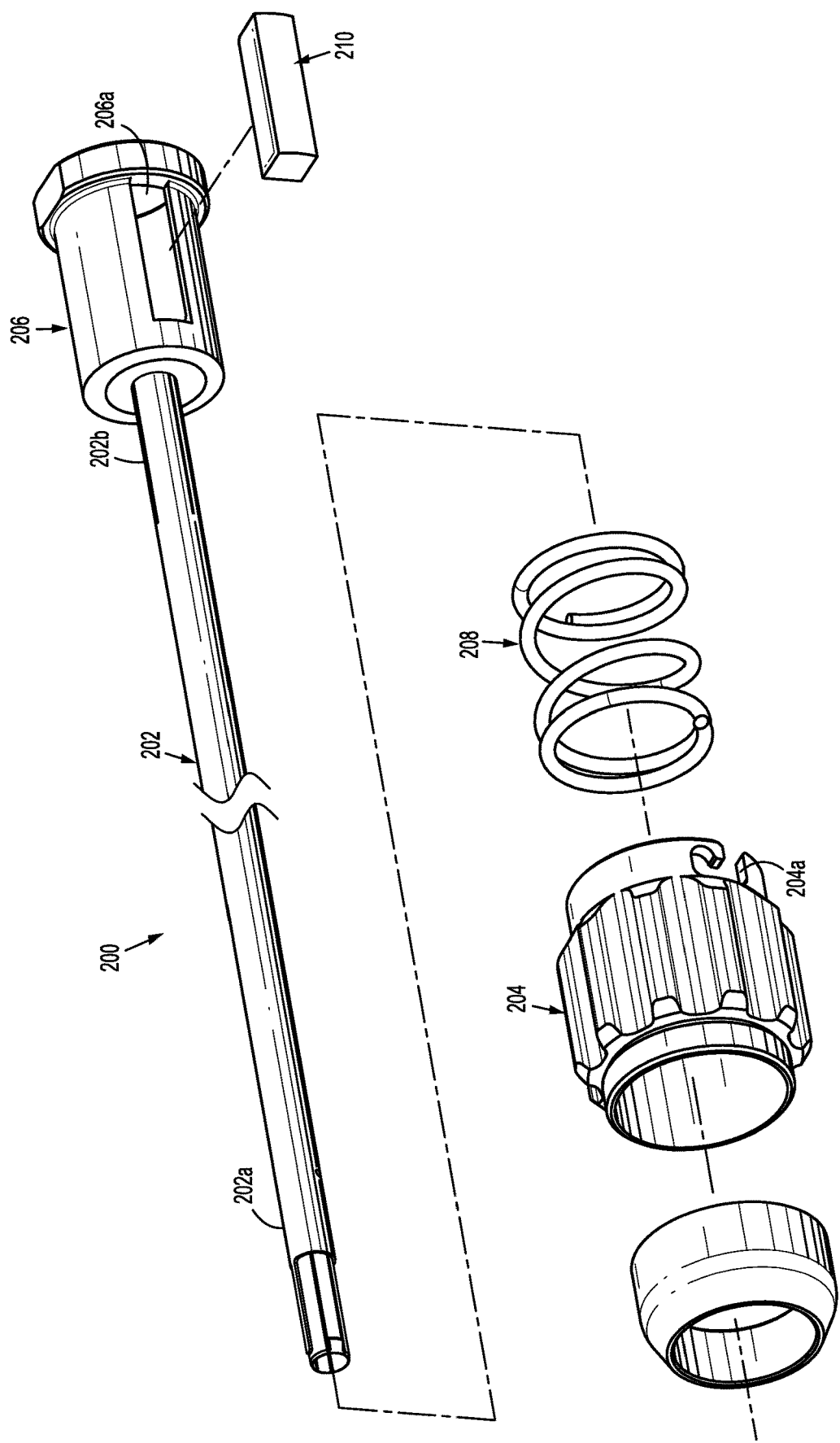
FIG. 4 is a perspective view, with parts separated, of an outer tube assembly of the reposable endoscopic surgical clip applier of FIGS. 1 and 2.

Referring initially to FIGS. 1-3, a surgical clip applier in accordance with an embodiment of the present disclosure is generally designated as 100. Surgical clip applier 100 includes a handle assembly 110, an elongated outer tube assembly 200 projecting from or extending from handle assembly 110, and a clip cartridge assembly 300 that can be removably and selectively mounted on a distal end of outer tube assembly 200. As will be described in greater detail below, a plurality of surgical clips "C" (FIG. 8) is loaded into clip cartridge assembly 300. Also, as will be described in greater detail below, in operation, as handle assembly 110 is actuated, a single surgical clip "C" is fired and formed around a vessel to be ligated.

Handle assembly 110, as shown in FIGS. 1-3, includes a fixed handle 112 and a squeezable trigger 114 pivotally attached to fixed handle 112 at pivot shaft 116. Squeezable trigger 114 includes a proximal actuating end 114a, which extends proximally beyond pivot shaft 116, and which extends into a bore 118a of a barrel 118 supported on fixed handle 112.

A barrel 118 is supported on fixed handle 112 and is configured to receive a proximal end of outer tube assembly 200. Barrel 118 defines a lumen or bore 118a therethrough. A threaded end cap 119 closes a proximal end of barrel 118. A nose 118b of barrel 118 includes a pair of diametrically opposed nubs 118c projecting radially therefrom, and which are configured and dimensioned to slidably engage a respective pair of oppositely disposed J-shaped notches 204a of an outer collar or knob 204 of outer tube assembly 200, in the manner of a bayonet-like connection, to secure outer tube assembly 200 to handle assembly 110.

Figure 18:
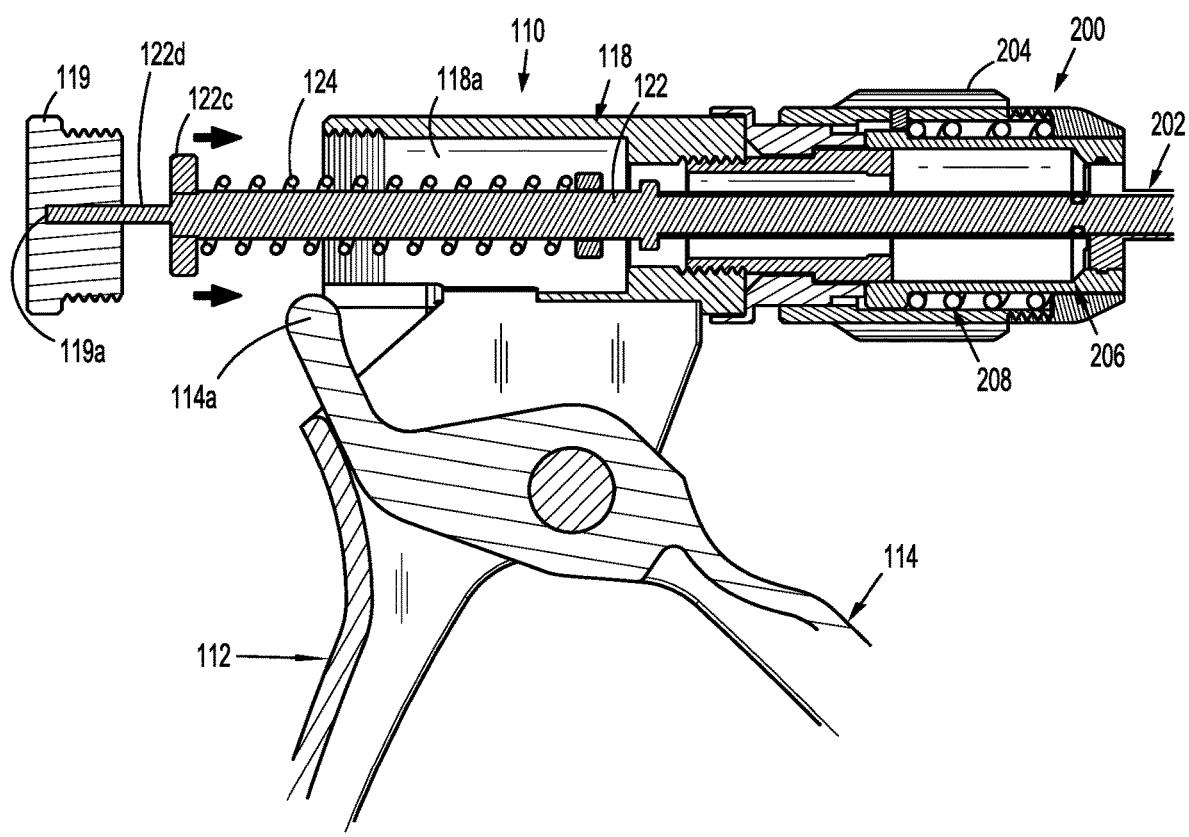
FIG. 18 is a cross-sectional view of the handle assembly illustrating an insertion of a main shaft assembly into the handle assembly.
Figure 19:
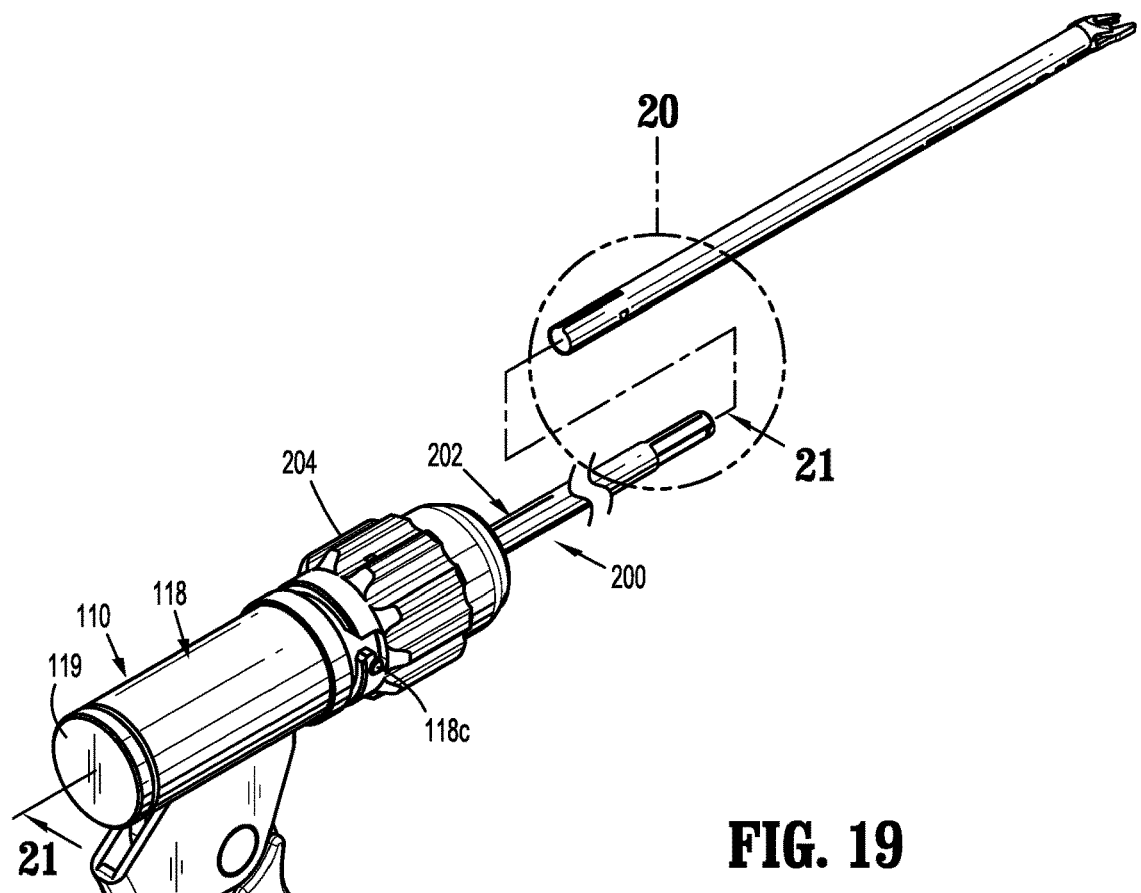
FIG. 19 is a perspective view of the reposable endoscopic surgical clip applier illustrating a connection of the disposable clip cartridge assembly of FIGS. 7-16 to the main shaft assembly of the handle assembly.
Figure 20:
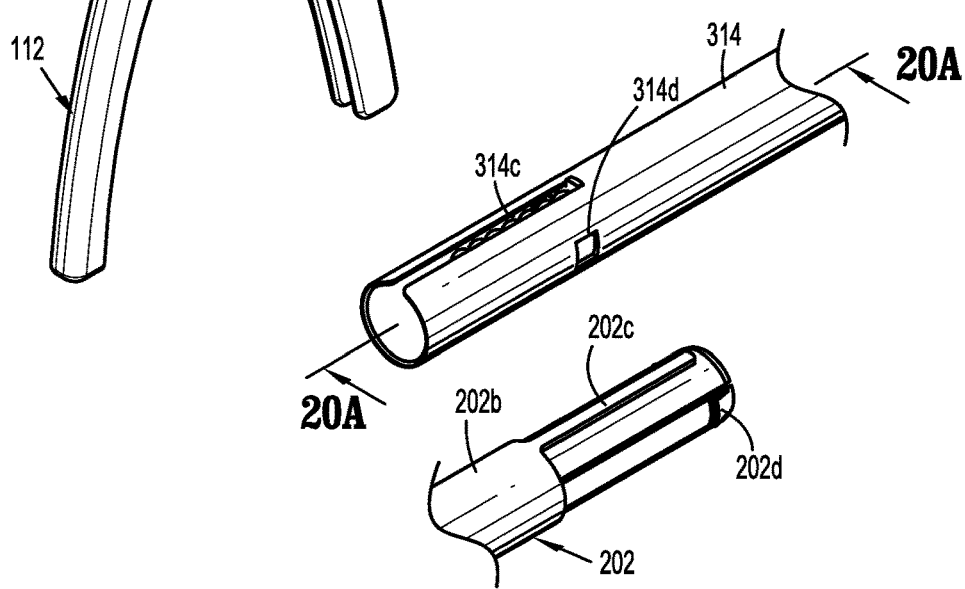
FIG. 20 is an enlarged view of the indicated area of detail of FIG. 19.
Figure 20A:
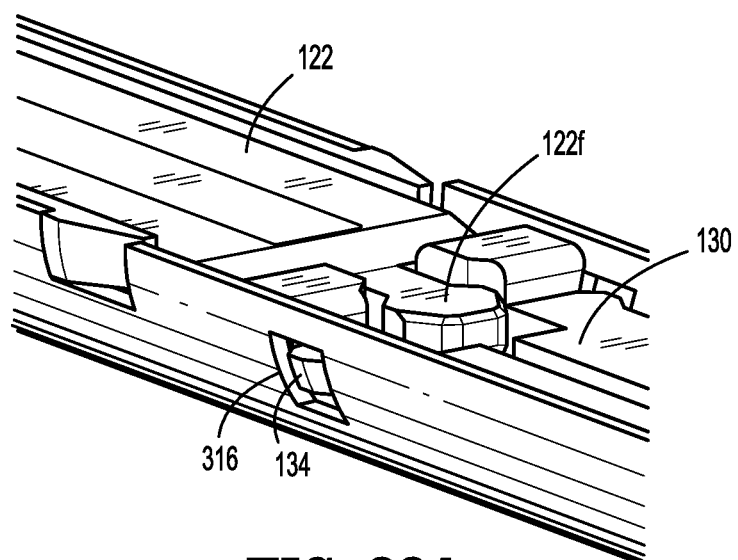
FIG. 20A is a cross-sectional view of the disposable clip cartridge assembly of FIG. 20, as taken along section line 20A-20A of FIG. 20.
Figure 20B:
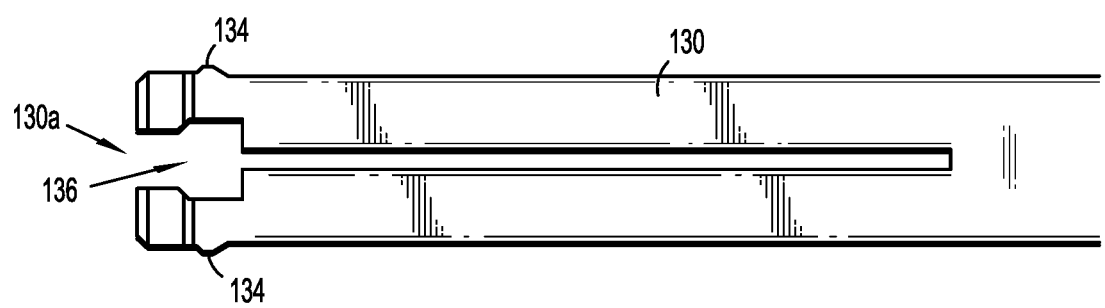
FIG. 20B is a top view of a pusher bar of the disposable clip cartridge assembly of FIG. 20.
Figures 21, 22:
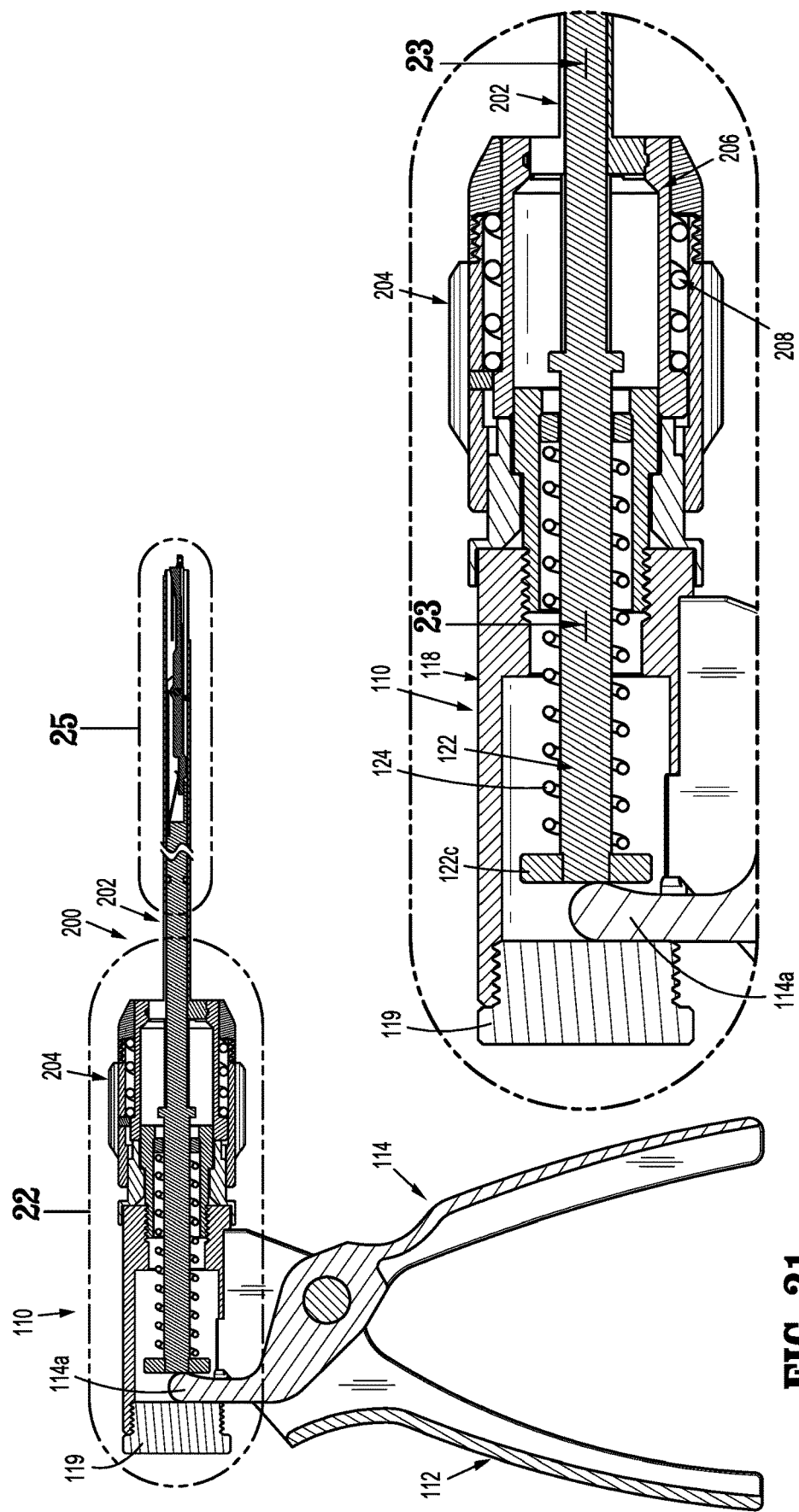
FIG. 21 is a longitudinal cross-sectional view of the reposable endoscopic surgical clip applier of FIG. 1, shown in an unactuated condition, and with the disposable clip cartridge assembly removed therefrom.
FIG. 22 is an enlarged view of the indicated area of detail of FIG. 21.

With reference to FIGS. 2, 5, and 6, handle assembly 110 supports and/or includes a main drive assembly or advancing mechanism 120 removably supported within bore 118b of barrel 118 or removably connected to barrel 118. Main drive assembly 120 includes a main drive rod 122 having a proximal end 122a and a distal end 122b. Proximal end 122a of main drive rod 122 supports a flange 122c thereon, and a biasing member 124 (e.g., a return compression spring) is disposed on main drive rod 122 and distal of flange 122c, to urge main drive rod 122 to a proximal-most position. An elongate extension 122d extends from flange 122c in a proximal direction and is configured to be received within a bore 119a defined within threaded end cap 119 (FIG. 18). Distal end 122b of main drive rod 122 includes a ball shaped tab 122f disposed thereon and extending distally therefrom.

Figure 26:
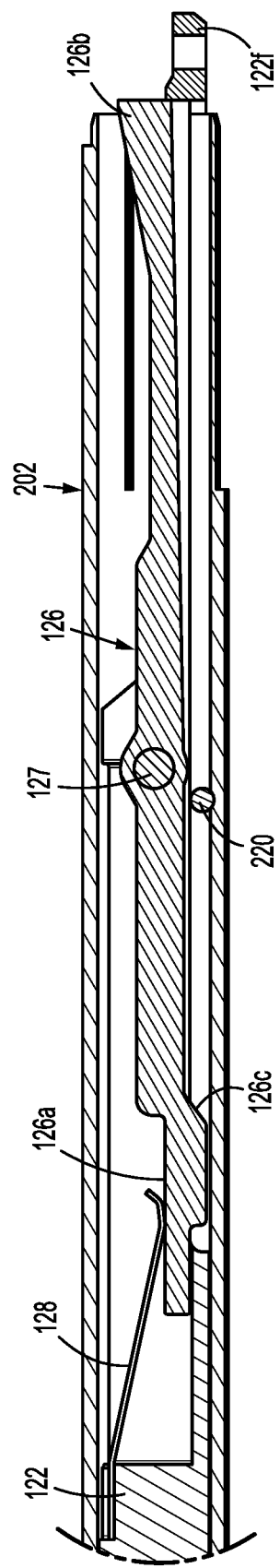
FIG. 26 is an enlarged view of the indicated area of detail of FIG. 25.

Main drive rod 122 pivotally supports a rocker 126 thereon via a pivot pin 127. Rocker 126 includes a proximal end 126a, and a distal end 126b. Distal end 126b has an enlarged head or piston configuration. A biasing member 128 (e.g., leaf spring) is supported on drive rod 122 and is configured to act on proximal end 126a of rocker 126. A cam ramp 126c (FIG. 26) is provided on or in a surface of rocker 126, and which is adjacent an outer tube 202 of outer tube assembly 200.

With reference to FIGS. 1, 2, 4, and 19, outer tube assembly 200 includes a hollow outer tube 202 having a proximal end 202a and a distal end 202b, and an outer collar or knob 204.

A proximal end of outer collar or knob 204 includes two oppositely disposed J-shaped notches 204a formed therein and being configured and dimensioned to selectively receive respective nubs 118c of barrel 118 of handle assembly 110, for selectively securing outer tube assembly 200 to handle assembly 110.

Outer tube assembly 200 further includes an inner collar 206 that is configured and dimensioned for disposition within outer collar 204. Inner collar 206 is mechanically secured to proximal end 202a of outer tube 202 using any suitable means, such as welding, adhesives, friction fit, or the like.

Outer tube assembly 200 also includes a biasing member 208 interposed between outer collar 204 and inner collar 206.

Figure 23:
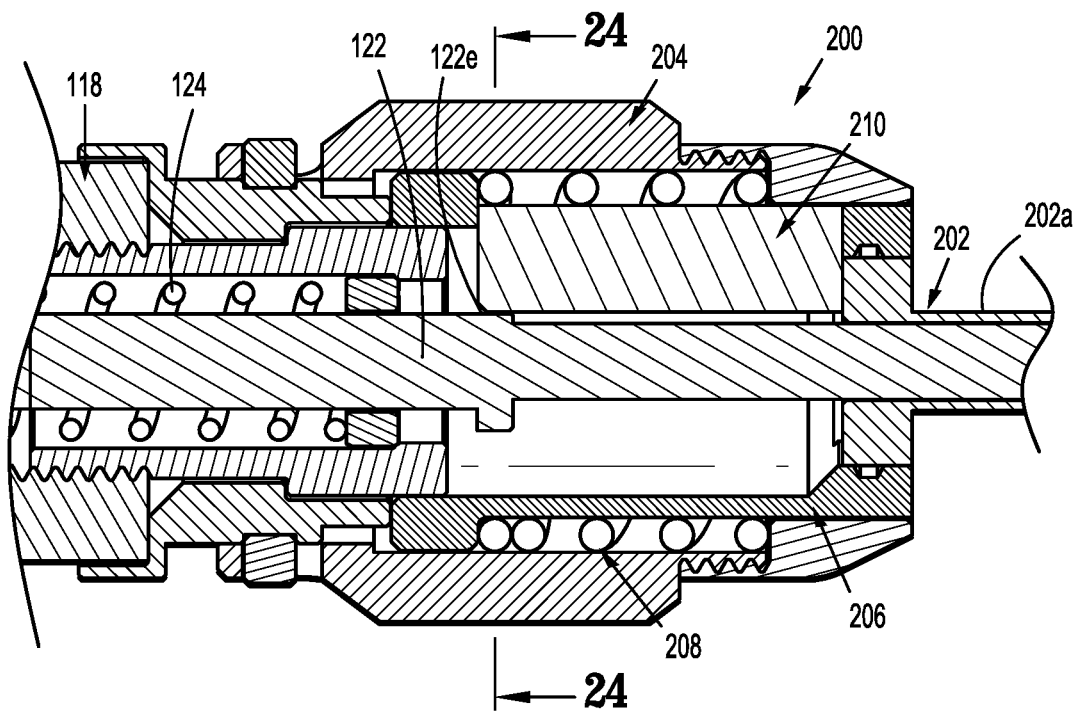
FIG. 23 is a cross-sectional view as taken along section line 23-23 of FIG. 22.
Figure 24:
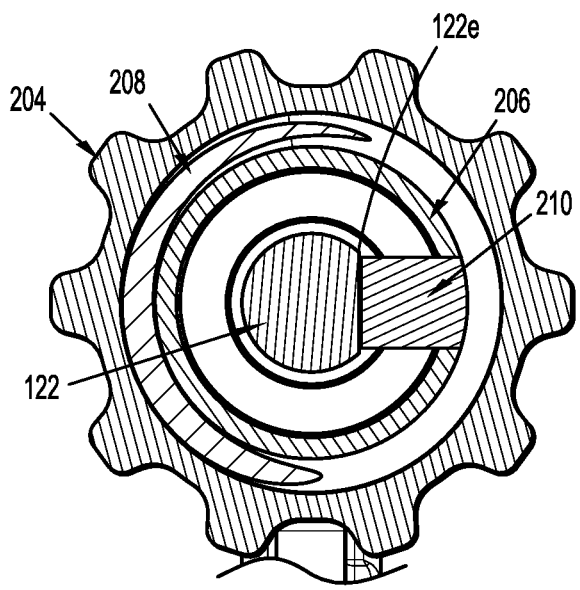
FIG. 24 is a cross-sectional view as taken along section line 24-24 of FIG. 23.
Figure 25:
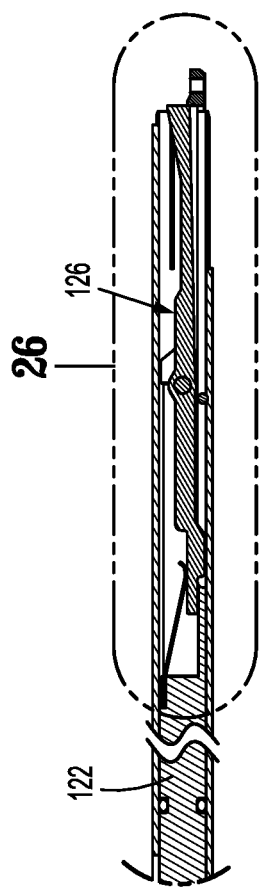
FIG. 25 is an enlarged view of the indicated area of detail of FIG. 21.

Inner collar 206 further includes a longitudinally extending slot or window 206a formed in a side thereof. A lock block 210 is provided for selective insertion into longitudinal slot or window 206a of inner collar 206. In use, when lock block 210 is inserted in slot or window 206a of inner collar 206, lock block 210 seats against or contacts a flat surface 122e of main drive rod 122 (see FIGS. 6, 23, and 24), thereby enabling rotation in a first direction and inhibiting or preventing main drive rod 122 from rotating in a second, opposite direction, when disposed within outer tube 202 of outer tube assembly 200.

Handle assembly 110, as well as outer tube assembly 200, may be made from a biocompatible material, such as, for example, a high grade surgical stainless steel, from titanium, or from a high strength autoclavable polymer, thermoplastic or the like.

With reference to FIG. 18, assembly of handle assembly 110, main drive assembly 120, and outer tube assembly 200 is described. Outer collar or knob 204 of outer tube assembly 200 is connected to nose 118b of barrel 118 of handle assembly 110 by aligning an open end of the J-shaped notches 204a of outer collar or knob 204 with nubs 118c of barrel 118 of handle assembly 110, approximating outer tube assembly 200 and handle assembly 110 until nubs 118c are fully received in the J-shaped notches 204a, and then rotating outer tube assembly 200 relative to handle assembly 110 to advance nubs 118c radially around the J-shaped notches 204a, e.g., in the manner of a bayonet-type connection.

With outer tube assembly 200 connected to handle assembly 110, and with end cap 119 removed from barrel 118, trigger 114 is moved or pivoted about pivot shaft 116 until actuating end 114a of trigger 114 does not obstruct bore 118a of barrel 118. With trigger 114 so positioned, distal end 122b (FIG. 2) of main drive rod 122 is inserted into bore 118a of barrel 118 via an open proximal end of barrel 118. Main drive assembly 120 is advanced through bore 118a of barrel 118 and through outer tube assembly 200 until flange 122c of main drive assembly 120 is positioned within bore 118a of barrel 118. With flange 122c of main drive assembly 120 positioned within bore 118a of barrel 118, trigger 114 is moved or pivoted about pivot shaft 116 until actuating end 114a of trigger 114 is once again disposed with in bore 118a of barrel 118 and disposed adjacent to and in contact with flange 122c of main drive assembly 120. The end cap 119 may then be advanced over elongate extension 122d such that elongate extension 122d nests within bore 119a. With elongate extension 122d nested within bore 119a, end cap 119 is further advanced thereover and re-connected to barrel 118 to secure main drive assembly 120 and actuating end 114a of trigger 114 to barrel 118 of handle assembly 110. As will be discussed in further detail hereinbelow, end cap 119 may be advanced into and out of bore 118a of barrel 118 to facilitate attachment and removal of clip cartridge assembly 300. In this manner, elongate extension 122d remains in slidable engagement with bore 119a and maintains main drive assembly 120 in alignment with outer tube assembly 200 as end cap 119 is advanced or withdrawn within bore 118a or barrel 118.

Turning now to FIGS. 1, 2, and 7-17, clip cartridge assembly 300 of surgical clip applier 100 is shown. Clip cartridge assembly 300 is configured to be selectively loadable or connectable to distal end of outer tube assembly 200, and to be actuated upon an actuation of trigger 114 of handle assembly 110 to fire and form surgical clips "C" loaded therein onto underlying tissue and/or vessels. Each clip cartridge assembly 300 may be loaded with a particularly sized set of surgical clips (e.g., relatively small surgical clips, relatively medium surgical clips, or relatively large surgical clips).

Clip cartridge assembly 300 includes a clip tray 302 including base wall 302a and a pair of spaced apart lower side walls or rails $302b_1$ supported on base wall 302a. Base wall 302a and lower rails $302b_1$ define a clip channel $302c_1$ (FIG. 11). Clip channel $302c_1$ is configured and dimensioned to slidably support a plurality of surgical clip "C" therein. Clip tray 302 further includes at least a pair of spaced apart upper side walls or rails $302b_2$ supported on lower side walls $302b_1$. Lower rails $302b_1$ and upper rails $302b_2$ define a pusher bar channel $302c_2$ (FIG. 11). Pusher bar channel $302c_2$ is configured and dimensioned to slidably support a cartridge clip pusher bar 304 therein.

Clip tray 302 includes a linear array of distally extending resilient, deflectable fingers 302d (FIGS. 13, 15, and 17) projecting up from base wall 302a and into lower clip channel $302c_1$ at a location between side rails 302b. A distal-most deflectable finger $302d_1$ forms a single, rectangular finger configured to engage a backspan or crown of the distal-most clip "C1" and nest between the spaced apart prongs $304d_1$, $304d_2$ (FIG. 13) of cartridge clip pusher bar 304, as discussed below. A pair of channels 302f (FIG. 17) are disposed or formed on either side of the distal-most finger $302d_1$ and are configured to selectively receive engage each of the spaced apart prongs $304d_1$, $304d_2$ of clip pusher bar 304 when all of the surgical clips "C" have been formed, as will be discussed in further detail below. Each of the remaining proximal deflectable fingers 302d define a V-shaped configuration adapted to engage opposing proximal sides of a backspan of each remaining clip of the stack of surgical clips "C", as illustrated in FIGS. 12, 13, 16 and 17.

As shown in FIGS. 11 and 17, clip tray 302 further includes a pair of spaced apart, distally extending resilient deflectable prongs 302e projecting up from the proximal end of base wall 302a and into lower clip channel $302c_1$ at a location between side rails $302_1$. Each of the prongs 302e is spaced apart such that they are in slidable engagement with a surface of a respective leg of the distal-most clip "C1". Prongs 302e are dimensioned to engage the legs of the distal-most clip "C1" and frictionally press the distal-most clip "C1" against each side rail $302b_1$, such that prongs 302e help to prevent the distal-most clip "C1", proximal to the distal-most clip "C1", from advancing distally past prongs 302e when the distal-most clip "C1" is being loaded into a pair of jaws 320. The biasing force provided by the prongs 302e is overcome when the distal-most clip "C1" is urged distally by the cartridge clip pusher bar 304, and once the distal-most clip "C1" has been loaded into the pair of jaws 320, each of the prongs 302e returns to their initial position to prevent the next clip "C" from advancing any further.

Figure 14:
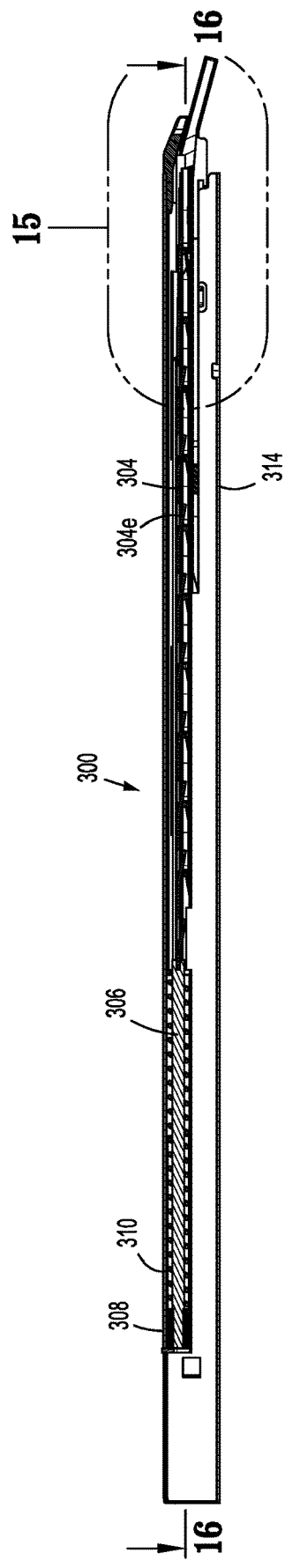
FIG. 14 is a cross-sectional view of the disposable clip cartridge assembly of FIGS. 7-13, as taken along section line 14-14 of FIG. 7.
Figure 15:
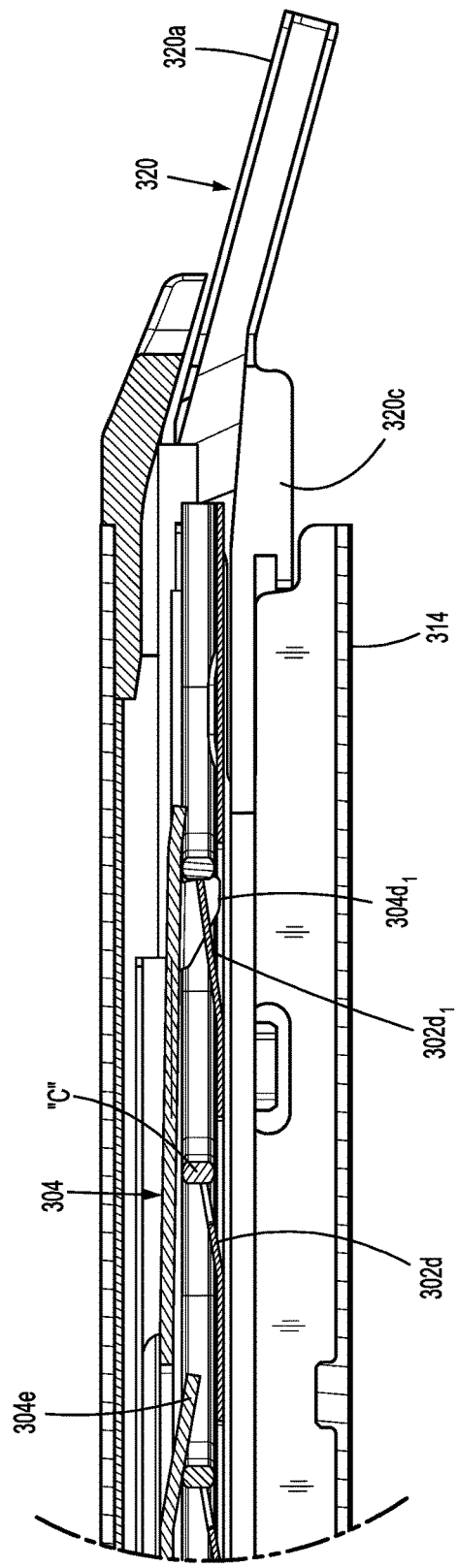
FIG. 15 is an enlarged view of the indicated area of detail of FIG. 14.

Clip cartridge assembly 300 includes, as shown in FIGS. 8-15, a cartridge clip pusher bar 304 slidably disposed between and within the pair of spaced apart upper side walls or rails $302b_2$ (FIG. 11) of clip tray 302. Cartridge clip pusher bar 304 includes a proximal end 304a engagable with or by a distal end of a cartridge pusher rod or shaft 306, as will be described in greater detail below. Cartridge clip pusher bar 304 further includes a distal end portion 304b defining a pusher 304d configured to engage a distal-most clip "C1" of a stack of surgical clips "C" for loading the distal-most clip "C1" into the pair of jaws 320 of clip cartridge assembly 300. Pusher 304d includes, as described above, a pair of spaced apart prongs $304d_1$, $304d_2$ configured to engage a backspan of the distal-most clip "C1", as illustrated in FIGS. 11 and 15.

As illustrated in FIGS. 8, 14, and 15, cartridge clip pusher bar 304 further includes a linear array of distally extending resilient, deflectable fingers 304e, with each finger 304e defining a rectangular profile including a distal shoulder formed at a distal end thereof. In use, when cartridge clip pusher bar 304 overlays or is disposed between the pair of spaced apart upper rails $302b_2$ of clip tray 302, each of the deflectable fingers 302d of clip tray 302 is disposed axially between each deflectable finger 304e of cartridge clip pusher bar 304, such that each of deflectable fingers 302d, 304e are arranged in a tandem configuration when the clip pusher bar 304 is in a proximal position relative to clip tray 302. Additionally, when cartridge clip pusher bar 304 overlays or is disposed between the pair of spaced apart upper rails $302b_2$ of clip tray 302, each deflectable finger 304e of cartridge clip pusher bar 304 extends across clip channel $302c_1$ of clip tray 302 such that the distal shoulders of deflectable fingers 304e are in registration with the stack of surgical clips "C".

In use, the V-shaped configuration of the proximal deflectable fingers 302d of clip tray 302 permits each proximal deflectable finger 304e of the cartridge clip pusher bar 304 to nest within the V-shape of the proximal deflectable fingers 302d such that the distal shoulders of deflectable fingers 304e engage a backspan of each of the remaining surgical clips of the stack of surgical clips "C" as the cartridge clip pusher bar 304 is driven distally.

As shown in FIG. 8, and 12-17, clip cartridge assembly 300 further includes a stack of surgical clips "C" interposed between clip tray 302 and cartridge clip pusher bar 304. The stack of surgical clips "C" is supported on or loaded in clip tray 302 such that a crown or backspan of each surgical clip "C" is disposed distal of a respective deflectable finger 302d of clip tray 302. Further, when cartridge clip pusher bar 304 is in a proximal position relative to clip tray 302, each deflectable finger 304e of cartridge clip pusher bar 304 is also disposed proximal of the crown or backspan of a respective clip of the stack of surgical clips "C" as discussed above.

Clip cartridge assembly 300 may be loaded with 10 surgical clips "C", or, in embodiments, clip cartridge assembly 300 may be loaded with any number of surgical clips C". Surgical clips "C" may be fabricated from materials know by those skilled in the art, including and not limited to stainless steel, titanium, or other metal alloys. In an embodiment it is contemplated that at least a final surgical clip of the stack of surgical clips "C" may be dyed a particular color to indicate to the user when a final surgical clip of clip cartridge assembly 300 is loaded into the pair of jaws 320.

Once all of the surgical clips "C" are loaded into the clip tray 302 and cartridge clip pusher bar 304 is placed adjacent thereto, a channel cover 307 (FIG. 8), configured and adapted for connection and support on clip tray 302, may be snapped into engagement with lower rails $302b_1$ of clip tray 302.

With reference to FIGS. 8-10, 14, and 16, clip cartridge assembly 300 includes a cartridge pusher rod or shaft 306 slidably supported within clip tray 302. Cartridge pusher rod 306 includes a distal end connected to proximal end 304a of cartridge clip pusher bar 304, and a proximal end fixedly connected to a drive sled 308 with drive sled 308 being slidably supported within clip tray 302.

Clip cartridge assembly 300 includes a biasing member 310 disposed about cartridge pusher rod 306 and interposed between a distal stop block 312a and drive sled 308. A proximal stop block 312b is provided near proximal end of clip tray 302 to limit movement of drive sled 308. The distal end of cartridge pusher rod 306 extends distally past distal stop block 312a for engagement with the proximal end of cartridge clip pusher bar 304.

In operation, as will be described in greater detail below, as trigger 114 of handle assembly 110 is actuated, trigger 114 effects actuation of main drive rod 122 and rocker 126 of main drive assembly 120 to move rocker 126 in an axially distal direction. As main drive assembly 120 is moved in a distal direction distal end 126b of rocker 126 engages, abuts or acts on drive sled 308 to move drive sled 308 in a distal direction. As drive sled 308 is moved in a distal direction, drive sled 308 acts on cartridge clip pusher bar 304 to distally advance cartridge clip pusher bar 304, and effectuates compression of biasing member 310 to a biased condition.

Continuing with FIGS. 8-10, 14, and 16, clip cartridge assembly 300 includes a jaw blade 320 fixedly supported adjacent clip tray 302, within a lumen 314a of an outer tube 314 of clip cartridge assembly 300. Jaw blade 320 includes a pair of jaws 320a projecting from or extending distally from within outer tube 314, and a proximal stem 320b extending proximally into lumen 314a of outer tube 314. Jaw blade 320 is fabricated from a resilient material, such as, for example, stainless steel, and is formed such that the pair of jaws 320a thereof is spaced apart from one another or is biased apart from one another.

Each jaw 320a includes a cam tooth or wedge 320c projecting therefrom and configured to be engaged by V-shaped cam groove 132e provided at distal end 132b of second jaw pusher 132 (FIGS. 28A and 34) when main drive rod 122 of main drive assembly 120 is advanced distally. In operation, as main drive rod 122 is advanced distally, main drive rod 122 urges a first jaw pusher 130 distally until a distal end 130b of first jaw pusher 130 contacts a proximal surface 132d of a second jaw pusher 132. In this manner, first jaw pusher 130 and second jaw pusher 132 are initially disposed apart from one another such that a gap exists therebetweeen. Thereafter, both first and second jaw pushers 130, 132 are advanced distally such that the V-shaped cam groove 132e of second jaw pusher 132 engages cam teeth 320c of the pair of jaws 320a thereby resulting in a closure or approximation of the pair of jaws 320a. In this manner, first jaw pusher 130 may be advanced distally without causing the pair of jaws 320a to approximate.

Jaw blade 320 defines a channel between the pair of jaws 320a for receipt of a surgical clip "C" therein, when jaw blade 320 is an in un-approximated condition.

As briefly mentioned above, and as shown in FIGS. 7 and 8, clip cartridge assembly 300 includes an outer tube 314 defining a lumen 314a therethrough. Outer tube 314 is configured and dimensioned to operatively house clip tray 302, clip cartridge pusher 304, cover 307, clip pusher rod 306, drive sled 308, biasing member 310, jaw blade 320, and the stack of surgical clips "C" therewithin. A proximal end 314b of outer tube 314 defines a distally extending groove or channel 314c formed therein.

Generally, in operation, as main drive rod 122 of handle assembly 110 is distally advanced, due to an actuation of trigger 114, main drive rod 122 advances rocker 126 to act on drive sled 308 of cartridge assembly 300 to move drive sled 308 in a distal direction. As drive sled 308 is moved in a distal direction, drive sled 308 acts on cartridge pusher rod 306, and in turn, cartridge clip pusher bar 304 to distally advance cartridge clip pusher bar 304 by an amount or distance "X" (e.g., about 12 mm), and effectuates compression of biasing member 310 to a biased condition.

As cartridge clip pusher bar 304 of clip cartridge assembly 300 is moved in a distal direction, the spaced apart prongs 304$d_1$, 304$d_2$ of pusher 304$d$ of cartridge clip pusher bar 304 engages the backspan of distal-most clip "C1" and pushes distal-most clip "C1" distally, by the amount or distance "X", out of clip cartridge assembly 300 and into the pair of jaws 320$a$.

As mentioned above, the distal movement of the distal-most clip "C1" compresses each of the spaced apart prongs 302$e$ of the clip tray 302, thereby permitting the distal-most clip "C1" to be loaded within the pair of jaws 320$a$, as described above. Once the distal-most clip "C1" is loaded into the pair of jaws 320$a$, the prongs 302$e$ return to their initial position and prevent the clips "C", proximal to the distal-most clip "C1", from advancing further distally.

Additionally, and simultaneously with a distal movement of the distal-most clip "C1", as cartridge clip pusher bar 304 of clip cartridge assembly 300 moves in a distal direction, the distal shoulder of each finger 304$e$ of cartridge clip pusher bar 304 abuts against a respective backspan of a respective surgical clip of the remaining surgical clips "C" to also urge the remaining surgical clips "C" in a distal direction, by the amount or distance "X". In so doing, fingers 302$d$ of the clip tray 302 are deflected, permitting each of the remaining surgical clips "C" to advance distally to replace each respective surgical clip of the stack of surgical clips "C". Once distal advancement of cartridge clip pusher bar 304 is completed, distal advancement of the stack of surgical clips "C" is also completed. Once the clips of the remaining stack of surgical clips "C" has distally advanced beyond respective fingers 302$d$ of clip tray 302, fingers 302$d$ of clip tray 302 spring back or return to their original position, thereby preventing each surgical clip "C" from any movement thereafter in a proximal direction.

Cartridge clip pusher bar 304 distally advances the remaining surgical clips "C" until each remaining surgical clip "C" is advanced distally, by the amount or distance "X", past a next adjacent resilient, deflectable finger 302$d$ of clip tray 302.

Following movement of cartridge clip pusher bar 304, by the amount or distance "X", to load the distal-most clip "C1" into the pair of jaws 320$a$, a release or reversing feature 220, e.g., a nub or pin provided in outer tube 202 of outer tube assembly 200 is engaged or contacted by cam ramp 126$c$ (FIG. 26) of rocker 126, to thus disengage piston 126$b$ of rocker 126 from drive sled 308, to effectuate a reversal of the direction of travel of clip cartridge pusher bar 304, from the distal direction to a proximal direction. The actuation of rocker 126 by reversing feature 220 of outer tube 202 causes the distally directed forces acting on cartridge clip pusher bar 304 to be removed, and thus biasing member 310 is free to re-expand. As biasing member 310 is free to re-expand, biasing member 310 urges or moves drive sled 308 proximally to thereby withdraw cartridge clip pusher bar 304 proximally.

As cartridge clip pusher bar 304 is moved in a proximal direction, a proximal surface of fingers 304$e$ thereof abut against a distal surface of the backspans of the remaining surgical clips "C" to also urge the remaining surgical clips "C" in a proximal direction. Fingers 304$e$ of cartridge clip pusher bar 304 proximally retract the remaining surgical clips "C" until each remaining surgical clip "C" is retracted, by an amount or distance less than "X" (e.g., "X Y"), into contact with a respective distal tip of a respective resilient, deflectable finger 302$d$ of clip tray 302, which blocks or stops further proximal retraction of the remaining surgical clips "C", while cartridge clip pusher bar 304 continues to move proximally to the proximal-most position thereof, e.g., an amount or distal "X".

As cartridge clip pusher bar 304 continues to be drawn proximally, concurrently, the spaced apart prongs 304$d_1$, 304$d_2$ of pusher 304$d$ and fingers 304$e$ of cartridge clip pusher bar 304 are deflected up and over each of the remaining surgical clips "C" until cartridge clip pusher bar 304 returns to a proximal-most position.

When clip cartridge assembly 300 is loaded with at least one clip "C", and when cartridge clip pusher bar 304 is in a proximal-most position, a nose 304$g$ (FIG. 28) disposed on a distal-most end of cartridge clip pusher bar 304 is biased towards, and is supported by, an upper surface of a backspan of the distal-most surgical clip "C1", preventing each of the spaced apart prongs 304$d_1$, 304$d_2$ of pusher 304$d$ from engaging or entering the pair of channels 302$f$ of clip tray 302.

Turning now to FIGS. 19, 20, and 37-39, with outer tube assembly 200 connected to handle assembly 110, and with main drive assembly 120 loaded into handle assembly and outer tube assembly 200, as described above, clip cartridge assembly 300 may be selectively connected to a distal end of main drive assembly 120 and to a distal end of outer tube assembly 200.

Figure 37:
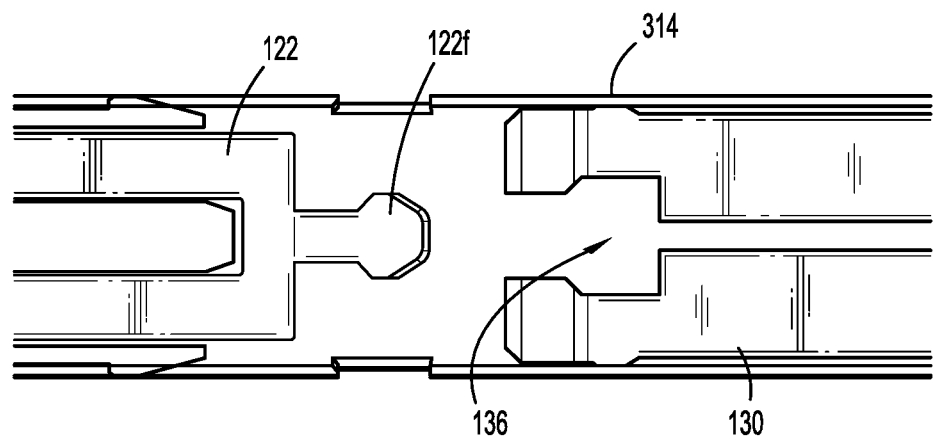
FIGS. 37-39 are top, cross-sectional, views of the disposable clip cartridge assembly and the outer tube assembly of the reposable endoscopic surgical clip applier, illustrating selective attachment of the main drive rod and the pusher bar.
Figure 38:
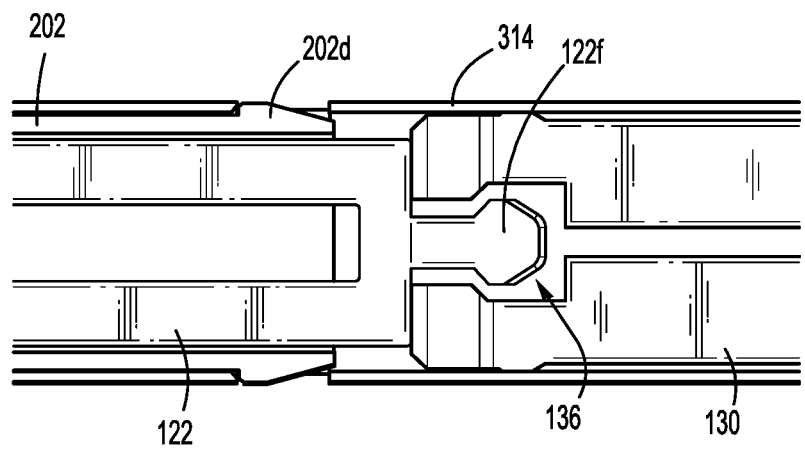
Figure 39:
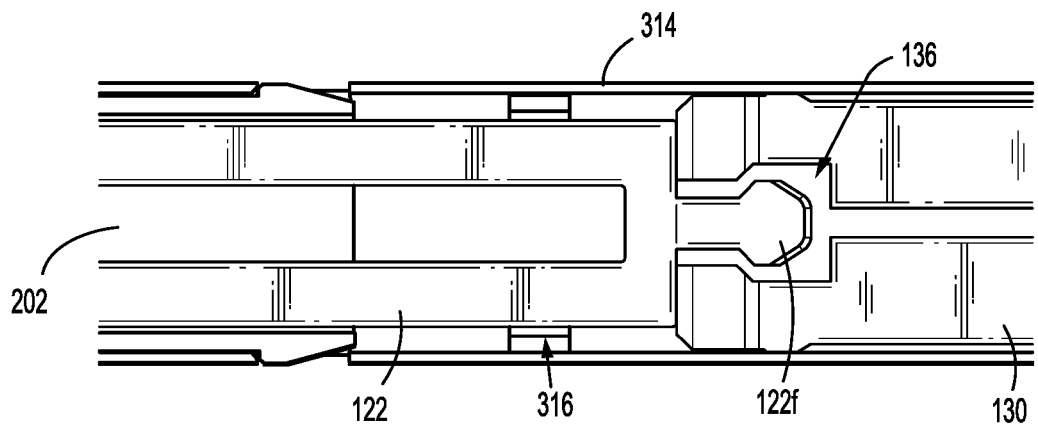

Generally, with reference to FIGS. 37-39, with clip cartridge assembly 300 fully assembled, the distal end of main drive assembly 120 is inserted into proximal end 314$b$ of outer tube 314 of clip cartridge assembly 300, and clip cartridge assembly 300 is approximated toward handle assembly 110 until an alignment rib 202$c$ provided on proximal end 202$a$ of outer tube 202 of outer tube assembly 200 aligns with and enters channel 314$c$ (See FIG. 29) of outer tube 314 of clip cartridge assembly 300. At this point, first jaw pusher 130 is in a proximal most position such that a pair of tabs 134 extending laterally from the outer sides of the proximal end 130$a$ of first jaw pusher 130 extend into respective windows 316 (See FIG. 39) defined within outer tube 314 of clip cartridge assembly 300. In this manner, the proximal end 130$a$ of first jaw pusher 130 may expand to a spaced apart condition capable of accepting ball shaped tab 122$f$ of main drive rod 122 within a pocket 136 defined within first jaw pusher 130. Thereafter, clip cartridge assembly 300 may be frictionally retained on or secured to outer tube assembly 200 by a snap-fit connection, or some other connecting arrangement known by one of skill in the art, for example, such as by detents, lips, or wings. In one exemplary embodiment, tabs 202$d$ project from outer sides of outer tube 202 of outer tube assembly 200 and extend into respective windows 314$d$ formed in outer tube 314 of clip cartridge assembly 300 such that clip cartridge assembly 300 is detachably secured to outer tube assembly 200 and to handle assembly 110.

At this point, threaded end cap 119 is advanced within bore 118$a$ of barrel 118 such that elongate extension 122$d$ of main drive rod 122 abuts an interior surface of bore 119$a$ such that main drive rod 122 is urged distally (FIG. 38). In this manner, as main drive rod 122 is urged distally, first jaw pusher 130 is likewise urged distally such that the pair of tabs 134 are dislodged from windows 316 of outer tube 314

Figure 40:
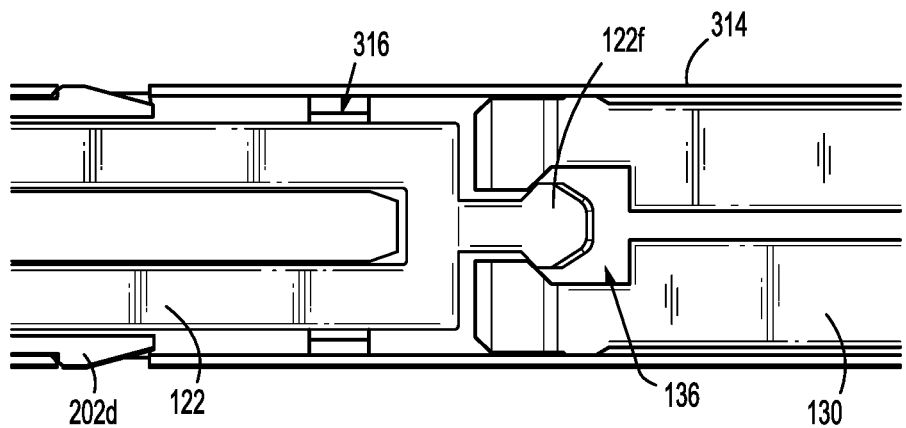
FIGS. 40-42 are top, cross-sectional, views of the disposable clip cartridge assembly and the outer tube assembly of the reposable endoscopic surgical clip applier, illustrating selective removal of the main drive rod and the pusher bar.
Figure 41:
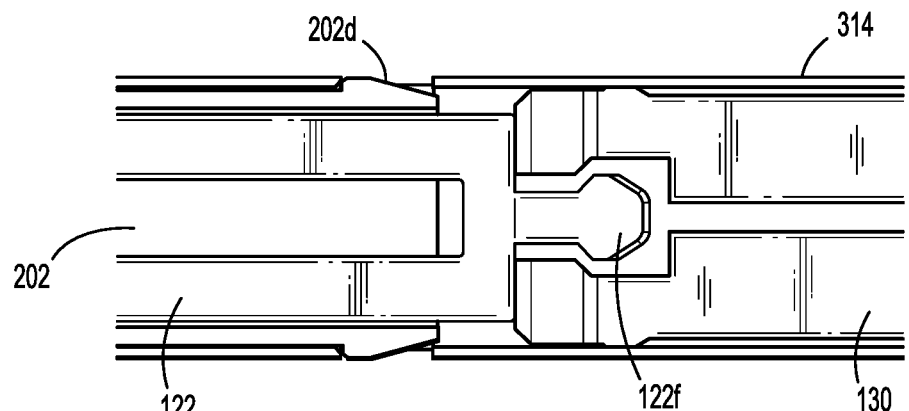
Figure 42:
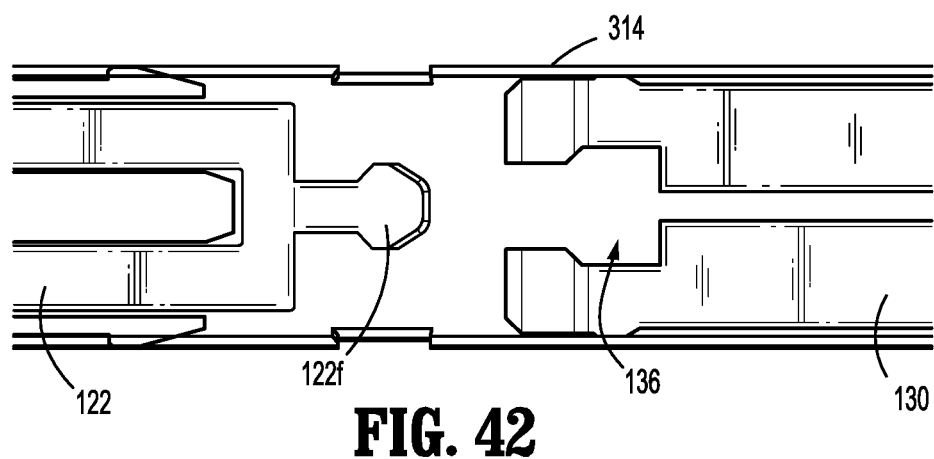

(FIG. 39). As the pair of tabs 134 are dislodged from windows 316, each of the respective pair of tabs contact in inner surface (not shown) of outer tube 314, thereby causing the proximal end 130a of first jaw pusher 130 to compress to an approximated position and capturing ball shaped tab 122f therein. In this manner, both the main drive rod 122 and first jaw pusher 130 act in unison, such that as main drive rod is advanced or retracted, first jaw pusher 130 is likewise advanced or retracted. In order to remove clip cartridge assembly 300 from outer tube assembly 200, the above noted procedure may be conducted in a reverse manner, as illustrated in FIGS. 40-42.

Figure 27:
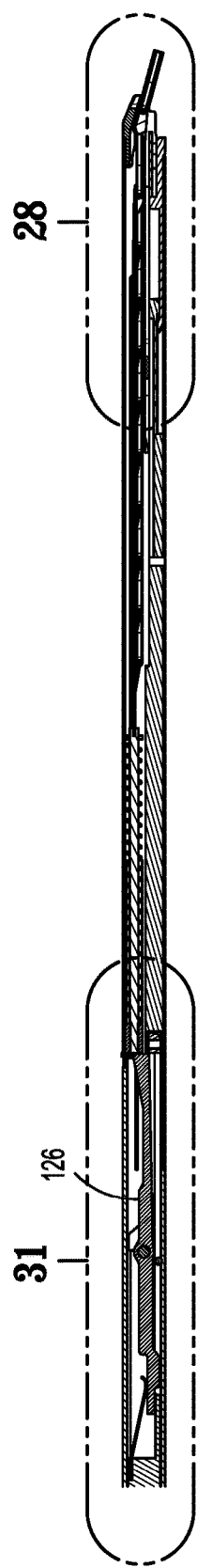
FIG. 27 is a longitudinal cross-sectional view of the disposable clip cartridge assembly, shown connected to the outer tube assembly of the reposable endoscopic surgical clip applier.
Figure 28:
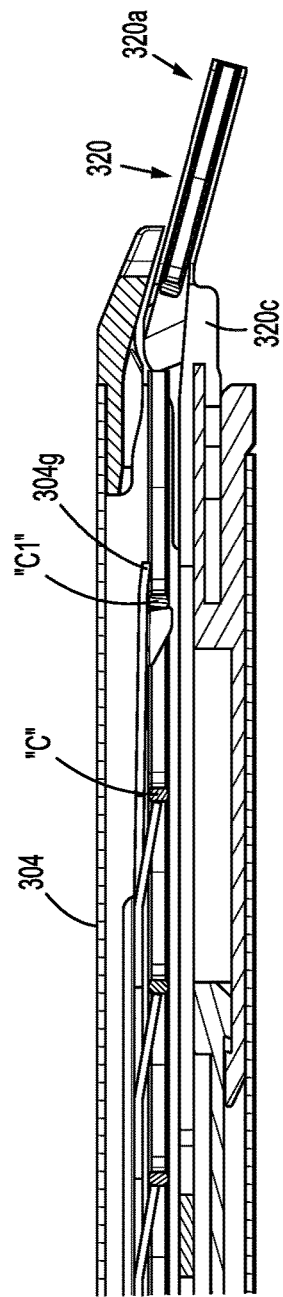
FIG. 28 is an enlarged view of the indicated area of detail of FIG. 27.
Figure 28A:
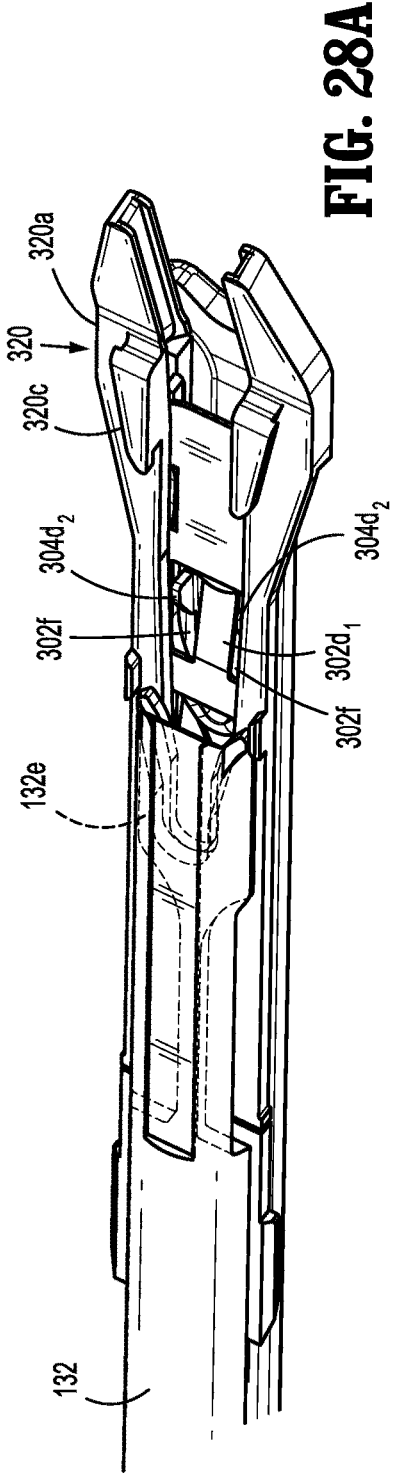
FIG. 28A is bottom, perspective view of the distal end of the disposable clip cartridge assembly.
Figure 29:
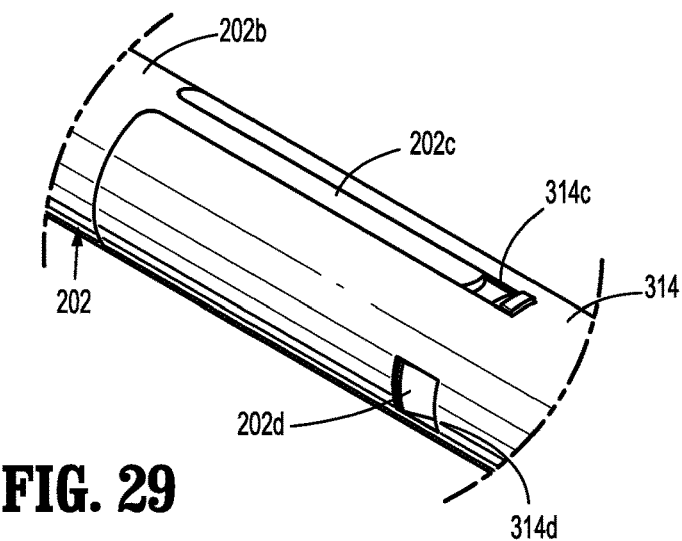
FIG. 29 is an enlarged, perspective view of the indicated area of detail of FIG. 1, illustrating a connection of the disposable clip cartridge assembly to the outer tube assembly of the reposable endoscopic surgical clip applier.

With continued reference to FIGS. 1-20B and 37-42, and with additional specific reference to FIGS. 21-36, an exemplary mode of operation of clip applier 100 is shown and described. As shown in FIGS. 27-29, clip applier 100 is illustrated with clip cartridge assembly 300 connected to distal end of outer tube assembly 200 and to distal end of main drive assembly 120 (as described above).

Figure 30:
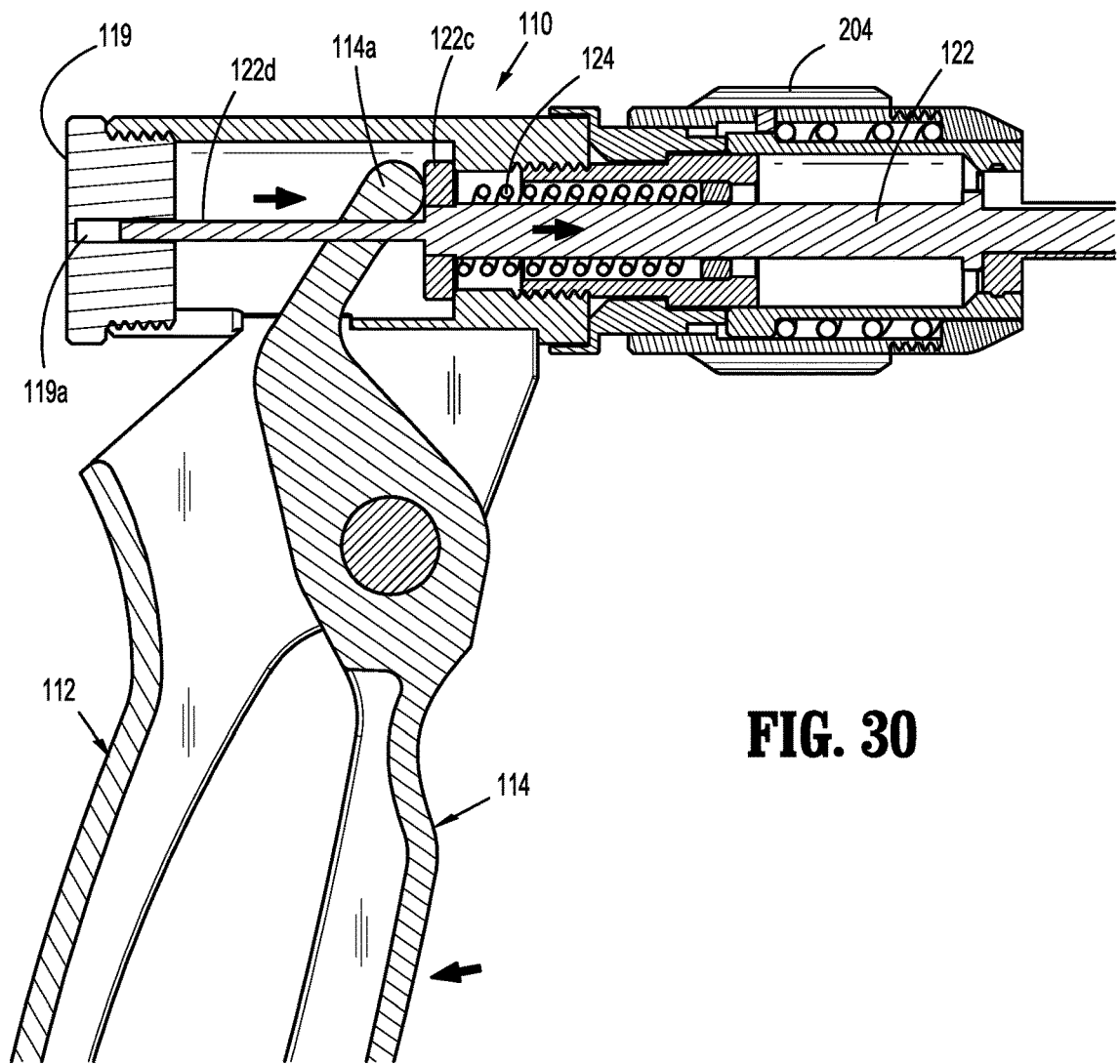
FIG. 30 is a longitudinal cross-sectional view of the handle assembly of the reposable endoscopic surgical clip applier of FIG. 1, illustrating an actuation or squeezing of a trigger thereof.
Figure 36:
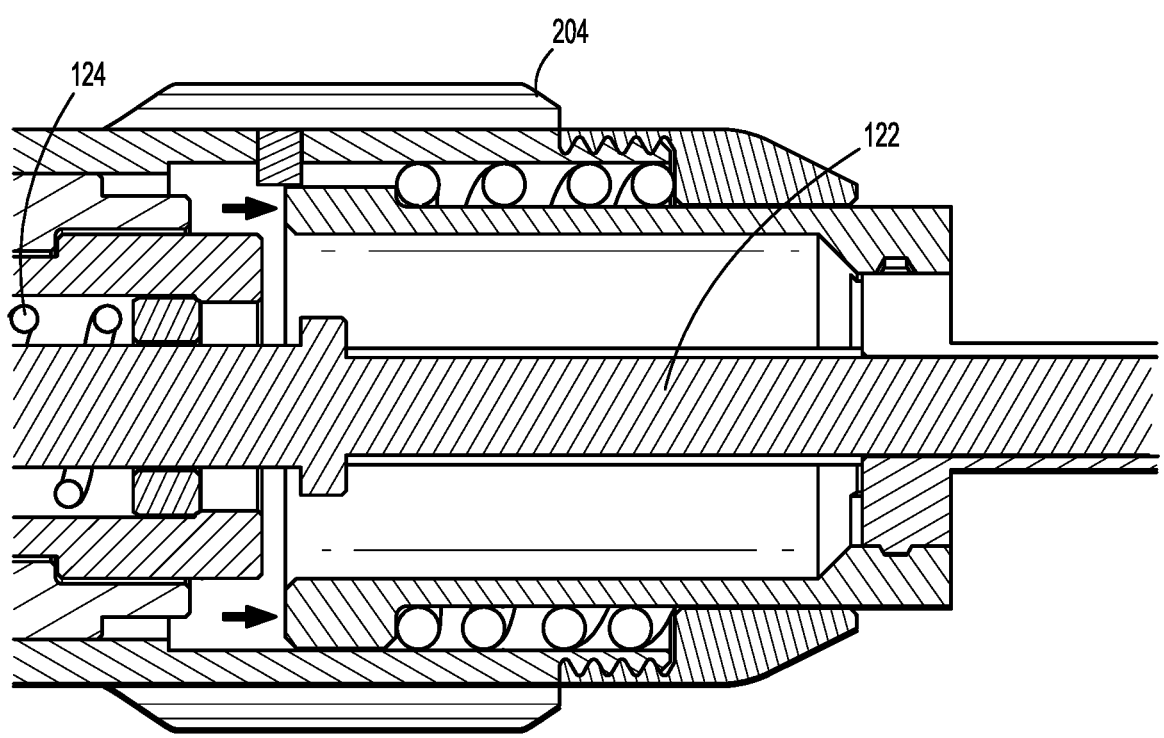
FIG. 36 is a cross-sectional, elevational view of an overload protection assembly of the reposable endoscopic surgical clip applier.

With reference to FIG. 30, when trigger 114 is squeezed or pivoted in the clockwise direction about pivot shaft 116, actuating end 114a of trigger 114 engages the proximal end of main drive rod 122 of handle assembly 110 thereby urging main drive rod 122 distally against the biasing force of return compression spring 124. As trigger 114 is squeezed, actuating end 114a of trigger 114 also compresses return compression spring 124. As main drive rod 122 of handle assembly 110 is distally advanced, due to an actuation of trigger 114, main drive rod 122 advances rocker 126 to act on drive sled 308 of cartridge assembly 300 to move drive sled 308 in a distal direction and to move cartridge clip pusher bar 304 in a distal direction, as described above.

As cartridge clip pusher bar 304 is moved in a distal direction, pusher 304d thereof engages the backspan of distal-most clip "C1" and pushes distal-most clip "C1" distally, out of clip cartridge assembly 300 and into the pair of jaws 320a.

Additionally, and simultaneously with a distal movement of the distal-most clip "C1", as cartridge clip pusher bar 304 of clip cartridge assembly 300 moves in a distal direction, the remaining surgical clips "C", main drive rod 122, and first jaw pusher 130 are also being moved in a distal direction. Following loading of distal-most clip "C1" into the pair of jaws 320a, as shown in FIGS. 32 and 33, cam ramp 126c of rocker 126 abuts or engages release or reversing feature 220 of outer tube assembly 200, to pivot rocker 126 about pivot pin 127, thereby disengaging piston 126b of rocker 126 from drive sled 308, to effectuate a reversal of the direction of travel of clip cartridge pusher bar 304, from the distal direction to a proximal direction.

As cartridge clip pusher bar 304 is moved in a proximal direction, cartridge clip pusher bar 304 acts on the backspans of the remaining surgical clips "C" to also urge the remaining surgical clips "C" in a proximal direction. Specifically, fingers 304e of cartridge clip pusher bar 304 proximally retract the remaining surgical clips "C" until each remaining surgical clip "C" is retracted into contact with a respective distal tip of a respective resilient, deflectable finger 302d of clip tray 302, which blocks or stops further proximal retraction of the remaining surgical clips "C", while cartridge clip pusher bar 304 continues to move proximally to the proximal-most position thereof.

With cartridge clip pusher bar 304 returned to the proximal-most position thereof, continued squeezing of trigger 114 continues to advance main drive rod 122 in a distal direction along with first jaw pusher 130. As trigger 114 is squeezed further, first jaw pusher 130 abuts second jaw pusher 132 and urges second jaw pusher 132 in a distal direction. Trigger 114 is squeezed further such that main drive rod 122, first jaw pusher 130, and second jaw pusher reach a distal-most position thereof (e.g., total distal advancement of about 17 mm), until the V-shaped cam groove 132e of second jaw pusher 132 engages cam teeth 320c of the pair of jaws 320a to close the pair of jaws 320a, and form the distal-most clip "C1" loaded therewith.

Following formation of the distal-most clip "C1", trigger 114 may be released, whereby return compression spring 124 is permitted to re-expand to act on flange 122c and move main drive rod 122 and first and second jaw pushers 130, 132 in a proximal direction until each of main drive rod 122, first jaw pusher 130, and second jaw pusher 132 are returned to a proximal-most position thereof. In this manner, with reference to FIGS. 34 and 35, as first jaw pusher 130 is returned to a proximal position, a barb 130c disposed on a distal end 130b thereof engages a corresponding barb 132c disposed on a proximal end 132a of second pusher bar 132. Barb 132c is disposed on second jaw pusher 132 in a manner such that a gap exists between barb 132c and proximal surface 132d, thereby allowing first jaw pusher 130 to travel in a proximal and distal direction without affecting movement of second jaw pusher 132.

When main drive rod 122 is returned to the proximal-most position thereof, cam ramp 126c of rocker 126 is moved proximally of release or reversing feature 220 of outer tube assembly 200, whereby biasing member leaf spring 128, acting on proximal end 126a of rocker 126 pivots rocker 126 such that piston 126b of rocker is brought back into axial registration with drive sled 308 of clip cartridge assembly 300.

Additionally, as main drive rod 122, and therefore, first jaw pusher 130 and second jaw pusher 132 are returned to a proximal-most position thereof, the V-shaped cam groove 132e of second jaw pusher 132 is withdrawn from and engages cam teeth 320c of the pair of jaws 320a thereby allowing the pair of jaws 320a to open as a result of their own resilient bias.

The operations described above can be repeated, as required, until all of the surgical clips "C" have been formed.

Surgical clip applier 100 may be provided with a lockout mechanism, wherein surgical clip applier 100 cannot be actuated once all of the surgical clips "C" have been fired. By way of example only, one such lockout mechanism may include spaced apart prongs $304d_1$, $304d_2$ of pusher 304d entering into and engaging the pair of channels 302f of clip tray 302 (FIG. 28A) once the final clip of the stack of clips "C" is formed and cartridge clip pusher bar 304 is retracted to the proximal-most position. Once the spaced apart prongs $304d_1$, $304d_2$ of pusher 304d are engaged with or disposed within the pair of channels 302f of clip tray 302, any distal movement of the cartridge clip pusher bar 304, e.g., upon an actuation of trigger 114, as described above, is inhibited.

In use, surgical clip applier 100, as mentioned above, is capable of loading different surgical clip cartridge assemblies 300 on outer tube assembly 200. Specifically, clip applier 100 may be loaded with a surgical clip cartridge assembly 300 that is loaded with a stack of surgical clips "C" having a first size, or a surgical clip cartridge assembly 300 that is loaded with a stack of surgical clips "C" having a second size different than the first size.

In this manner, the user or surgeon may load a surgical clip cartridge assembly 300, loaded with a particular size of surgical clips, depending on the particular surgical procedure to be performed. Additionally, during a surgical procedure, if the need arises to use a different sized surgical clip, the user or surgeon may eject or unload the surgical clip cartridge assembly 300 that is loaded onto outer tube assembly 200 and then load a new surgical clip cartridge assembly 300 (having a different sized stack of surgical clips loaded therein as compared to the unloaded surgical clip cartridge assembly 300) onto outer tube assembly 200.

Additionally, in accordance with the present disclosure, handle assembly 110 and outer tube assembly 200 may be reused following proper cleaning, sterilizing, autoclaving and the like, and clip cartridge assembly 300 is disposed following a complete and/or partial use thereof.

Also in accordance with the present disclosure, it is further contemplated that a surgical kit may be provided including a surgical clip applier 100 and a plurality of clip cartridge assemblies 300 including at least a first set of clip cartridge assemblies loaded with a stack of surgical clips having a first size and a second set of clip cartridge assemblies loaded with a stack of surgical clips having a second size different than the first size. The kit may include instructions for the assembly or surgical clip applier 100, the use of surgical clip applier 100, and the processing of surgical clip applier assembly 100 following use, a surgical clip applier 100 including a single handle assembly 110, a single outer tube assembly 200, a single clip cartridge assembly 300, and a package, container or box configured to retain the same.

Surgical instruments such as the clip appliers described herein may also be configured to work with robotic surgical systems and what is commonly referred to as "Telesurgery." Such systems employ various robotic elements to assist the surgeon and allow remote operation (or partial remote operation) of surgical instrumentation. Various robotic arms, gears, cams, pulleys, electric and mechanical motors, etc. may be employed for this purpose and may be designed with a robotic surgical system to assist the surgeon during the course of an operation or treatment. Such robotic systems may include remotely steerable systems, automatically flexible surgical systems, remotely flexible surgical systems, remotely articulating surgical systems, wireless surgical systems, modular or selectively configurable remotely operated surgical systems, etc.

The robotic surgical systems may be employed with one or more consoles that are next to the operating theater or located in a remote location. In this instance, one team of surgeons or nurses may prep the patient for surgery and configure the robotic surgical system with one or more of the instruments disclosed herein while another surgeon (or group of surgeons) remotely control the instruments via the robotic surgical system. As can be appreciated, a highly skilled surgeon may perform multiple operations in multiple locations without leaving his/her remote console which can be both economically advantageous and a benefit to the patient or a series of patients.

The robotic arms of the surgical system are typically coupled to a pair of master handles by a controller. The handles can be moved by the surgeon to produce a corresponding movement of the working ends of any type of surgical instrument (e.g., end effectors, graspers, knifes, scissors, etc.) which may complement the use of one or more of the embodiments described herein. The movement of the master handles may be scaled so that the working ends have a corresponding movement that is different, smaller or larger, than the movement performed by the operating hands of the surgeon. The scale factor or gearing ratio may be adjustable so that the operator can control the resolution of the working ends of the surgical instrument(s).

The master handles may include various sensors to provide feedback to the surgeon relating to various tissue parameters or conditions, e.g., tissue resistance due to manipulation, cutting or otherwise treating, pressure by the instrument onto the tissue, tissue temperature, tissue impedance, etc. As can be appreciated, such sensors provide the surgeon with enhanced tactile feedback simulating actual operating conditions. The master handles may also include a variety of different actuators for delicate tissue manipulation or treatment further enhancing the surgeon's ability to mimic actual operating conditions.

Figure 43:
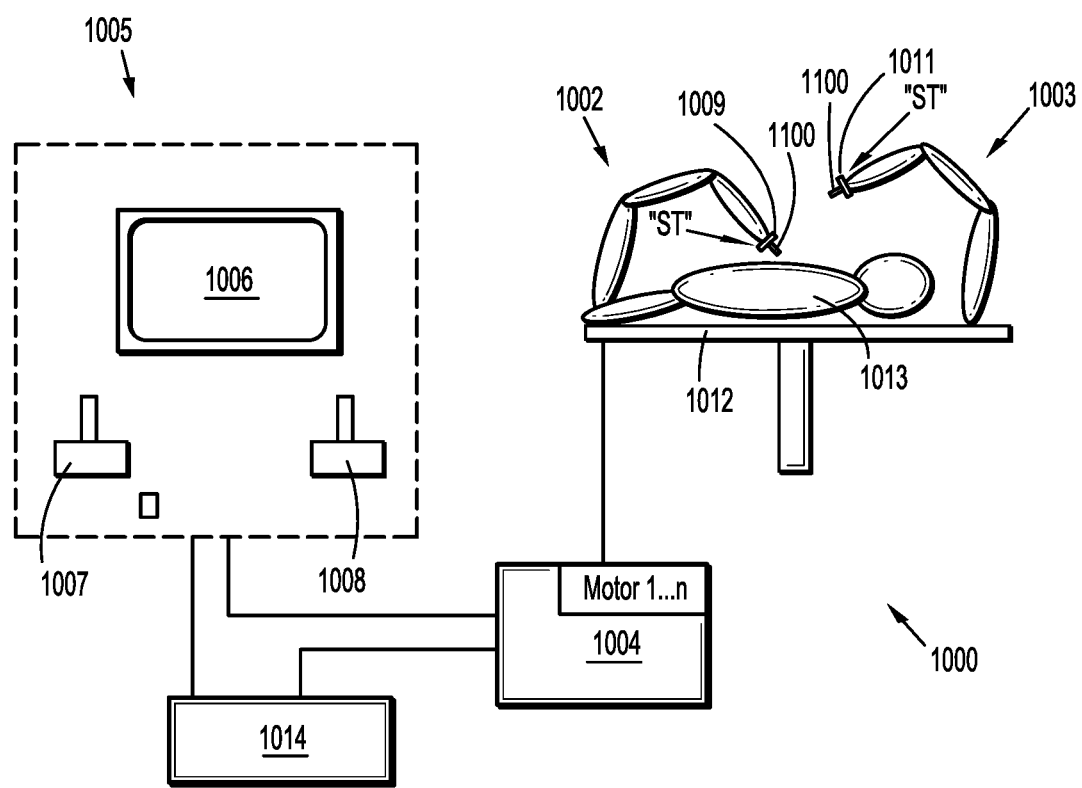
FIG. 43 is a schematic illustration of a robotic surgical system configured for use in accordance with the present disclosure.

Referring to FIG. 43, a medical work station is shown generally as work station 1000 and generally may include a plurality of robot arms 1002, 1003; a control device 1004; and an operating console 1005 coupled with control device 1004. Operating console 1005 may include a display device 1006, which may be set up in particular to display three-dimensional images; and manual input devices 1007, 1008, by means of which a person (not shown), for example a surgeon, may be able to telemanipulate robot arms 1002, 1003 in a first operating mode.

Each of the robot arms 1002, 1003 may include a plurality of members, which are connected through joints, and an attaching device 1009, 1011, to which may be attached, for example, a surgical tool "ST" supporting an end effector 1100, in accordance with any one of several embodiments disclosed herein, as will be described in greater detail below.

Robot arms 1002, 1003 may be driven by electric drives (not shown) that are connected to control device 1004. Control device 1004 (e.g., a computer) may be set up to activate the drives, in particular by means of a computer program, in such a way that robot arms 1002, 1003, their attaching devices 1009, 1011 and thus the surgical tool (including end effector 1100) execute a desired movement according to a movement defined by means of manual input devices 1007, 1008. Control device 1004 may also be set up in such a way that it regulates the movement of robot arms 1002, 1003 and/or of the drives.

Medical work station 1000 may be configured for use on a patient 1013 lying on a patient table 1012 to be treated in a minimally invasive manner by means of end effector 1100. Medical work station 1000 may also include more than two robot arms 1002, 1003, the additional robot arms likewise being connected to control device 1004 and being telemanipulatable by means of operating console 1005. A medical instrument or surgical tool (including an end effector 1100) may also be attached to the additional robot arm. Medical work station 1000 may include a database 1014, in particular coupled to with control device 1004, in which are stored, for example, pre-operative data from patient/living being 1013 and/or anatomical atlases.

Reference is made herein to U.S. Patent Publication No. 2012/0116416, filed on Nov. 3, 2011, entitled "Medical Workstation," the entire content of which is incorporated herein by reference, for a more detailed discussion of the construction and operation of an exemplary robotic surgical system.

It is contemplated, and within the scope of the present disclosure, that other endoscopic assemblies, including a pair of jaws having a unique and diverse closure stroke length thereof, may be provided with a drive assembly, similar to any of the drive assemblies described herein, for accommodating and adapting the closure stroke length for the pair of jaws thereof to the constant trigger stroke length.

Accordingly, various endoscopic assemblies, constructed in accordance with the principles of the present disclosure, may be provided which are also capable of firing or forming or closing surgical clips of various sizes, materials, and configurations, across multiple platforms for multiple different manufactures.

It should be understood that the foregoing description is only illustrative of the present disclosure. Various alternatives and modifications can be devised by those skilled in the art without departing from the disclosure. Accordingly, the present disclosure is intended to embrace all such alternatives, modifications and variances. The embodiments described with reference to the attached drawing figures are presented only to demonstrate certain examples of the disclosure. Other elements, steps, methods and techniques that are insubstantially different from those described above and/or in the appended claims are also intended to be within the scope of the disclosure.

What is claimed is:

1. A reposable surgical clip applier, comprising:
a handle assembly including a housing, a fixed handle, a trigger, and a drive assembly removably supported within the housing and operatively actuatable by the trigger, the drive assembly including a drive rod having a proximal end and a distal end, wherein the distal end of the drive rod defines a tab extending therefrom;
an outer tube assembly disposed on a distal end of the housing and extending distally therefrom; and
a clip cartridge assembly selectively connectable to a distal end of the outer tube assembly, the clip cartridge assembly including:
an outer tube;
a pair of jaws fixedly supported in a distal end of the outer tube;
a first jaw pusher in selective engagement with the distal end of the drive rod;
a second jaw pusher, wherein a proximal end of the second jaw pusher is in selective engagement with the first jaw pusher and a distal end of the second jaw pusher is in selective engagement with the pair of jaws, wherein a proximal end of the first jaw pusher includes a pocket defined therein, the pocket configured to selectively engage the tab of the drive rod, wherein when a pair of tabs of the first jaw pusher are received within a corresponding pair of windows of the outer tube, the pocket of the first jaw pusher is permitted to receive the tab of the drive rod; and
a plurality of surgical clips disposed within the outer tube.

2. The reposable surgical clip applier according to claim 1, wherein the outer tube of the clip cartridge assembly further includes the pair of windows defined therein, the pair of windows configured to receive the corresponding pair of tabs extending from each side of the first jaw pusher.

3. The reposable surgical clip applier according to claim 1, wherein actuation of the trigger causes distal movement of the drive rod and the first jaw pusher, wherein continued actuation of the trigger causes a distal end of the first jaw pusher to abut a proximal surface of the second jaw pusher, thereby urging the second jaw pusher in a distal direction.

4. The reposable surgical clip applier of claim 1, wherein the housing of the handle assembly includes a barrel housing having the fixed handle extending therefrom, the barrel housing defining a bore therethrough, an open proximal end, and an open distal end; and
wherein the trigger is pivotally supported on and extends from the barrel housing, the trigger including an actuating end extending into the bore of the barrel housing.

5. The reposable surgical clip applier of claim 4, further including an end cap including a bore defined therein, the end cap configured to be received within the open proximal end of the bore of the housing.

6. The reposable surgical clip applier of claim 5, wherein the drive rod includes an elongate extension extending from the proximal end of the drive rod and extending in a proximal direction therefrom, the elongate extension configured to be slidably received within the bore of the threaded cap.

7. The reposable surgical clip applier according to claim 4, wherein the trigger of the handle assembly includes an actuating end, wherein the actuating end of the trigger is disposed proximal of the drive rod and is in operative contact with the drive rod.

8. The reposable surgical clip applier according to claim 7, wherein the trigger of the handle assembly is pivotable to a position wherein the actuating end of the trigger is not within the bore of the barrel housing.

9. The reposable surgical clip applier according to claim 8, wherein, when the actuating end of the trigger is not within the bore of the barrel housing, the distal end of the drive assembly is insertable into the open proximal end of the barrel housing and advanceable through the barrel housing and at least partially through the outer tube assembly.

10. The reposable surgical clip applier according to claim 4, wherein the outer tube assembly includes a knob supporting the outer tube of the clip cartridge assembly, wherein the barrel housing of the handle assembly and the knob of the outer tube assembly are selectively connectable to one another via a bayonet-type connection.

11. The reposable surgical clip applier according to claim 1, wherein a proximal end of the clip cartridge assembly is selectively connectable to the outer tube assembly via a snap-fit connection.

12. A reposable surgical clip applier, comprising:
a handle assembly including a housing, a fixed handle, a trigger, and a drive assembly removably supported within the housing and operatively actuatable by the trigger, the drive assembly including a drive rod having a proximal end and a distal end;
an outer tube assembly disposed on a distal end of the housing and extending distally therefrom; and
a clip cartridge assembly selectively connectable to a distal end of the outer tube assembly, the clip cartridge assembly including:
an outer tube;
a pair of jaws fixedly supported in a distal end of the outer tube;
a first jaw pusher in selective engagement with the distal end of the drive rod, wherein the first jaw pusher includes a barb defined on a distal end thereof;
a second jaw pusher, wherein a proximal end of the second jaw pusher is in selective engagement with the first jaw pusher and a distal end of the second jaw pusher is in selective engagement with the pair of jaws, wherein the second jaw pusher includes a barb defined on the proximal end thereof, the barb of the first jaw pusher configured to engage the barb of the second jaw pusher as the first jaw pusher travels in a proximal direction; and
a plurality of surgical clips disposed within the outer tube.

* * * * *